US005504190A

United States Patent [19]
Houghten et al.

[11] Patent Number: 5,504,190
[45] Date of Patent: Apr. 2, 1996

[54] EQUIMOLAR MULTIPLE OLIGOMER MIXTURES, ESPECIALLY OLIGOPEPTIDE MIXTURES

[75] Inventors: Richard A. Houghten, Solana Beach; Julio H. Cuervo, La Jolla; Clemencia Pinilla; Jon R. Appel, Jr., both of Cardiff; Silvie Blondelle, La Jolla, all of Calif.

[73] Assignee: Torrey Pines Institute for Molecular Studies, San Diego, Calif.

[21] Appl. No.: 253,854

[22] Filed: Jun. 3, 1994

Related U.S. Application Data

[60] Division of Ser. No. 797,551, Nov. 19, 1991, abandoned, which is a continuation-in-part of Ser. No. 701,658, May 16, 1991, abandoned, which is a continuation-in-part of Ser. No. 617,023, Nov. 21, 1990, abandoned.

[51] Int. Cl.⁶ .......................... A61K 38/04; C07K 5/00; C07K 7/00; C07K 16/00
[52] U.S. Cl. .......................... 530/329; 530/328; 530/327; 530/326; 530/325; 530/324
[58] Field of Search .......................... 530/329, 328, 530/327, 326, 325, 324; 514/17, 16, 15, 14, 13, 12

[56] References Cited

U.S. PATENT DOCUMENTS

| | | | |
|---|---|---|---|
| 3,544,404 | 12/1970 | Johnson et al. | 156/148 |
| 4,226,857 | 10/1980 | Momany | 424/177 |
| 4,282,143 | 8/1981 | Sarantakis | 260/112.55 |
| 4,304,692 | 12/1981 | Hughes et al. | 260/8 |
| 4,483,964 | 11/1984 | Urdea et al. | 525/54.23 |
| 4,507,433 | 3/1985 | Miller et al. | 525/54.11 |
| 4,631,211 | 12/1986 | Houghten | 428/35 |
| 4,708,871 | 11/1987 | Geysen | 424/88 |
| 4,831,211 | 5/1989 | Geysen | 436/501 |
| 5,010,175 | 4/1991 | Rutter et al. | 530/334 |
| 5,182,366 | 1/1993 | Huebner et al. | 530/334 |
| 5,194,392 | 3/1993 | Geysen | 436/518 |

FOREIGN PATENT DOCUMENTS

| | | | |
|---|---|---|---|
| 8403564 | 9/1984 | WIPO . | |
| 8403506 | 9/1984 | WIPO . | |
| 8600991 | 2/1986 | WIPO . | |
| 9209300 | 6/1992 | WIPO | A61K 37/02 |

OTHER PUBLICATIONS

Abstract No. 288, *Xth International Symposium on Medicinal Chemistry*, Budapest, Hungary, Aug. 15–18, 1988, p. 168.
*IN*: "Innovation and Perspectives in Solid Phase Synthesis: Peptides, Polypeptides and Oligognucleotides", R. Epton, ed., Intercept Limited, Andover, pp. 237–239 (1992).
*IN*: "Peptides: Chemistry and Biology, Proceedings of the 12th American Peptide Symposium", J. A. Smith & J. E. Rivier, eds., ESCOM, Leiden, pp. 560–561 (1992).
Pinilla et al., *Vaccines 92*, Cold Spring Harbor Laboratory Press, pp. 25–28 (1992).
Houghten et al., *BioTechniques*, 13(3):412–421 (1992).
Appel, et al., *Immunomethods 1*, Academic Press, Inc., 17–23 (1992).
Pinilla et al., *BioTechniques*, 13:6, 901–905 (1992).
Geysen et al., *Proc. Natl. Acad. Sci. USA*, 81:3998–4002 (Jul. 1984).
Geysen et al., *Proc. Natl. Acad. Sci. USA*, 82:178–182 (Jan., 1985).
Geysen et al., "The Delineation of Peptides Able to Mimic Assembled Epitopes", in 1986 Synthetic Peptides as Antigens, (CIBA Foundation Symposium 119), pp. 130–149 (1986)–[1986a].
Geysen et al., *Molecular Immunology*, 23(7):709–715 (1986)–[1986b].
Geysen et al., *J. Immunol. Meth.*, 102:259–274 (1987).
Mason et al., "Diversity of the Antibody Response", in Vaccines 86, pp. 97–103 (1986).
Merrifield, *J. Amer. Chem. Soc.*, 85(14); 2149–2154 (Jul. 20, 1963).
Rodda et al., *Molecular Immunology*, 23(6):603–610 (1986).
Schoofs et al., *J. Immunol.*, 140(2):611–616 (Jan. 15, 1988).
Furka et al., (1988, 14th International Congress of Biochemistry, vol. 5, Abstract FR:013).
Houghten, *Proc. Natl. Acad. Sci.*, 82:5131–5135 (1985).
Houghten, et al., *Biotechniques*, 4(6):522–528 (1986).
Devlin et al., *Science*, 249:404–405 (1990).
Scott et al., *Science*, 249:386–390 (1990).
Fodor et al., *Science*, 251:767–773 (1991).
Houghten et al., *Vaccines 1986*, pp. 21–25 (1987).
Houghten et al., *Nature*, 354:84–86 (Nov. 7, 1991).
Lem et al., *Letters to Nature*, 354:82 (Nov. 7, 1991).
Furka et al, *Int. J. Peptide Protein Res.*, 37:487–493 (1991).
Van der Zee et al., *Eur. J. Immunol.*, 19:43–47 (1989).
Merrifield, *Angew. Chem. Int. Ed. Engl.*, 24:799 (Oct. 1985).

*Primary Examiner*—Jill Warden
*Assistant Examiner*—A. M. Davenport
*Attorney, Agent, or Firm*—Welsh & Katz

[57] ABSTRACT

A process for the synthesis of a complex mixture pool of solid support-coupled monomeric repeating unit compounds such as amino acid derivatives is disclosed in which the mixture pool contains an equimolar representation of reacted monomeric repeating unit compounds coupled. Also disclosed is a process for the stepwise synthesis of a complex mixture of coupled or free, unsupported oligomers such as oligopeptides. A set of self-solubilizing, unsupported mixed oligopeptides having one or more predetermined amino acid residues at one or more of the same, predetermined positions in the oligopeptide chain in which the set contains equimolar amounts of a plurality of different amino acid residues, preferably at least six different residues, at one or more of the same predetermined positions of the oligopeptide chain is also disclosed, as are methods of making and using the same.

5 Claims, 11 Drawing Sheets

EQUIMOLAR MULTIPLE OLIGOMER MIXTURES, ESPECIALLY OLIGOPEPTIDE MIXTURES

CROSS-REFERENCE TO RELATED APPLICATION

This is a division, of application Ser. No. 07/797,551, filed Nov. 19, 1991 and now abandoned, which is a continuation-in-part of application Ser. No. 07/701,658 filed May 16, 1991 and now abandoned, that was a continuation-in-part of application Ser. No. 07/617,023, filed Nov. 21, 1990 and now abandoned, whose disclosures are incorporated by reference.

TECHNICAL FIELD

The present invention relates to the organic synthesis of oligomeric sequences of compounds. More particularly it relates to stepwise synthesis of multiple independent sequences, especially oligomeric peptide chains.

BACKGROUND AND RELATED ART

Over the last several years, developments in peptide synthesis technology have resulted in automated synthesis of peptides accomplished through the use of solid phase synthesis methods. The solid phase synthesis chemistry that made this technology possible was first described in Merrifield et al. *J. Amer. Chem. Soc.*, 85:2149–2154 (1963). The "Merrifield method" has for the most part remained unchanged and is used in nearly all automated peptide synthesizers available today.

In brief, the Merrifield method involves synthesis of a peptide chain on solid support resin particles. These particles typically consist of polystyrene cross-linked with divinyl benzene to form porous beads which are insoluble in both water and various organic solvents used in the synthesis protocol. The resin particles contain a fixed amount of amino- or hydroxylmethyl aromatic moiety which serves as the linkage point for the first amino acid in the peptide.

Attachment of the first amino acid entails chemically reacting its carboxyl-terminal (C-terminal) end with derivatized resin to form the carboxyl-terminal end of the oligopeptide. The alpha-amino end of the amino acid is typically blocked with a t-butoxy-carbonyl group (t-Boc) or with a 9-fluorenylmethyloxycarbonyl (F-Moc) group to prevent the amino group which could otherwise react from participating in the coupling reaction. The side chain groups of the amino acids, if reactive, are also blocked (or protected) by various benzyl-derived protecting groups in the form of ethers, thioethers, esters, and carbamates.

The next step and subsequent repetitive cycles involve deblocking the amino-terminal (N-terminal) resin-bound amino acid (or terminal residue of the peptide chain) to remove the alpha-amino blocking group, followed by chemical addition (coupling) of the next blocked amino acid. This process is repeated for however many cycles are necessary to synthesize the entire peptide chain of interest. After each of the coupling and deblocking steps, the resin-bound peptide is thoroughly washed to remove any residual reactants before proceeding to the next. The solid support particles facilitate removal of reagents at any given step as the resin and resin-bound peptide can be readily filtered and washed while being held in a column or device with porous openings.

Synthesized peptides are released from the resin by acid catalysis (typically with hydrofluoric acid or trifluoroacetic acid), which cleaves the peptide from the resin leaving an amide or carboxyl group on its C-terminal amino acid. Acidolytic cleavage also serves to remove the protecting groups from the side chains of the amino acids in the synthesized peptide. Finished peptides can then be purified by any one of a variety of chromatography methods.

Though most peptides are synthesized with the above described procedure using automated instruments, a recent advance in the solid phase method by R. A. Houghten allows for synthesis of multiple independent peptides simultaneously through manually performed means. The "Simultaneous Multiple Peptide Synthesis" ("SMPS") process is described in U.S. Pat. No. 4,631,211 (1986); Houghten, *Proc. Natl. Acad. Sci.*, 82:5131–5135 (1985); Houghten et al., *Int. J. Peptide Protein Res.*, 27:673–678 (1986); Houghten et al., *Biotechniques*, 4, 6, 522–528 (1986), and Houghten, U.S. Pat. No. 4,631,211, whose disclosures are incorporated by reference.

Illustratively, the SMPS process employs porous containers such as plastic bags to hold the solid support synthesis resin. A Merrifield-type solid-phase procedure is carried out with the resin-containing bags grouped together appropriately at any given step for addition of the same, desired amino acid residue. The bags are then washed, separated and regrouped for addition of subsequent same or different amino acid residues until peptides of the intended length and sequence have been synthesized on the separate resins within each respective bag.

That method allows multiple, but separate, peptides to be synthesized at one time, since the peptide-linked resins are maintained in their separate bags throughout the process. The SMPS method has been used to synthesize as many as 200 separate peptides by a single technician in as little as two weeks, a rate vastly exceeding the output of most automated peptide synthesizers.

A robotic device for automated multiple peptide synthesis has been recently commercialized. The device performs the sequential steps of multiple, separate solid phase peptide synthesis through iterative mechanical-intensive means. This instrument can synthesize up to 96 separate peptides at one time, but is limited at present by the quantity of its peptide yield.

Several research groups have reported the synthesis of synthetic combinatorial libraries of peptides. Those reports are discussed below.

Of interest is work by Geysen et al., which deals with methods for synthesizing peptides with specific sequences of amino acids and then using those peptides to identify reactions with various receptors. Geysen et al.'s work presupposes that one has a prior knowledge of the general nature of the sequences required for the particular receptors, so that the appropriate group of peptides can be synthesized. See U.S. Pat. Nos. 4,708,871 and 4,833,092; P.C.T. Publications Nos. WO 84/03506 and WO 84/03564; Geysen et al., *Proc. Natl. Acad. Sci. U.S.A.*, 81:3998–4002 (1984); Geysen et al., *Proc. Natl. Acad. Sci. U.S.A.*, 82:178–182 (1985); Geysen et al., in *Synthetic Peptides as Antigens*, 130–149 (1986); Geysen et al., *J. Immunol. Meth.*, 102:259–274 (1987); and Schoofs et al., *J. Immunol.*, 140:611–616 (1988).

In published PCT application PCT/AU85/00165 (WO 86/00991), Geysen describes a method for determining so-called "mimotopes". A mimotope is defined as a catamer (a polymer of precisely defined sequence formed by the condensation of a precise number of small molecules), which in at least one of its conformations has a surface region with the equivalent molecule topology to the epitope of which it is a mimic. An epitope is defined as the surface of an antigenic molecule which is delineated by the area of interaction with an antibody molecule.

The mimotopes are synthesized on a series of solid polymer (e.g. polyethylene with a coating of grafted acrylic acid) rods having a diameter of about 4 mm and a length of about 50 mm. A spacer formed by reaction of the ε-amino group of t-Boc-lysine methyl ester and then t-Boc-alanine was added to the resins, followed by removal of the t-Boc group to provide an amino group to be used to begin the syntheses.

A mixture of blocked amino acids containing different amounts of each of the blocked twenty amino acids to be used was dissolved in dimethyl formamide and then coupled to the rods. That first coupling was repeated three times using conventional solid phase synthesis techniques. Twenty amino acid residues were individually next added so that twenty 5-mer sequences were prepared, each having a single, known amino acid residue at the amino-terminus and a mixture of amino acid residues at each of the four other positions of the chain. Each of those twenty rod-linked peptides was then individually reacted with each of the twenty amino acid residues to form 400 (20×20) 6-mer peptides having the two amino-terminal positions defined and the four remaining positions as mixtures. Two more positions of mixtures of amino acids were then added, and the terminal amine acetylated to form N-acetyl 8-mers linked to the rods whose first two amino acid positions were undefined (mixtures), followed by two defined positions, followed by four undefined positions (mixtures), followed by the spacer and then the supporting rods.

The 400 rod-linked N-acetyl 8-mer peptide mixture preparations were then screened in an ELISA assay using a monoclonal antibody to a desired antigenic protein. The 8-mers having the best binding to the antibody were identified. Two sets of further 8-mers that contained the identified best-binding 2-mer sequences within those 8-mers were prepared.

A first set contained mixed amino acids at the three C-terminal positions, followed toward the N-terminus, by a position containing each of the twenty amino acids made by twenty separate couplings, the identified 2-mer sequences, two further mixtures at the next two positions, and an N-terminal acetyl group. The second group contained mixed amino acids at the four C-terminal positions, the identified 2-mer sequences, a position made by separate couplings of each of the twenty amino acids, mixed amino acids as the terminal residues and an N-terminal acetyl group.

Each of those rod-linked N-acetyl 8-mers was again screened in an ELISA with the monoclonal antibody. The best binding sequences for each group were identified, and thus 4-mer, best-binding sequences were identified.

The above process of separately adding each of the amino acids on either side of identified best-binding sequences was repeated until an optimum binding sequence was identified.

The above method, while elegant, suffers from several disadvantages. First, owing to the small size of each rod used, relatively small amounts of each peptide is produced. Second, each assay is carried out using the rod-linked peptides, rather than the free peptides in solution. Third, even though specific amounts of each blocked amino acid are used to prepare the mixed amino acid residues at the desired positions, there is no way of ascertaining that an equimolar amount of each residue is truly present at those positions.

In addition, Furka et al., (1988, 14th International Congress of Biochemistry, Volume 5, Abstract FR:013) described the synthesis of nine tetrapeptides each of which contained a single residue at each of the amino- and carboxy-termini and mixtures of three residues at each position therebetween. The abstract futher asserts that those authors' experiments indicated that a mixture containing up to 180 pentapeptides could be easily synthesized in a single run. No biological assays were reported.

Recent reports (Devlin et al., *Science*, 249:404–405 [1990] and Scott et al., *Science,* 249:386–390 [1990]) have described the use of recombinant DNA and bacterial expression to create highly complex mixtures of peptides. For example, a 45-nucleotide base pair stretch of DNA was synthesized in which the individual nucleotide bases were varied to contain all four possible nucleotide bases (guanine, adenine, cytosine and thymidine) at every position in the synthesized DNA chain, except at each third position (3, 6, 9, etc.) which contained only guanine and cytosine. The omission of adenine and thymidine at every third position in the synthesized DNA removed the possibility of chain terminator triplet codons ending in A or T, such as TAA or TGA.

The resulting DNA sequence would then code for a mixture of 15-mer peptides with all combinations of the 20 naturally occurring amino acids at each position.

Those investigators fused the 45 synthetic nucleotide sequence to a gene coding for the coat protein of a simple bacteriophage and created a large library of these bacteriophages. Each member of the library contained a different 45-mer DNA fusion sequence and therefore each member of the library resulted in a different 15-mer peptide fused to the outer coat protein of its corresponding fully assembled bacteriophage particle. Screening of the recombinant bacteriophage particles in a biochemical assay allowed the investigators to find individual peptide-coat protein fusions (bacteriophages) that were active in that assay by enrichment, selection and clonal isolation of the enriched bacteriophages that contained active peptide fusions. By determining the DNA sequence of the cloned bacteriophages, the investigators could deduce which peptide sequences were active in their assay.

That method yielded several peptide sequences from a mixture of $10^7$ or more recombinant bacteriophages. Each of the 15-mer peptides found contained the same four-amino-acid sequence somewhere within its overall sequence, thereby allegedly validating the assay accuracy and methodological approach.

The recombinant DNA method is extremely powerful for screening large numbers of peptides. However, it is limited in that the peptides must be fused to a larger protein as a result of and integral to the design of the method. The peptide-protein fusions (and corresponding bacteriophage particles) are likely to be unreactive in many biochemical, biological and in vivo assays where the peptides must be present in solution without steric hindrance or conformational distortion. In addition, the method results in an over-representation of some sequences of peptides due to the inherent redundancy of the genetic code which has several codons per amino acid in some cases and only one codon per amino acid in others.

Still further, neither group reported data as being definitive for the determination of optional peptide ligands for strepavidin (Devlin et al.), or for the two monoclonal antibodies raised against myohemorythinin (Smith et al.). Neither group provided a single specific answer comparable to the expected sequence.

More recently, Fodor et al., *Science,* 251:767–773 (1991), described the solid phase synthesis of mixtures of peptides or nucleotides on glass microscope slides treated with aminopropyltriethoxysilane to provide amine functional groups. Predetermined amino acids were then coupled to predefined areas of the slides by the use of photomasks. The photolabile protecting group NVOC (nitroveratryloxycarbonyl) was used as the amino-terminal protecting group.

By using irradiation, a photolabile protecting group and masking, an array of 1024 different peptides coupled to the slide was prepared in ten steps. Immunoreaction with a fluorescent-labeled monoclonal antibody was assayed with epifluorescence microscopy.

This elegant method is also limited by the small amount of peptide or oligonucleotide produced, by use of the synthesized peptide or nucleotide affixed to the slide, and also by the resolution of the photomasks. This method is also less useful where the epitope bound by the antibody is unknown because all of the possible sequences are not prepared.

The primary limitation of the above new approaches for the circumvention of individual screening of millions of individual peptides by the use of a combinatorial library is the inability of the peptides generated in those systems to interact in a "normal" manner with acceptor sites, analogous to natural interaction processes (i.e., in solution at a concentration relevant to the receptors, antibody binding sites, enzyme binding pockets, or the like being studied without the exclusion of a large percentage of the possible combinatorial library). Secondarily, the expression vector systems do not readily permit the incorporation of the D-forms of the natural amino acids or the wide variety of unnatural amine acids which would be of interest in the study or development of such interactions.

The interest in obtaining biologically active peptides for pharmaceutical, diagnostic and other uses would make desirable a procedure designed to find a mixture of peptides or a single peptide within a mixture with optimal activity for a target application. Screening mixtures of peptides enables the researcher to greatly simplify the search for useful therapeutic or diagnostic peptide compounds. Mixtures containing hundreds of thousands or more peptides should be readily screened since many biochemical, biological and small animal assays are sensitive enough to detect activity of compounds that have been diluted down to the nanogram or even picogram per milliliter range, the concentration range at which naturally occurring biological signals such as peptides and proteins operate.

Almost all of the broad diversity of biologically relevant ligand-receptor (or affector-acceptor) interactions occur in the presence of a complex milieu of other substances (i.e., proteins make up approximately 5–10 percent of plasma, e.g. albumin 1–3 percent, antibodies 2–5 percent-salts, lipids/fats, etc.). This is true for virtually all biologically active compounds since most are commonly present, and active, at nanomolar and lower concentrations. These compounds are also, in most instances, produced distant from their affection sites. That a small peptide (or other molecule) can readily "find" an acceptor system, bind to it, and affect a necessary biological function prior to being cleared from the circulation or degraded suggested that a single specific peptide sequence can be present in a very wide diversity, and concentration, of other individual peptides and still be recognized by its particular acceptor system (antibody, cellular receptor, etc.). If one could devise a means to prepare and screen a synthetic combinatorial library of peptides, then the normal exquisite selectivity of biological affector/acceptor systems could be used to screen through vast numbers of synthetic oligopeptides.

The availability of a wide variety of clearly identified peptides in relatively limited mixtures would greatly facilitate the search for the optimum peptide for any particular therapeutic end use application. At the present time, researchers are hampered by the inability to rapidly create, identify and screen large numbers of peptides with specific receptors. Work such as reported by Geysen has been valuable where the general nature of the required amino acid residue sequence could be previously determined, so that the specific peptides of interest could be individually formulated. However, such techniques cannot insure that the optimum peptides are identified for testing.

It would therefore be of considerable interest to have a method for the precise synthesis of mixtures of peptides in which individual peptide sequences can be specifically defined, such that a comprehensive array of peptides is available to researchers for the identification of one or more of the optimum peptides for reaction with receptors of interest, from which one can derive optimum therapeutic materials for treatment of various organism dysfunctions. It would also be of value for such a process to have the capability to produce equivalent sequences of other types of oligomeric compounds.

BRIEF SUMMARY OF THE INVENTION

In one aspect, the invention herein contemplates a process that provides for the synthesis of complex mixtures of step-growth oligomers, especially peptides, wherein each position in the oligomeric sequence chain contains an equimolar representation of reacted bifunctional monomeric repeating unit compound, such as an amino acid residue, added at that step. In peptide synthesis, the method circumvents the problem of unequal reaction yields during addition of blocked amino acids reacted as a mixture in a coupling step in the Merrifield solid phase synthesis procedure. Use of the present method also provides a relatively much larger amount of coupled oligomer than previously contemplated.

In its preferred embodiment, the invention contemplates the organic synthesis of complex equimolar mixtures of oligopeptide sequences on a solid support material. The equimolar oligopeptide sequences consist essentially of chains of amino acid residues linked end-to-end by peptide bonds wherein the amino acid residue incorporated at any one position in the chain can be varied, such as to contain all or a combination of the twenty naturally occurring amino acids and/or their derivatives. The invention enables synthesis of these peptide mixtures with equal and precise representation of any amino acid residues at any position in the chain at which a mixture of amino acid residues is intended to be represented. The process can use any type of peptide addition chemistry and protocols, but preferably uses the Merrifield solid phase synthesis procedure in protocols similar to that of the Houghten SMPS process.

In yet another aspect, the invention comprises a method for the identification of one or more optimum peptides for reaction with a designated acceptor, such that design of therapeutic materials for treatment of organism dysfunctions involving such receptor can be facilitated.

In its broadest form, a process of this invention is defined as a process for the synthesis of a complex mixture pool of solid support-coupled monomeric repeating unit compounds, wherein the mixture pool contains a substantially equimolar representation of the reacted monomeric repeating unit compound, such as amino acid residues, coupled at that step. In accordance with this method, (a) a plurality of solid supports is provided, each solid support comprised of a particle linked to reactive functional groups. The functional groups of the solid support react with a functional group of each of the monomeric repeating unit compounds to be reacted. In a preferred embodiment, each of the solid supports is within a porous container, the solid support is of a size that is larger than the pores of the container, and both the container and solid support are substantially insoluble in a liquid medium used during the stepwise synthesis.

(b) A plurality of liquid media is provided, each medium containing a different monomeric repeating unit compound from a plurality of monomeric repeating unit compounds from which the oligomers are to be formed. Each of the monomeric repeating unit compounds has a first reactive functional group that reacts with the reactive functional group of the solid support and a second reactive functional group that is capable of reacting during the reaction of the solid support functional group and the first reactive functional group, but is protected from so reacting by a selectively removable, covalently linked protecting group.

(c) Each of the solid supports is placed in a different one of the liquid media and the reactive functional group of each solid support is therein reacted with a first reactive functional group of a monomeric repeating unit compound in that respective medium to couple that monomeric repeating unit compound to the solid support.

(d) Each of the reactions is maintained for a time period and under conditions sufficient for all of the reactive functional groups of the solid support to couple to the monomeric repeating unit compound to form a plurality of monomeric repeating unit-coupled solid supports.

(e) Each monomeric repeating unit-coupled solid support is removed from its respective liquid medium, and equimolar amounts of each of the monomeric repeating unit-coupled solid supports are admixed to form a reaction product pool, wherein equal weights of the formed pool contain the same number of moles of each monomeric repeating unit-coupled solid support.

The above mixture pool is useful in a stepwise synthesis for preparing a complex mixture of solid support-coupled oligomers wherein one or more positions of each oligomer of the mixture contains an equimolar representation of reacted monomeric repeating unit compound coupled at each synthesis step. If desired, the pool formed in step (e) can be used for further steps (l)–(o) as discussed in regard to synthesis of an oligopeptide hereinafter. However, in usual practice, steps (f)–(k) are utilized, as discussed below.

(f) The reaction product pool is separated into a number of aliquots of equal weight. Each of the aliquots is enclosed in another porous container, where such preferred containers are used.

(g) The protecting groups are selectively removed from the second reactive functional groups of the pool to form a reacted solid support pool having free reactive functional groups. This step is preferably carried out after the pool is formed into aliquots and those aliquots are re-enclosed, but can be carried out prior to forming the aliquots, and re-enclosure is not used where porous containers are not used.

(h) Each of the aliquots having free reactive functional groups is placed into one of a number of liquid media, each medium containing a different monomeric repeating unit compound from a plurality of monomeric repeating unit compounds from which the oligomers are to be formed to form a reaction mixture, wherein each of the monomeric repeating unit compounds has a first reactive functional group that reacts in the reaction mixture with the free reactive groups of the aliquot and a second reactive functional group that is capable of reacting during the reaction of the free reactive functional groups of the aliquot, but is protected from so reacting by a selectively removable, covalently linked protecting group.

(i) Each of the reactions is maintained for a time period and under conditions sufficient for all of the free reactive functional groups of the aliquots to react with and couple to the respective monomeric repeating unit compounds to form a number of solid support-coupled repeating unit reaction products.

(j) Each of the solid support-coupled repeating unit reaction products formed is removed, and equimolar amounts of each of those reaction products are admixed to form a reaction product pool. Equal weights of the reaction product pool contain the same number of moles of each reaction product.

(k) Thereafter, steps (f) through (j) are serially repeated zero or more times until a plurality of solid support-coupled reaction products having the desired number of monomeric repeating units is synthesized.

The resulting complex mixture of oligomers contains an equimolar mixture of the plurality of monomeric repeating unit compounds at every predetermined position in the chain. The equimolarity is only limited by the accuracy in driving the reactions to completion and weighing errors in separating the substantially homogeneously mixed resins into equal aliquots.

In a preferred form, the process of this invention is defined as a process for the synthesis of a complex mixture pool of solid support-coupled amino acid residues wherein the mixture contains an equimolar representation of the amino acid residues coupled. Here, the preferred embodiment of using closed porous containers is described with the understanding that this description is for illustrative purposes only. According to this process, (a) at least six porous containers, each containing a solid support comprised of a particle linked to reactive functional groups are provided. The functional group of the solid support reacts with each amino acid to be reacted. The solid support is of a size that is larger than the pores of the container, and both the container and solid support are substantially insoluble in a liquid medium used during the stepwise synthesis.

(b) At least six liquid media are provided, each medium containing a different protected amino acid derivative from a plurality of protected amino acid derivatives from which the oligopeptides are to be formed. Each of the protected amino acid derivatives has a first reactive functional group that reacts with the reactive functional group of the solid support, and a second reactive functional group that is capable of reacting during the reaction of the solid support functional group and the first reactive functional group, but is protected from so reacting by a selectively removable, covalently linked protecting group.

(c) Each of the containers is placed in a different one of the liquid media and the reactive functional groups of each solid support in each container is therein reacted with a first reactive functional group of a protected amino acid derivative in that respective medium to couple that protected amino acid derivative to the solid support.

(d) Each of the reactions is maintained for a time period and under conditions sufficient for all of the reactive functional groups of the solid support to couple to the protected amino acid derivative to form a plurality of protected amino acid residue-coupled solid supports.

(e) Each protected amino acid residue-coupled solid support is removed from its respective container. Equimolar amounts of the protected amino acid residue-coupled solid supports are admixed to form a reaction product pool, wherein equal weights of the formed pool contain the same number of moles of each protected amino acid residue-coupled solid support.

The above mixture pool is useful in the stepwise synthesis of a complex mixture of oligopeptides in which one or more positions of each oligopeptide of the mixture contains an equimolar representation of amino acid residues added at each synthesis step. Here, again, the worker using this process will often continue with steps (f)–(k), below. However, in some instances, it can be desired to first follow steps (l)–(o), and then if desired, follow steps (f)–(k).

(f) The reaction product pool is separated into at least six aliquots of equal weight. Each of the aliquots is enclosed in another porous container.

(g) The protecting groups are selectively removed from the second reactive functional groups of the pool to form a reacted product pool having free reactive functional groups. Again, step (g) can precede step (f).

(h) Each of the enclosed aliquots having free reactive functional groups is placed into one of at least six liquid media, each medium containing a different protected amino acid derivative from a plurality of protected amino acid derivatives from which the oligopeptides are to be formed to form a reaction mixture, wherein each of said protected amino acid derivatives has a first reactive functional group that reacts with the free reactive groups of the enclosed reacted product pool aliquots and a second reactive functional group that is capable of reacting during the reaction of the free reactive functional groups of the pool, but is protected from so reacting by a selectively removable, covalently linked protecting group.

(i) Each of the reactions is maintained for a time period and under conditions sufficient for all of the free reactive functional groups of the enclosed reactant product pool aliquots to couple to the protected amino acid derivative to form at least six solid support-coupled protected amino acid residue reaction products.

(j) Each of the at least six reaction products formed in step (i) is removed, and equimolar amounts of each of those reaction products are admixed to form a reaction product pool. Equal weights of the reaction product pool contain the same number of moles of each reaction product.

(k) Thereafter, steps (f) through (j) are serially repeated zero or more times until a plurality of solid support-coupled reaction product oligopeptides having the desired number of amino acid residue repeating units is synthesized.

A complex mixture of solid support-coupled oligomers such as oligopeptides is useful in itself. For example, batches of 2-mer or longer coupled oligomers can be sold for others to utilize in syntheses and assays as described herein.

In another embodiment, one or more specifically defined, predetermined monomeric repeating unit compounds is added at one or more specific positions in the oligomeric chain. One or more positions in the chain on either side or both sides of the predetermined monomeric repeating unit compound contains the equimolar mixture of reacted monomeric repeating unit compounds.

More specifically, using the before-described synthesis of an oligopeptide as exemplary, (l) each of the protected amino acid derivative-coupled solid supports of step (k) is removed from its respective container. Equimolar amounts of protected amino acid derivative-coupled solid supports are admixed to form a further reaction product pool, wherein equal weights of the reaction product pool contain the same number of moles of each reaction product.

(m) An aliquot of the pool formed in step (l) is enclosed in a further porous container. The protecting groups are selectively removed from the second reactive functional groups to form a reacted solid support pool having free reactive functional groups. Deprotection can again precede enclosure of the aliquot.

(n) The enclosed pool aliquot having free second reactive functional groups is placed into a single liquid medium that contains a single protected amino acid derivative to form a reaction mixture in which the free reactive functional groups and single protected amino acid derivative react, the single protected amino acid derivative having a first reactive functional group that reacts with the free reactive groups of the pool aliquot, and a second reactive functional group that is capable of reacting during the reaction of the free reactive functional groups of the pool aliquot, but is protected from so reacting by a selectively removable covalently linked protecting group.

(o) The reaction mixture is maintained for a time period and under conditions sufficient for all of the free reactive functional groups of the pool aliquot to couple with the single protected amino acid derivative and form a solid support-coupled oligopeptide mixture having a single, predetermined amino acid residue in the same position in the oligopeptide chain.

After completion of step(o), one or more further single protected monomeric repeating unit compounds such as a protected amino acid derivative can be added (coupled). In addition, each of the monomeric repeating unit compounds can be added and the resulting reaction products pooled as discussed before to form a complex mixture of solid support-coupled oligomer reaction products that contains equimolar amounts of each monomeric repeating unit compound on either side of the single predetermined monomeric repeating unit compound. It is to be understood that the presence of equimolar amounts of each monomeric repeating unit compound or a single, predetermined monomeric repeating unit compound can be varied at any position in the oligomer chain that is desired.

The minimum number of monomeric repeating unit compounds from which an oligomer is formed is three for any of an oligonucleotide, oligosaccharide, or an oligopeptide, albeit at least six, more preferably at least ten different amino acid residues used in preparing oligopeptides. More preferably still, about 15 to about 20 different amino acids are used. For an oligopeptide, each of the twenty naturally occurring L-amino acids can be used as can the corresponding D-amino acids and D- and L-forms of non-natural amino acids such as ornithine, norleucine, hydroxyproline and beta-alanine. Use of mixtures of D- and L-forms is also contemplated.

In preferred practice, an oligomer such as an oligopeptide is coupled to the solid support by a selectively severable covalent bond, such as an ester or amide bond, an ultimately produced oligomer is cleaved (separated or severed) from the solid support, and is then recovered. The oligomers prepared by any of the before-described syntheses are linear.

A set of self-solubilizing, unsupported linear oligopeptides or mixture set; i.e., a complex mixture of oligopeptides prepared by a before-discussed process and severed or cleaved from the solid support, is also contemplated. Such a set consists essentially of a mixture of equimolar amounts of linear oligopeptide chains that contain the same number of amino acid residues in each oligopeptide chain. Each member of a set contains one or more single, predetermined amino acid residues at one or more predetermined positions of the oligopeptide chain and equimolar amounts of at least three, preferably at least six and more preferably about 15 to about 20, different amino acid residues at one or more other positions of the oligopeptide chain.

A plurality or set of sets of mixed unsupported linear oligopeptides as above is also contemplated. Each set of the plurality is the same (has the same sequence of equimolar amounts of a plurality of residues at one or more predetermined positions in this chain) except that the one or more single predetermined amino acid residue at a predetermined chain position within a set is different as between the plurality of sets.

A composition comprising a set of the before-defined self-solubilizing unsupported linear oligopeptide mixtures at a concentration of about one milligram per liter (mg/l) to about 100 g/l dissolved in an aqueous medium is also contemplated. That aqueous medium can be distilled or deionized water, a buffer solution, a growth medium for bacteria or other cells, or the like. In a particularly preferred embodiment, the aqueous medium is a cell growth medium that contains cells whose growth is to be assayed in the presence of the set of mixed self-solubilizing unsupported linear oligopeptides.

Another aspect of this invention constitutes an assay for binding of a set of mixed unsupported linear oligopeptides with an appropriate acceptor. A contemplated acceptor includes an antibody binding site (paratope), solubilized or non-solubilized cellular receptor molecules and whole living cells. An assay can be carried out in vitro or in vivo, as is appropriate. In this method, a before-described composition of an aqueous medium containing a set of unsupported linear oligopeptides as ligands or donors is contacted with acceptor molecules whose binding is to be assayed to form a binding reaction mixture. That mixture is maintained for a time period and under conditions for the acceptor to bind to an oligopeptide of the mixture, and the relative binding amount is determined.

In preferred practice, an above assay is repeated using another set of a before-described plurality of sets of the mixed self-solubilizing unsupported linear oligopeptides. Comparison of the relative binding results obtained provides a determination of which specific, identical amino acid residue at a predetermined position in the chain is best (or better) bound by the acceptor.

Relative binding amounts can be ascertained where an antibody or cellular receptor is used by usually used assay techniques such as competition ELISA or by relative amounts of radioactive decay of a bound oligopeptide where the mixed oligopeptides are radiolabeled, by use of fluorescently or chromophorically labeled oligopeptides or the like. Where whole, living cells or viruses are used as the acceptor, growth of the cells or inhibition of such growth can be used as the assay technique.

Yet another aspect of this invention is an antibiotic oligopeptide that includes the sequence Arg-Arg-Trp-Trp-Cys (SEQ ID NO:8). A preferred oligopeptide contains an N-terminal $C_1$–$C_8$ acyl group and a C-terminal amido group.

A particularly preferred oligopeptide contains six or seven residues and has the formula Ac-Arg-Arg-Trp-Trp-Cys-Xaa (SEQ ID NO:9), where Xaa is any of the twenty natural amino acid residues other than aspartic acid, glutamic acid and glycine. Most preferred is the oligopeptide of the formula Ac-Arg-Arg-Trp-Trp-Cys-Arg-$NH_2$ (SEQ ID NO:5). Other preferred oligopeptides include those having the 6-mer sequences shown below:

Phe-Arg-Trp-Trp-His-Xaa (SEQ ID NO:11);
Arg-Arg-Trp-Trp-Met-Xaa (SEQ ID NO:12);
Arg-Arg-Trp-Trp-Cys-Xaa (SEQ ID NO:13); and
Arg-Arg-Trp-Trp-Arg-Xaa (SEQ ID NO:14)
wherein Xaa is another amino acid resi.due.

BRIEF DESCRIPTION OF THE DRAWINGS

In the drawings forming a portion of this disclosure.

Figure 1A:
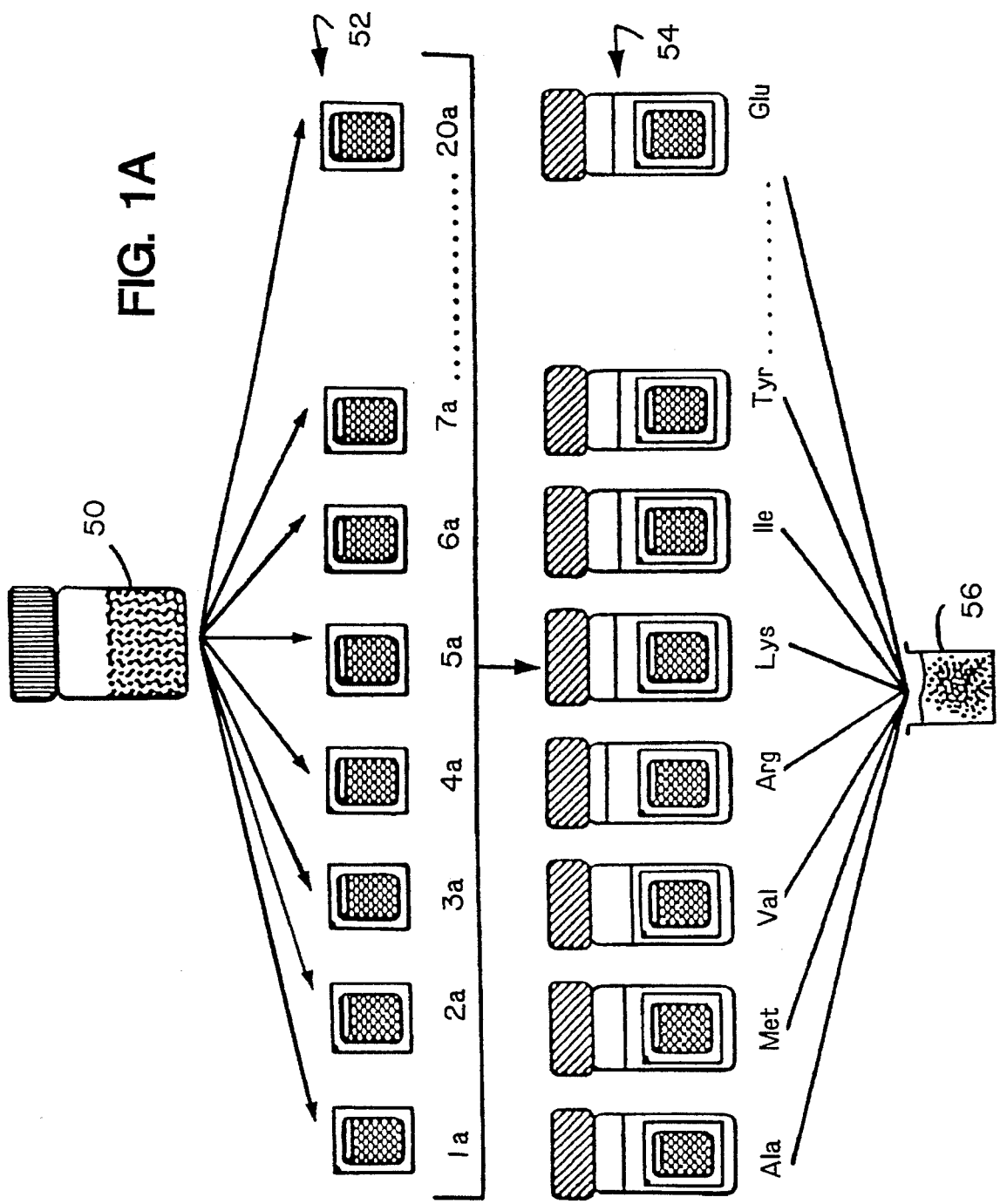
FIG. 1 is a schematic flow chart in two sheets (FIGS. 1A–1B) illustrating a process of this invention in an embodiment in which peptide mixtures are formed from the twenty naturally occurring amino acids.

For instance, one can include one or both isomers of ornithine, norleucine, beta-alanine, hydroxyproline, and the D-stereoisomers of the naturally occurring twenty amino acids. Consequently, as used in the specification and claims herein, the term "amino acid" will, unless otherwise stated, be intended to include not only the naturally occurring L-amino acids but also their D-stereoisomers and the derivatives thereof as well as all other amino acids. The phrase "amino acid derivative", "protected amino acid derivative" or the like is used herein for a protected amino acid added as a reactant, whereas the phrase "amino acid residue", "residue" or the like is used herein for a reacted protected amino acid that is a portion of an oligopeptide chain.

Further, the terms "peptide" and "oligopeptide" are considered to be synonymous (as is commonly recognized) and each term can be used interchangeably as the context requires. The word "polypeptide" is used for chains containing more than ten amino acid residues. All oligopeptide and polypeptide formulas or sequences shown herein are written from left to right and in the direction from amino-terminus to carboxy-terminus.

It will also be understood that a process described herein can be used to form oligomers of a variety of monomeric repeating unit compounds that can be reacted in equimolar quantities in a manner analogous to the formation of oligopeptides from amino acids. For instance, one can form oligosaccharides, oligonucleotides and the like. However, since there are effective alternative processes for formation of oligomeric chains where there are a small number of monomeric compounds (such as the four nucleotides in DNA and RNA), and since the present process is uniquely effective where the number of monomeric compounds is large (such as the amino acids which make up oligopeptides), it is evident that this process is most preferably applicable to the formation of oligopeptides from amino acids. An oligomer is defined herein to contain from two to about ten reacted monomeric repeating unit compounds such as nucleotides, monosaccharides or amino acid residues, as is usually understood in the art.

The abbreviations used herein for derivatives and residues of the twenty natural amino acids are reproduced in the following Table of Correspondence:

TABLE OF CORRESPONDENCE

| Abbreviation | | |
| --- | --- | --- |
| 1-Letter | 3-Letter | Amino Acid |
| Y | Tyr | tyrosine |
| G | Gly | glycine |
| F | Phe | phenylalanine |
| M | Met | methionine |
| A | Ala | alanine |
| S | Ser | serine |
| I | Ile | isoleucine |
| L | Leu | leucine |
| T | Thr | threonine |
| V | Val | valine |
| P | Pro | proline |
| K | Lys | lysine |
| H | His | histidine |
| Q | Gln | glutamine |
| E | Glu | glutamic acid |
| W | Trp | tryptophan |
| R | Arg | arginine |

-continued

TABLE OF CORRESPONDENCE

| Abbreviation | | |
| --- | --- | --- |
| 1-Letter | 3-Letter | Amino Acid |
| D | Asp | aspartic acid |
| N | Asn | asparagine |
| C | Cys | cysteine |
| X | Xaa | another residue |

In addition to the above, usually used abbreviations, three other abbreviations are also frequently used herein.

The word "predetermined" is used in two contexts herein, and has a similar meaning in each context.

A "predetermined" amino acid residue is a single residue whose identity is known or specifically defined, e.g., alanine, glycine, tyrosine, etc., as compared to being a mixture of residues. A "predetermined position" in an oligopeptide mixture chain is a position, from and including the amino-terminal residue as position 1, occupied by a predetermined amino acid residue or of a mixture of residues, and which position is known and specifically identified. One or more residues and positions can be predetermined in an oligopeptide mixture.

Thus, a predetermined amino acid, such as arginine, at a predetermined position of an oligopeptide mixture can be at any of positions 1 through 10 from and including the amino-terminus that is chosen in any given synthesis. An oligopeptide mixture can also have more than one position occupied by the same or different predetermined residue or residues, as well as more than one position occupied by a mixture of the coupled residues.

The letter "O" is used to indicate a predetermined, but unspecified amino acid residue. Subscripted letters "O", e.g., $O_1, O_2, O_3 \ldots O_n$ etc. indicate a predetermined amino acid residue that is the same (specified) and at the same position $(1, 2, 3 \ldots n)$ among a set of oligopeptide mixtures or solid support-coupled oligopeptide mixtures. The use of a formula containing both one or more subscripted O's and one or more unsubscripted O's indicates that the unsubscripted O is predetermined, but unspecified, whereas the subscripted O's are specified and predetermined. Subscripted numbers need not start at the amino-terminus for any given mixture.

The letter "X" is used to indicate that a position in an oligopeptide formula occupied by that letter is an equimolar mixture of each of a plurality of amino acid residues coupled; i.e., preferably ten or more such residues. Subscripted letters "X" indicate that equimolar amounts of different coupled amino acid residues may be present, whereas use of unsubscripted X's indicates that equimolar amounts of the same residues are present at each indicated position.

The letter "B" is used to indicate a particulate solid support used in the syntheses described herein.

Peptides are one of a number of fundamental classes of biologically relevant effector molecules. Acceptor systems for peptides include: antibodies, enzymes, membrane-bound and internal cellular receptors. Biologically important peptides include bradykinin, oxytocin, β-endorphins, insulin, and the like. Drug discovery involving peptides invariably requires the synthesis and testing of hundreds to thousands of analogs of the original biologically active sequences. In order to understand a given peptide's structure activity relationships (SAR), very large numbers of peptide analogs are needed in all of these areas.

The diversity of the combinatorial possibilities of even the 20 natural amino acids makes the before-described synthesis methods sorely limited in the task of screening for optimal peptide antigens, peptide ligands for biologically relevant acceptor systems, enzyme inhibitors, antimicrobials, and the like [i.e., there are 64,000,000 possible six residue peptides ($20^6$) 1,280,000,000 possible seven residue peptides ($20^7$), and the like]. Although the synthetic methods discussed before have greatly facilitated studies with synthetic peptides, and are available commercially either on a custom basis or for use in kit form, they permit only a very small fraction of possible oligopeptides (composed of either natural or unnatural amino acids) to be prepared.

The studies underlying the present invention began with the premise that for a synthetic combinatorial library (complex mixture set of oligomers) approach to be generally useful, the following criteria would have to be met: 1) mixture sets of oligopeptides would have to be generated in which all of the oligopeptides pertinent to the study would be present in equimolar, or approximately equimolar concentrations; 2) screening of the defined repertoire (set) of oligopeptides would be able to be carried out in solution (i.e., not attached to a solid support or as part of a larger protein); 3) minimal manipulation of the oligopeptide(s) mixture set(s) to be studied would be necessary during their synthesis, characterization and use; 4) screening would be able to be carried out at a high enough solution concentration of the necessary synthetic peptide libraries so that it would be possible to reduce the intended very large repertoire of oligopeptides to a small number of selected "enhanced" sequences for further development; 5) large numbers of peptides would have to be readily prepared in the necessary quantities as needed (10–100s of milligrams) with purities as high as existing chemistries permitted in order to further enhance the activity of initial sequences selected; and finally, 6) the results generated from such a synthetic combinatorial library system would have to be readily verifiable in well-defined existing acceptor systems such as those found in antibodies or cellular receptors.

The first two criteria were considered to be the foundation of the present synthetic method and were deemed important to ensure general applicability to normal assay systems without complicated and/or expensive equipment or systems for its implementation. Equimolarity is also needed if, as expected, the activities found would form a hierarchy of activities and, if for practical consideration, one wished to move ahead with only the best, or a few of the best, enhanced sequences initially determined.

Thus, the equimolar amounts of each component making up the repertoire (set) to be studied could be expected to ensure the necessary selectivity of the interactions of the desired oligopeptide in the mixture to be used (i.e., the "needle in the haystack"-finding the correct hexapeptide in the 64,000,000 possible combinations of the 20 natural amino acids would be analogous to finding a single steel needle in 63,999,999 copper needles). As an insight into the extreme selection criterion involved in such a system, it is helpful if one considers that a single six-letter word would have to be readily found in the presence of 63,999,999 other six-letter words (63,999,999 six-letter words would fill approximately 50,000 pages of text of the size found in a usual scientific journal).

A corollary to criterion one is that analytical or other means necessary must be available to ensure that such an equimolar, or close to equimolar, mixture actually exists. This could be determined with amino acid analysis (the average of several analyses with careful controls), sequence analysis, and/or mass spectral analysis.

A different approach was taken, however, which a priori ensured substantial equimolarity. This involved the separation and recombination of oligopeptide-coupled solid supports. This approach entails the coupling to completion of each of the desired protected amino acids (i.e., t-Boc alanine, etc.) with 20 equimolar portions of starting oligopeptide solid support such as a resin. Assurance that the reactions have all been driven to completion (>99.5 percent for each step) is made by standard assay procedures.

The resulting reacted resins are then combined and thoroughly mixed to form a pool, and following their deprotection and neutralization, the resulting pooled mixture is again divided into a number of equal portions. Each of these portions (that contain equimolar amounts of the different starting amino acid residue-coupled resins) is reacted with a single, predetermined amino acid derivative or is again separately coupled to completion with each of the desired protected amino acid derivatives. Where the 20 natural amino acids are used at each of the two coupling steps, this yields 20 different dipeptide-coupled resins for each of the 20 single amino acid resins (400 different dipeptide resins in total). This process is then repeated until the desired length of the mixture of oligopeptide-coupled resins has been obtained.

This method can be used with any number or kind of amino acid without limitation, to generate the exact oligopeptide-coupled resin mixture pool (synthetic combinatorial library) required. After cleavage of the oligopeptide mixture from the solid support, amino acid and sequence analyses can be used to confirm the expected results, but the accuracy of the methods used to prepare the resin mixtures as described herein exceed those of the analysis systems. Thus, the exactitude of physically weighing the resins, mixing them, separating them, and recombining them, along with the assurance of individual amino acid coupling completion by ninhydrin, picric acid or other means, ensures the necessary equimolarity.

In initial preparations, the acetyl group on the N-terminal residue of each component of the combinatorial resin library was radiolabeled with tritium to ensure that complete cleavage of the peptide from its resin had occurred and that all solution concentrations were equal. Following cleavage of a set of exemplary mixtures from their resins, each was extracted until equal solution concentrations were obtained as determined by equal counts per minute (cpm) per milliliter (ml).

Using most or all of the twenty natural amino acids, an initial concern was that the more hydrophobic components of the mixtures would prove highly insoluble. This was not found to be the case due to the mutually self-solvating properties of the different sequences in each mixture set.

Thus, sets of 400 different sets of 6-mer 160,000 equimolar mixtures can be prepared with about ±1 percent accuracy at a concentration of 10 mg/ml in an aqueous medium. The final solutions of cleaved oligopeptides could be used directly in competitive ELISA or growth inhibition assays as described hereinafter.

Criterion three was met in that no manipulation other than extraction and/or lyophilization was necessary prior to use. Criterion four was met for most studies by the ability to work at solution concentrations of each mixture ranging from about 1 to about 100 mg/ml. This permitted the screening of each mixture set in assay systems at concentrations which ensured that a sufficient concentration of every individual oligopeptide was present in each assay.

For example, if the average molecular weight of a hypothetical N-acetyl C-amide hexapeptide (6-mer) oligopeptide mixture set is approximately 785, then a solution of a mixture set of 160,000 oligopeptides at a total final concentration of 1000 mg/liter (1.0 mg/ml) yields a concentration of each oligopeptide in each mixture of about 6 µg/liter (about 7.6 nmoles/liter). These concentrations, without any consideration of potential positional redundancy, ensure that a sufficient concentration of each peptide is present for normal antigen/antibody interactions, receptor/lipid interactions, and enzyme/substrate interactions.

Criterion five was met by combining the above methods with the simultaneous multiple peptide synthesis (SMPS) approach described before. Hundreds to thousands of individual peptides can be readily prepared with this method using any of the currently existing chemistries. A combination of synthetic chemistries [(t-Boc and f-Moc)] permits: 1) the removal of all side chain protecting groups without cleaving the peptides from the resin [Tam's "low" HF method; Tam et al., *J. Am. Chem. Soc.*, 105:6442–6455 (1983)] and 2) complete, or virtually complete, removal of all of the mixtures from the resin by a final high HF treatment [Houghten et al., *Intl. J. Peptide Protein Res.*, 16:311–320 (1980)]. Use of the SMPS method is not necessary herein, but facilitates the syntheses.

Examples of the fine mapping of the determinant regions of mAb's raised against anti-peptide antibodies described hereinafter are useful here to illustrate the development of optimal binding sequences for antibodies, thereby illustrating fulfillment of criterion six.

A primary benefit of this invention is the facilitation of the formation and identification of specific biologically active oligopeptide sequences for pharmaceutical, diagnostic and other uses, particularly those oligopeptide sequences that are of particular efficacy for the therapeutic treatment of target diseases. Once a peptide mixture has been found with the target biologically activity, this mixture set can be resynthesized as a set of mixtures each with more defined sequence positions, and hence less complexity than the original set.

Repeating the assay on this new set of peptide mixtures leads to further sequence definition of the biologically active peptides. Synthesis and assay of a third set of mixtures with sequences designed from the assay data obtained from the second set permits even further sequence definition of the biologically compound. This process can be repeated as necessary until one or more specific peptide sequences have been found for the target biological assay. Consistent with the above, sets of complex mixtures of peptides are highly useful and valuable tools in any regime intended to search for new therapeutic peptide drugs or other applications in which an empirical search for a compound would be employed.

The Process

Broadly, a process of this invention is defined as a process for the synthesis of a complex mixture pool of solid support-coupled monomeric repeating unit compounds, wherein the mixture pool contains an equimolar representation (amount) of the reacted monomeric repeating unit compounds, such as amino acid residues, coupled at that step in the syntheses.

As noted before, the various solid support particles can be utilized enclosed in a porous container. When that is the case, at least coupling reactions are carried out in such containers. However, porous containers need not be used and coupling reactions can be carried out in beakers, flasks, test tubes or the like as are well known.

For simplicity of expression and so that each otherwise similar process need not be detailed, the more generalized synthesis of solid support-coupled oligomer mixtures will be described without use of the preferred porous containers, whereas the synthesis of solid support-coupled oligopeptide mixtures will be described using the preferred porous containers. It is to be understood, however, that any type of oligomer mixture can be prepared using either procedure.

In accordance with this method, (a) a plurality of solid supports is provided, each a solid support comprised of particles linked to reactive functional groups. The functional groups of the solid support react with a functional group of each of the monomeric repeating unit compounds to be reacted. Additionally, the solid support is substantially insoluble in a liquid medium used during the synthesis. The solid support is also substantially inert to (do not react with) the solvents and reagents used during any reaction carried out during synthesis or cleavage of an oligomer mixture. Some swelling of the solid support in solvents is preferred.

(b) A plurality of liquid media is provided, each medium containing a different monomeric repeating unit compound from a plurality of monomeric repeating unit compounds from which the oligomers are to be formed. Each mixture is synthesized from at least three different monomeric repeating units. Preferably, for oligopeptides at least 6, more preferably at least 10, and still more preferably about 15 to about 20 different monomers (amino acid derivatives) are used. Cysteine is often omitted because of its reactivity, and coupling of methionine, tryptophan and histidine can sometimes be difficult. Those amino acid derivatives, and particularly cysteine and tryptophan, are therefore often omitted when mixtures are made. For oligonucleotides, it is preferred to use the usual four, plus inosine in some instances. Any number of oligosaccharides from three upwards can be used.

Each of the monomeric repeating unit compounds has a first reactive functional group that reacts with the reactive functional group of the solid support and a second reactive functional group that is capable of reacting during the reaction of the solid support functional group and the first reactive functional group, but is protected from so reacting by a selectively removable, covalently linked protecting group. The second functional group can thus be said to be temporarily blocked or protected.

For oligopeptide synthesis, it is preferred that the first reactive functional group be the carboxyl group and the second reactive functional group be the α-amino group. In this method of synthesis, the oligopeptide is synthesized from carboxy-terminus to amino-terminus. The reverse synthetic process can also be used, but is not preferred because stereochemical inversion frequently results.

Usual selectively severable protecting groups for second functional groups of such preferred syntheses are t-Boc and f-Moc. Specific selectively severable protecting groups for other amino acid side chain functional groups are discussed hereinafter.

Oligonucleotides are typically synthesized from the 3'- to 5'-position, in which case the 5'-hydroxyl group is the second reactive functional group. Selectively severable 5'-protecting groups such as methoxytrityl are well known in the art as are selectively severable protecting groups for the bases themselves.

Oligosaccharides are typically synthesized starting with the "reducing" end of the oligomer, even though use of a non-reducing sugar at the starting position is contemplated also. Thus, a glycosidic bond is typically formed with the functional groups of the solid support. An acetyl group is typically used as the selectively severable protecting group of the second reactive functional group, the latter being a 3-, 4- or 6-hydroxyl group. Other functionalities, e.g., hydroxyls, or a saccharide repeating unit can be protected with trialkyl or alkylaryl silyl groups or benzyl groups, as is also well known; one or the other of those protecting groups can also be used as a protecting group of a saccharide repeating unit.

(c) Each of the solid supports is placed in a different one of the liquid media and the reactive functional group of each solid support is therein reacted with a first reactive functional group of a monomeric repeating unit compound in that respective medium to couple that monomeric repeating unit compound to the solid support.

(d) Each of the reactions is maintained for a time period and under conditions sufficient for all of the reactive functional groups of the solid support to couple to the monomeric repeating unit compound to form a plurality of monomeric repeating unit-coupled solid supports. Reaction durations and conditions required for each coupling differ for each monomeric repeating unit. Optimal reaction times and conditions are well known, or can be readily determined. Reaction rate is not particularly relevant herein as compared to completeness of reactions, and the latter can be readily assayed. Reaction completeness is usually assisted by use of a large excess of each of the monomeric repeating units.

(e) Each monomeric repeating unit-coupled solid support is removed from its respective liquid medium, and equimolar amounts, usually equal weights, of each of the monomeric repeating unit-coupled solid supports are admixed to form a reaction product pool, wherein equal weights of the formed pool contain the same number of moles of each monomeric repeating unit-coupled solid support.

The pool formed in step (e) is thus known to contain equimolar amounts of the monomeric repeating units utilized to that point. That knowledge of equimolarity is to an accuracy determined to the high accuracy limits of weighing, initial assaying of the amount of linked functional group present, reaction completion, and the homogeneity of physical admixing utilized.

The above mixture pool is useful in a stepwise synthesis for preparing a complex mixture of solid support-coupled oligomers wherein one or more positions of each oligomer of the mixture contains an equimolar representation of reacted monomeric repeating unit compound coupled at each synthesis step. That pool can be used with steps (f)–(k), below, or with steps (l)–(o) hereinafter described in relation to preparation of an oligopeptide with or without enclosure in a porous container. Steps (f)–(k) are most frequently used after steps (a)–(e) with or without enclosure in a porous container.

(f) The reaction product pool is separated into a number of aliquots of equal weight. Each of the aliquots is enclosed in another porous container, where such containers are used.

(g) The protecting groups are selectively removed from the second reactive functional groups of the pool to form a reacted solid support pool having free reactive functional groups. This step is preferably carried out after the pool is formed into aliquots and those aliquots are re-enclosed when using the porous containers, but can be carried out prior to forming the aliquots and without enclosure.

Thus, using the porous containers, the blocking or protecting groups of the second reactive functional group can be selectively removed after the pool is formed and before each reaction product is enclosed in its container, or after the aliquots are enclosed. When porous containers are not used, the protecting groups are removed before or after aliquots are prepared.

(h) Each of the aliquots having free reactive functional groups is placed into one of a number of liquid media, each medium containing a different monomeric repeating unit compound from a plurality of monomeric repeating unit compounds from which the oligomers are to be formed to form a reaction mixture, wherein each of the monomeric repeating unit compounds has a first reactive functional group that reacts in the reaction mixture with the free reactive groups of the aliquot and a second reactive functional group that is capable of reacting during the reaction of the free reactive functional groups of the aliquot, but is protected from so reacting by a selectively removable, covalently linked protecting group.

(i) Each of the reactions is maintained for a time period and under conditions sufficient for all of the free reactive functional groups of the aliquots to react with and couple to the respective monomeric repeating unit compounds to form a number of solid support-coupled repeating unit reaction products.

(j) Each of the solid support-coupled repeating unit reaction products formed is removed, and equimolar amounts of each of those reaction products are admixed to form a reaction product pool. Equal weights of the reaction product pool contain the same number of moles of each reaction product.

(k) Thereafter, steps (f) through (j) are serially repeated zero or more times until a plurality of solid support-coupled reaction products having the desired number of monomeric repeating units is synthesized.

The resulting complex mixture of oligomers formed after zero, one or more times contains an equimolar mixture of the plurality of monomeric repeating unit compounds at every predetermined position in the chain prepared using steps (a)–(k). The equimolarity is only limited by the accuracy in driving the reactions to completion, which typically is 99.5 percent or more, and weighing errors in step (a) and in separating the substantially homogeneously mixed resins into aliquots, which can be done to even greater accuracy with a multigram sample.

In a preferred form, an above process of this invention is defined as a process for the synthesis of a complex mixture pool of solid support-coupled amino acid residues wherein the mixture contains an equimolar representation (amount) of the amino acid residues coupled. As noted before, solid support-coupled oligopeptide mixture syntheses are discussed using the porous containers for simplicity of expression so that each type of synthesis need not be described. According to this process, (a) at least six porous containers, each containing a solid support comprised of particles linked to reactive functional groups are provided. The functional group of the solid support reacts with each amino acid to be reacted. The solid support particles are of a size that is larger than the pores of the container so that the individual solid support particles are maintained within the porous containers. Both the container and solid support are substantially insoluble in and substantially inert to a liquid medium used during the synthesis, as described before.

(b) At least six liquid media are provided, each medium containing a different protected amino acid derivative from a plurality of protected amino acid derivatives from which the oligopeptides are to be formed. Each of the protected amino acid derivatives has a first reactive functional group that reacts with the reactive functional group of the solid support, and a second reactive functional group that is capable of reacting during the reaction of the solid support functional group and the first reactive functional group, but is protected from so reacting by a selectively removable, covalently linked protecting group.

(c) Each of the containers is placed in a different one of the liquid media and the reactive functional groups of each solid support in each container is therein reacted with a first reactive functional group of a protected amino acid derivative in that respective medium to couple that protected amino acid derivative to the solid support.

(d) Each of the reactions is maintained for a time period and under conditions sufficient for all of the reactive functional groups of the solid support to couple to the protected amino acid derivative to form at least six protected amino acid residue-coupled solid supports.

(e) Each protected amino acid residue-coupled solid support is removed from its respective container. Equimolar amounts of the protected amino acid residue-coupled solid supports are admixed to form a reaction product pool, wherein equal weights of the formed pool contain the same number of moles of each protected amino acid residue-coupled solid support.

The above mixture pool is useful in the stepwise synthesis of a complex mixture of solid support-coupled oligopeptides in which each position of each oligopeptide of the coupled mixture contains an equimolar representation of amino acid residues added at each synthesis step. Here, again, the worker using this process will often continue with steps (f)–(k), below. However, in some instances, it can be desired to first follow steps (l)–(o), and then if desired, follow steps (f)–(k).

(f) The reaction product pool is separated into at least six aliquots of equal weight. Each of the aliquots is enclosed in another porous container.

(g) The protecting groups are selectively removed from the second reactive functional groups of the pool to form a reacted product pool having free reactive functional groups. Again, step (g) can precede step (f).

(h) Each of the enclosed aliquots having free reactive functional groups is placed into one of at least six liquid media, each medium containing a different protected amino acid derivative from a plurality of protected amino acid derivatives from which the oligopeptides are to be formed to form a reaction mixture, wherein each of said protected amino acid derivatives has a first reactive functional group that reacts with the free reactive groups of the enclosed reacted product pool aliquots and a second reactive functional group that is capable of reacting during the reaction of the free reactive functional groups of the pool, but is protected from so reacting by a selectively removable, covalently linked protecting group.

(i) Each of the reactions is maintained for a time period and under conditions sufficient for all of the free reactive functional groups of the enclosed reactant product pool aliquots to couple to the protected amino acid derivative to form at least six solid support-coupled protected amino acid residue reaction products.

(j) Each of the at least six reaction products formed in step (i) is removed, and equimolar amounts of each of those reaction products are admixed to form a reaction product pool. Equal weights of the reaction product pool contain the same number of moles of each reaction product.

(k) Thereafter, steps (f) through (j) are serially repeated zero or more times until a plurality of solid support-coupled reaction product oligopeptides having the desired number of amino acid residue repeating units is synthesized.

A complex mixture of solid support-coupled oligomers such as oligopeptides is useful in itself. For example, batches of dipeptide (2-mer) or longer coupled oligopeptides can be sold for others to utilize in syntheses and assays as described herein.

In another embodiment, one or more specific, predetermined monomeric repeating unit compounds is added at one or more specific positions in the oligomeric chain. One or more positions in the chain on either side or both sides of the predetermined monomeric repeating unit compound contains the equimolar mixture of reacted monomeric repeating unit compounds.

More specifically, using the before-described synthesis of an oligopeptide as exemplary, and remembering that enclosure of the solid support is preferred, but not required, (l) each of the protected amino acid derivative-coupled solid supports of step (k) is removed from its respective liquid medium, and container where appropriate. Equimolar amounts of protected amino acid derivative-coupled solid supports are admixed to form a further reaction product pool, wherein equal weights of the reaction product pool contain the same number of moles of each reaction product.

(m) An aliquot of the pool formed in step (l), typically all or a majority of the pool, is enclosed in a further porous container.

(n) The protecting groups are selectively removed from the second reactive functional groups to form a reacted solid support pool having free reactive functional groups. Deprotection can again precede enclosure (when used) of the aliquot, and step (m) is omitted where a porous container is not used.

(o) The pool aliquot (enclosed or not) having free second reactive functional groups is placed into a single liquid medium that contains a single, predetermined protected amino acid derivative to form a reaction mixture in which the free reactive functional groups and single protected amino acid derivative react, the single protected amino acid derivative having a first reactive functional group that reacts with the free reactive groups of the pool aliquot, and a second reactive functional group that is capable of reacting during the reaction of the free reactive functional groups of the pool aliquot, but is protected from so reacting by a selectively removable covalently linked protecting group.

(p) The reaction mixture is maintained for a time period and under conditions sufficient for all of the free reactive functional groups of the pool aliquot to couple with the single protected amino acid derivative and form a solid support-coupled oligopeptide mixture having a single, predetermined amino acid residue in the same position in the oligopeptide chain.

After completion of step (p), one or more further single protected monomeric repeating unit compounds such as a protected amino acid derivative can be added, if desired. In addition, each of the monomeric repeating unit compounds can be separately added and the resulting reaction products pooled as discussed before to form a complex mixture of solid support-coupled oligomer reaction products that contains equimolar amounts of each monomeric repeating unit compound on either side of the single predetermined monomeric repeating unit compound. It is to be understood that the presence of equimolar amounts of each monomeric repeating unit compound or a single, predetermined monomeric repeating unit compound can be varied at any position in the oligomer chain that is desired.

Using an oligopeptide as exemplary, a complex mixture is provided by following steps (a)–(e) that can be represented by the formula X-B, wherein X represents the equimolar mixture of reacted amino acid residues, and B is the solid support. Where steps (f)–(k) are followed, and the number of repeats of steps (f)–(j) carried out in step (k) is zero, an oligopeptide represented by the formula XX-B is formed. Where steps (f)–(j) are repeated once, an oligopeptide represented by the formula XXX-B is formed.

On the other hand, where steps (a)–(e) are followed by steps (l)–(p), a solid support-linked (-coupled) reaction product oligopeptide of the formula OX-B is formed, wherein X and B are as before, and O is the single, predetermined amino acid residue. In this instance, the product formed in step (p) is itself a pool because of the pooling of step (e), and therefore when steps (f)–(k) are followed, with zero repeats of steps (f)–(j), an oligopeptide mixture is synthesized that corresponds to the formula XOX-B.

It is also contemplated herein that one can start with equimolar amounts of one or more predetermined amino acids coupled to the solid support. In this instance, the reactive functional group of the solid support is a free second reactive functional group of an amino acid residue such as an α-amino group. When that is the case, following steps (a)–(e) and steps (f)–(j) once each [zero repeats of steps (f)–(j) in step (k)] the resulting oligopeptide-linked solid support reaction product can be represented by the formula XXO-B. Steps (l)–(p) can then be carried out, or steps (f)–(j) repeated, or both in any order as desired.

It is also contemplated that a set of mixed oligomers such as oligopeptides be produced by following steps (a)–(e) and then (l)–(p). That procedure forms a solid support-coupled product of the formula OX-B. The reaction product of step (p) is itself a pool because of the mixing carried out in step (e), as noted before, so that steps (f)–(j) can be carried out on that product as many times as desired to form a coupled reaction product such as a mixture pool that includes mixed residues at positions 1–4, a specified residue at position 5 and a mixture of residues at position 6.

It will be apparent to a worker skilled in this art that several further permutations and combinations of the before-described reactions can be utilized. Consequently, no further examples will be provided here.

The minimum number of monomeric repeating unit compounds from which an oligomer is formed is three for an oligonucleotide, oligosaccharide, or an oligopeptide, as already noted. For an oligopeptide, each of the twenty naturally occurring L-amino acids can be used as can the corresponding D-amino acids and D- and L-forms of non-natural amino acids such as ornithine, norleucine, hydroxyproline and beta-alanine as well as other $C_4$–$C_6$ amino acids so that use of about 50 different D- and L-protected amino acid derivatives is contemplated. Oligopeptides and oligopeptide mixture pools are contemplated that contain all D-amino acid residues and mixtures of both D- and L-forms.

In preferred practice, an oligomer is coupled to the solid support by a selectively severable covalent bond, such as an ester or an amide bond, an ultimately produced oligomer mixture set is cleaved (separated or severed) from the solid support and recovered.

As noted earlier, a contemplated oligomer contains a chain having two to about ten reacted monomeric repeating units such as amino acid residues or oligosaccharides. More preferably, an oligomer contains a chain of about five to about eight reacted monomeric repeating units, such as amino acid residues. The exemplary oligopeptides discussed in detail hereinafter contain six reacted amino acid residues, and are referred to as 6-mers.

A $C_1$–$C_8$ acyl group is usually bonded to the N-terminus of an oligopeptide used in acceptor binding assays so that an assayed, cleaved oligopeptide is free at the N-terminus of the positive charge a free amino group would provide at near neutral pH values, e.g. about pH 6–8. An acetyl group, a $C_2$ acyl group, is preferred and is often referred to herein as "Ac". Other $C_1$–$C_8$ acyl groups include formyl, propionyl, butyryl, hexanoyl, benzoyl and octanoyl. A $C_1$–$C_8$ acyl group is added by reaction of a corresponding anhydride such as acetic anhydride, acid halide such as octanoyl chloride or by reaction of a suitable activated ester such as N-hydroxysuccinimidyl benzoate.

A $C_1$–$C_8$ acyl group is usually added to a solid support-coupled oligopeptide upon removal of the selectively removable blocking (protecting) group from the second reactive functional group, when that second reactive functional group is an α-amino group. In preferred practice, for oligopeptide syntheses, the second reactive functional group is the N-terminal amino group and the selectively removable protecting group is a t-Boc or f-Moc group, as noted before.

Where an oligopeptide mixture pool is coupled to the solid support by an ester group formed from the C-terminal residue, and a C-terminal amide is desired, the oligopeptide set can be severed from the solid support by aminolysis using ammonia. Cleavage of an ester group-bonded oligopeptide from the solid support using HF results in a C-terminal carboxyl group. Cleavage of an amide-bonded oligopeptide from a benzhydrylamine resin solid support with HF results in the formation of a C-terminal amide group [—C(O)NH$_2$], which also is neutral at near neutral pH values.

Figure 1B:
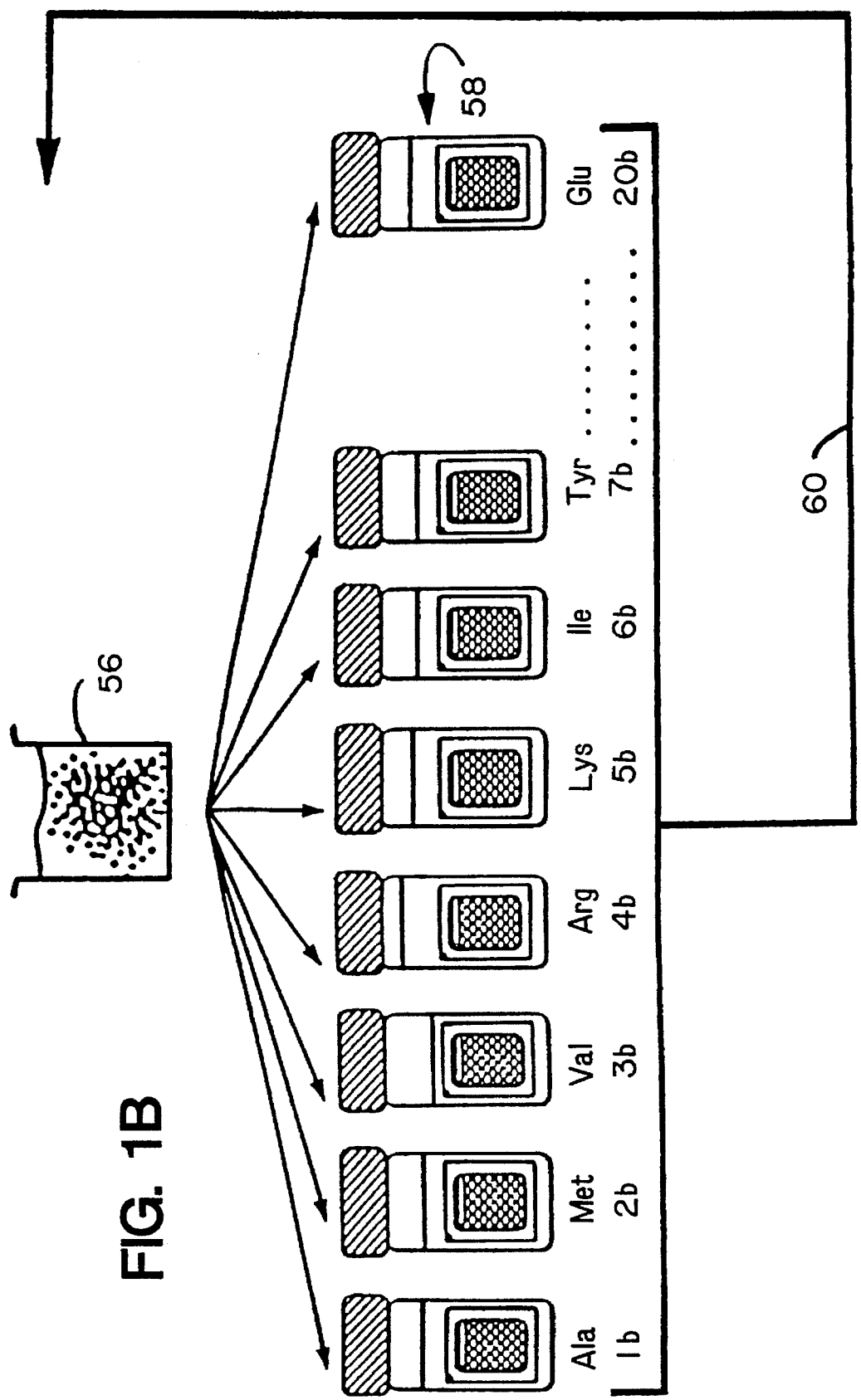

A preferred embodiment of the invention using porous containers to hold the solid support particles is summarized schematically and exemplified in FIG. 1 of the drawings. A solid support comprised of a particle such as a resin linked to reactive functional groups 50 is distributed to a plurality of first porous containers shown in the row designed 52 in equal portions of moles of functional group or equal weight portions when a single homogeneous functional group-linked solid support is used. Preferred porous containers are mesh bags or packets discussed hereinafter.

For this example, it will be presumed that there are twenty porous containers in row 52, each labeled 1a–20a respectively, although all twenty are not shown for purposes of clarity, and one need not use all twenty natural amino acids in any study, or one can use more than twenty when non-natural amino acids are included. Each first container in row 52 is then separately placed in a liquid medium containing a single amino acid derivative with appropriate blocking by a selectively removable protecting group and one free, reactive functional group, e.g. a carboxyl group. Each medium contains a different amino acid derivative, so that each container is reacted with a different protected amino acid derivative, as indicated at row 54. Each protected amino acid derivative is then reactively coupled to its respective resin, with all reactions being maintained under conditions and for a time period sufficient for the reaction to go to completion, so that at the end of the reactions, each first container 1a–20a holds a support resin optimally loaded and completely reacted with a related single amino acid derivative.

The coupling completion can be determined by standard means such as Gisen's picric acid procedure [Gisen, *Anal. Chem. Acta.*, 58:248–249 (1972)], Lebl's bromophenyl blue procedure [Krchnák et al., *Coll. Czech. Chem. Commun.*, 53:2542 (1988)] or by the quantitative ninhydrin test [Savin et al., *Anal. Biochem.*, 117:147–157 (1981)] after removing a small amount of resin from each container. Given the relatively large amount of resin (solid support) used in these reactions, e.g., several grams, removal of milligram amounts of reaction product for assays does not affect equimolarity in the reaction product.

The twenty reacted solid supports, each containing a single reacted amino acid residue, are then removed from the first porous containers 1a–20a and combined in a single vessel 56 (shown in FIG. 1-A and FIG. 1-B for convenience), in which they are thoroughly mixed to form a substantially homogeneous mixture in which the particles of solid support from each of the porous containers $1a$–$20a$ are substantially equally distributed throughout the vessel to form a reaction product pool in which equal weights of the pool contain the same number of moles of each reacted solid support.

This mixture pool is then divided into twenty (or another desired number) equal weight second aliquots and one aliquot is placed (enclosed) in each of twenty second porous containers labelled $1b$–$20b$ shown in row 58, so that each second porous container $1b$–$20b$ now holds reacted solid support particles with all twenty first amino acids equally represented. After suitable amino acid unblocking (deprotection), each of these second porous containers $1b$–$20b$ is placed in a separate liquid medium, each medium again containing only one of the twenty amino acids, also appropriately blocked, and containing a free reactive functional group. Further coupling reactions are run to completion in each medium, so that at the end of the second reaction sequence each second container $1b$–$20b$ contains reacted solid support particles onto which are attached (coupled) twenty 2-mer chains of amino acids; i.e., twenty first amino acids each coupled to the single second amino acid of this second reaction step. Thus, each porous container holds twenty different 2-mer peptides in essentially equimolar quantities, and the twenty bags in total contain 400 different 2-mer peptides.

The procedure is repeated (reacted solid support removal, thorough mixing, unblocking, placement in twenty new porous containers and reaction of each oligopeptide-linked solid support in each porous container in a different medium with each medium having only a single amino acid) as shown by arrow 60 until the desired number n of steps have been accomplished. At the end of each step the number of n-mer chain oligopeptides in each container is $20^{n-1}$, and the total number of n-mer oligopeptides in all twenty containers is $20^n$. Serially repeating the steps of separating-reenclosing, unblocking reaction with another blocked amino acid derivative, reaction maintenance and pooling steps provides a complex mixture of oligopeptides having the desired number of amino acid residues in length, with each amino acid utilized being present in equal molar amounts of each residue at each position in the oligopeptide chain.

These n-mer oligopeptides are cleaved from the resin using various methods such as conventional hydrogen fluoride/anisole procedures; see, e.g., Houghten et al., *Intl. J. Peptide Protein Res.*, 16:311–320 (1980).

To consider a method aspect of the invention in detail, the method is described with respect to protocols and chemistry similar to that of the SMPS process referred to before. It will be understood however, as discussed below, that this description is for example only, and that the process can be suitably carried out using other oligopeptide formation protocols and chemistry, and is not limited only to SMPS-type protocols and chemistry.

Considering then the exemplary embodiment, twenty separate porous synthesis containers are prepared, each containing an equal number of moles of functionalized solid support resin. It is important at this step, as in each of the subsequent subdivision steps, that each aliquot contains the same number of moles of resin functional group or coupled peptide derivative, as is appropriate. Thus, where a single lot of functionalized solid support is used, each aliquot contains an equal weight of solid support. Where different lots of functionalized solid support are used, weights of those different supports used are different among the aliquot, but each aliquot contains an equimolar amount of functional group. Thus, weighings should be done as accurately as reasonably possible.

The resin in each packet is separately reacted with a different one of the twenty naturally occurring amino acids. The coupling of the first blocked amino acids to the respective resins is performed with the carboxyl-terminal end of each first amino acid (a first free reactive functional group) reacting and becoming covalently linked to the support resin and the alpha-amino group (the second reactive functional group capable of reacting during the reaction of the other free reactive functional groups) and reactive side chains of the amino acid blocked.

The coupling reactions are typically driven to completion by adding an excess of the blocked amino acids, and each separate reaction carried out under optimal conditions. It is recognized that each coupling reaction requires different reaction conditions and time to provide full completion. Therefore it is understood that some reactions are completed before others. The earlier-completed reactions can be allowed to sit while the other reactions continue to completion, or, if the reaction products might become degraded, they can be removed from the reaction media and maintained under stabilizing conditions.

After completion of the first amino acid coupling, the resin is removed from each container, pooled together with the resins from all of the other containers and mixed thoroughly (substantially homogeneously). The resin mixture is then separated into twenty aliquots of equal weight. As noted above, at this stage, each weighed aliquot contains a mixture of support resin with an equimolar representation of one of the twenty amino acids coupled to the resin. The twenty weighed aliquot mixtures are then each placed into separate porous second containers. Again each aliquot is reacted with an excess of a different one of the twenty naturally occurring blocked amino acids under conditions that drive the coupling reaction to completion. The blocked second reactive functional group, here the $\alpha$-amino group, can be unblocked before or after pooling, or before or after reenclosure in second containers. Preferably, the protecting group of the second reactive functional group is removed after the reenclosure step.

In one embodiment, the above steps are then repeated for however many cycles are necessary to synthesize the desired length of peptide.

The result can be illustrated by taking three of the samples shown in the Figure as representative for descriptive purposes. Sample $1a$ is first reacted with alanine, and Sample $2a$ is first reacted with methionine, and Sample $3a$ is reacted with threonine, yielding the initial chains of:

$1a$) resin-ala;

$2a$) resin-met; and $3a$) resin-val.

These three are then mixed, divided, e.g., into three aliquots $4b$, $5b$ and $6b$, and separately reacted respectively with, arginine, serine, and lysine, yielding three mixtures of 2-mer peptide chains as follows:

$1b$) resin-ala-arg, resin-met-arg and resin-val-arg;

$2b$) resin-ala-lys, resin-met-lys and resin-val-lys; and $3b$) resin-ala-ser, resin-met-ser and resin-val-ser.

The total number of different oligopeptides will be seen to be $X^n$, where X represents the number of different amino acids in the initial plurality and n is the number of amino acids in each chain. Thus, with the twenty naturally occurring amino acids as the starting plurality, the process results in $20^n$ different peptide sequences. For example, a chain with a length of six amino acid residues results in $20^6$=64,000,000 different oligopeptide sequences.

Mixtures of peptides can be synthesized with mixtures of at least three to all twenty amino acids or to include D-amino acids or L-, D- or symmetric amino acids at all positions in the sequence or, alternatively, with a fixed, single predetermined amino acid at one or more positions and mixtures in the remaining positions in the peptide chain. An example of a mixture of peptides of this latter sort is the 6-mer peptide mixture pool having alanine in position 1 ($O_1$), lysine in position 2 ($O_2$) and mixtures of residues, $X_{3-6}$, at positions 3–6 so that each $X_n$ represents a mixture of amino acid residues used, yielding a mixture set having 160,000 different oligopeptides. The first two amino acids can be synthesized on the resin using prior art methods for single amino acid additions, when synthesized N-terminal to C-terminal, and the remaining four positions are synthesized using the physical mixing process described herein.

Similarly, one could have a mixture set in which a glutamic acid residue occupies position 3 ($O_3$), an arginine residue at position 5 ($O_5$), and mixed residues at positions 1, 2, 4 and 6 ($X_1$, $X_2$, $X_4$ and $X_6$), also containing 160,000 different peptides. The latter peptide mixture set can be synthesized with a combination of the prior art and the present invention methodologies at different positions in the overall chain synthesis. However, each position in any oligomer chain described herein that contains an equimolar mixture of the coupled monomeric repeating unit is made using the pooled physical mixing procedure described herein.

Once one has completed the desired number of repetitions of the present process (e.g., six) one will then be able to readily identify the specific final container in which each particular peptide sequence will be found. That identification is accomplished by removing any remaining protecting groups, cleaving the oligopeptides, isolating the oligopeptide mixtures and removing an aliquot having a desired mixture set of oligopeptide sequences.

Sets of such mixtures can then readily be reacted with a desired acceptor such as a cellular receptor and then assayed for identification of those sequences that react most strongly with the receptor. This assay process can be repeated as many times as desired with different mixture sets to insure that all reasonable candidates for reaction are assayed.

From the identification of the optimum set sequences for reaction and binding, one can develop appropriate peptides and peptide derivatives to be used for the therapeutic treatments of organism dysfunctions that involved that receptor as an acceptor. One can anticipate that a number of pharmaceuticals for the treatment of human, animal and plant diseases can be identified and developed in this manner.

These assay procedures are discussed in greater detail hereinafter.

The value of the method of the present process lies at least in part in the fact that, since this process provides all possible amino acid sequences in the n-mers in equimolar quantities, and since those sequences are automatically divided into small aliquots of known composition, it becomes easy for researchers to quickly and comprehensively react potential peptide candidates in individual aliquots with the acceptor (receptor) of interest and assay those candidates for the optimum reaction materials. This represents a marked advance over prior art processes that either required that vast numbers of peptide candidates be separately assayed (a difficult, costly, and time-consuming undertaking) or that one speculate on which type of amino acid residue sequence might be most likely to work, so that sequences of that type could be individually constructed (also time-consuming, and not necessarily likely to actually produce the optimum materials).

In principle a complex mixture pool of peptides sequences could be synthesized by simply adding a mixture of the blocked derivatives of the twenty naturally occurring amino acids to the coupling steps in the Merrifield peptide synthesis protocol as is described in WO 88/00991. This procedure adds a mixture of amino acid derivatives at any given position in the synthesis of a peptide chain. However, unlike a method of the present invention, the yields of each amino acid residue coupled in a reaction performed in this manner are different under the same reaction conditions, even using different initial amounts of blocked amino acid derivatives, and therefore the ratio of amino acid residues incorporated is non-uniform and non-equimolar.

The concentrations of blocked amino acid derivatives added at a coupling step involved in a peptide mixture synthesis could theoretically be adjusted to compensate for the differences in yields, as reported by Geysen in WO 86/00991. However, this process would be difficult in practice and would result in unequal incorporation of amino acids into the peptide chain. A mixture of peptides of this sort would have over-representation of some sequences and under-representation of others, thereby complicating the result of any assay/search process designed with the premise that all sequences in the mixture were equally abundant.

Alternatively, a mixture of peptides could theoretically be created by synthesis of each chain separately. This solution is impractical, however, in that the number of combinations of sequences for a given chain length is twenty raised to the power of the number of amino acids in the chain (i.e. $20^n$, where n is the number of amino acid residues in the chain). A 4-mer sequence of just four amino acid residues would give rise to 160,000 different peptides in a mixture if all twenty naturally occurring amino acids were present at each position. Similarly, a six amino acid residue random sequence peptide would have 64,000,000 different peptide combinations. Individual syntheses of such numbers of peptide combinations would require an extraordinary amount of synthesis time, running into months and perhaps years.

Equimolar representation of each individual sequence in the above described mixtures formed by the process of this invention is the result of the unique methodology of this process, that allows synthesis of oligopeptides wherein a mixture of amino acids can be reacted at any one position giving an equal yield of addition of each amino acid residue in the resulting oligopeptide chain. Carrying out coupling reactions substantially simultaneously for a plurality of samples also permits the process to be completed in a time period of days or a few weeks, well within the reasonable time frames of both experimental and commercial synthesis schedules.

The containers used for syntheses do not appreciably react chemically with and are substantially insoluble in water, acids such as trifluoroacetic acid and anhydrous hydrogen fluoride, bases such as diisopropylethylamine, and organic solvents such as acetone, benzene, toluene, xylene, ethyl acetate, dimethyl sulfoxide, methylene chloride, chloroform, dimethyl acetamide, N-methyl pyrrolidone, dimethyl formamide and the like. Thus, the container is substantially inert to reaction or dissolution with common laboratory liquids. Suitable containers are preferably prepared from polymerized ethylene, propylene and mixtures thereof. Stainless steel and polytetrafluoroethylene can also be utilized for the container. A container can be in rigid shaped form such as closable cylinders or in flexible form such as the sealable bags used in the SMPS process.

Each container includes a sufficient number of foraminae, pores or openings to permit ready entrance and exit of solvent and solute molecules at the reaction temperature, which is typically that of ambient air in a laboratory. For instance, a container can be prepared from a woven mesh, in which the foraminae are the interstices between the woven fiber. Other suitably inactive perforate or porous materials can also be employed, such as a perforated sheet or a non-woven fabric sheet material, either having equal or unequal foraminae. The container material can be substantially completely foraminous (e.g., being formed substantially entirely from mesh materials) or partially foraminous if desired. Containers can be closed in any suitable manner, such as by sealing with liquid-tight lids, heat sealing, and so forth. Subsequent reopening can be by lid removal, cutting of the sealed container, etc.

The foraminae (pores) are of a size that is smaller than any of the enclosed reactive particles. Exemplary polypropylene mesh is available having in interstices of about 35 to about 100 microns. Stated differently, the mesh foraminae are of a size to retain particles that are retained on a 140–400 standard sieve mesh. More preferably, the foraminae are such that particles retained within the foraminae are those that are retained on a 200–400 standard sieve mesh. The foraminae of the containers are large enough to permit draining of all solvents used during a solid phase synthesis within a time period of about five minutes, and more preferably, within a time period of about three minutes, the draining times being measured at the temperature of the organic reaction.

Exemplary foraminous (porous) containers are further described in U.S. Pat. No. 4,631,211.

A container of a synthesis means of this invention encloses a known quantity of solid phase synthesis particles comprised of one or more constituents that includes a covalently linked reactive functional group or a subunit covalently linked to the particle by a selectively severable bond.

Several solid supports containing covalently linked reactive functionalities have been described in the chemical and biochemical literature, and any such support can be utilized so long as the solid support is insoluble in water, in the before-mentioned organic solvents and is substantially chemically inert to the reaction conditions utilized, as discussed before for the containers. The solid support preferably swells in the solvents utilized during the synthesis due to physical, rather than chemical processes.

The solid supports typically fall into one of three general types, each of which is discussed below.

Perhaps the most utilized particles for oligopeptide and oligo- and polynucleotide syntheses are polymerized resins. The polymerized resins are generally in the form of porous beads.

Of the resins, the hydrophobic polymerized styrene cross-linked with divinyl benzene (typically at about 0.5 to about 2 weight percent) resins are the most often utilized, especially for oligopeptide syntheses. The resin beads so prepared are further reacted to provide a known quantity of a benzyl moiety as a portion of the polymerized resin. The benzyl moiety contains a reactive functional group through which the subunits of the sequence to be synthesized may be covalently linked by a selectively severable bond. Although the reactive benzyl moieties are typically added after the resin bead has been synthesized by reaction of a polymerized styrene moiety, such resins are herein generally described as polymerized styrene cross-linked with divinyl benzene and including a known amount of polymerized vinyl benzyl moiety.

The reactive functionality of the benzyl moiety is typically selected from the group consisting of aminobenzyl and halobenzyl such as chlorobenzyl. Polymerized, cross-linked styrene resins containing chlorobenzyl moieties are sometimes referred to in the art as chloromethyl styrene resins, while resins containing aminobenzyl moieties are sometimes referred to as amino-styrene or aminomethyl-styrene resins.

It is noted that the subunit/particle link formed between a particle containing aminobenzyl moiety and a carboxylic acid is not readily cleavable under usual conditions of synthesis. As a consequence, such particles are used with sever able linking groups between the particle and first linked subunit, where a free subunit reaction product is desired to be recovered.

Additional useful resin particles are those materials referred to by East et al., *J. Immunol.*, 17:519–525 (1980) as macroreticular resins. Those resins are said to be prepared from cross-linked polystyrene and to include a reactive aminobenzyl moiety. The described resin particles contain pores of a large enough cross-section to permit entry of antibodies and immunoreaction of those antibodies with the synthesized oligopeptide. The macroreticular resins were reported to be obtained from Rohm & Haas under the trademark designation XE-225A.

Resins containing a known amount of chlorobenzyl moieties may be purchased from Sigma Chemical Co., St. Louis, Mo. under the trademark names Merrifield's peptide Resin (chloromethylated copolystyrene divinylbenzene). Such materials are typically supplied containing about 0.1 to about 2 milliequivalents of chlorine per gram of particle.

The aminobenzyl group can be prepared from polymerized styrene cross-linked with divinyl benzene by reaction with N-(hydroxymethyl)phthalimide under Friedel-Crafts conditions followed by hydrazinolysis of the phthalimide group as is described by Kent et al., *Israel J. Chem.*, 17:243–247 (1978). Particles containing reactive aminobenzyl moieties are also commercially available from Pierce Chemical Company of Rockford Ill. and are reported to contain about 0.3 to about 0.7 millimoles of aminobenzyl moiety per gram of particles.

Intermediate linking groups between the reactive benzyl moiety and the first of a sequence of subunits may also be employed as is the case of the 4-(oxymethyl) phenylacetyl group bonded to an amino benzyl moiety reported by Kent et al., above. Another linking group is the 4-(oxymethyl)phenoxy group bonded to a benzyl moiety as reported by Meienhofer et al., *Int. J. Peptide Protein Res.*, 13:35–42 (1979).

The above-described polystyrene-based particles are frequently used in the synthesis of oligopeptides in which the carboxyl-terminal amino acid residue (subunit) is bonded through a selectively severable covalent bond to the polymerized, reactive vinyl benzyl moiety of the resin. Benzyl ester bonds between the polystyrene-based particle and subunit are stable in the presence of relatively mild acids, but sever when treated with strong acids such as hydrofluoric acid or a mixture of acetic and hydrobromic acids. Oligopeptide syntheses are typically carried out using mild acid-sensitive protecting groups on the alpha amino groups such as N-tert-butoxycarbonyl (t-Boc) or 9-fluorenylmethyloxycarbonyl (f-Moc), while using other, strong acid-sensitive protecting groups on reactive side chains. The photosensitive nitroveratryloxycarbonyl (NVOC) amino-protecting group can also be used.

One of the difficulties in working with large quantities of synthetically prepared oligopeptides relates to the usual practice of using anhydrous hydrogen fluoride (HF) to sever the synthesized oligopeptide reaction product and its side chain protecting groups from the solid support. Hydrogen fluoride is not an easy material to work with and must be handled with great care. In addition, since HF severs both the oligopeptide from the particle and side chain protecting groups from the oligopeptide, the severed oligopeptide must be purified from the side chain protecting groups.

A disulfide-containing linking group that can be bonded to a benzylamine of a before-described resin particle may be utilized to alleviate some of the difficulties encountered in using HF to sever the oligopeptide reaction product and to remove side chain protecting groups. A precursor to that linking group is represented by the formula:

$$\text{t-Boc-NHCH}_2\text{CH}_2\text{SSCH}_2(\text{CH}_2)_x\text{CO}_2\text{H}$$

wherein t-Boc is tert-butoxycarbonyl, and x is a numeral having the value of zero or one, such that when x is zero, the parenthesized $CH_2$ group is absent.

The carboxyl group of the linking group is bonded to the amino group of a polymerized vinyl benzyl moiety of a reactive resin-containing particle using standard peptide amide bond-forming techniques such as via the anhydride, with dicyclohexylcarbodiimide or another carbodiimide. The t-Boc group is thereafter removed using mild acid as is well known, the resulting ammonium salt is neutralized to provide a free primary amine and the resulting free primary amine-containing particles are rinsed to remove any excess base-containing reagent used in the neutralization step.

The first amino acid subunit is thereafter coupled through its carboxylic acid group to the free primary amine to form a particle-linked subunit. The amino acid residue is linked to the resin through an amide bond between the carboxyl group of the amino acid and the amino group of the disulfide-containing linking group that is itself bonded by an amide bond to the polymerized vinyl benzyl moiety of the resin. The resulting linking group, written in the direction from left to right and from the amino acid residue toward the benzyl moiety, is represented by the formula:

$$-\text{NHCH}_2\text{CH}_2\text{SSCH}_2(\text{CH}_2)_x\text{CONH}-$$

where x is as before-described.

The linking group with any amino acid that may be designated "Z" coupled through its carboxyl group and with the particle bonded through its polymerized vinyl benzyl moiety may be written as described above:

$$\text{Z-NHCH}_2\text{CH}_2\text{SSCH}_2(\text{CH}_2)_x\text{CONH-Particle.}$$

A particular benefit of using the above-described linking group is that its amide and disulfide bonds are stable to contact with HF and other strong acids used to selectively remove amino acid side chains. Consequently, such acids can be used to remove the side chains of the oligopeptide reaction product while that reaction product is still linked to the resin particle. That selective removal permits the removed side chain protecting groups to be rinsed away from the reaction product-linked resin particle and thereby provides easier purification of the oligopeptide reaction product.

The oligopeptide-linked resin particle is thereafter contacted with a disulfide bond-breaking agent to selectively sever the oligopeptide reaction product from the resin particle. The severed oligopeptide reaction product can thereafter be recovered in relatively pure form using standard procedures such as extraction of the severed reaction product/particle mixture formed with an aqueous composition containing 5 percent acetic acid. The extracted composition can thereafter be lyophilized to provide the reaction product.

The reaction product can also be further purified as is known prior to its ultimate recovery.

Several reagents are well known to be useful for breaking the disulfide bond. Exemplary reagents include sodium borohydride, 2-mercaptoethanol, 2-mercaptoethylamine, dithiothreitol and dithioerythritol. Mercaptan-containing carboxylic acids having two to three carbon atoms and their alkali metal and ammonium salts are also useful. Those reagents include thioglycolic acid, thiolactic acid and 3-mercaptopropionic acid. Exemplary salts include sodium thioglycolate, potassium thiolactate, ammonium 3-mercaptopropionate and (2-hydroxyethyl)ammonium thioglycolate.

The disulfide-containing t-Boc-protected linking group precursor may be prepared by standard techniques. For example 2-aminoethyl disulfide may be reacted with two moles of 2-(tert-butoxycarbonyloxylmino)-2-phenylacetonitrile or N-(tert-butoxycarbonyloxy)-phthalimide or a similar reagent to form bis-N-t-Boc-2-aminoethyl disulfide. That disulfide can then be reacted with thioglycolic acid or 3-mercaptopropionic acid to form the precursor shown above.

A relatively newer group of resin particles has been reported by E. Atherton and co-workers. Those particles are based upon copolymers of dimethyacrylamide cross-linked with N,N'-bisacryloylethylenediamine, including a known amount of N-tert-butoxycarbonyl-beta-alanyl-N'-acryloylhexamethylenediamine. Several spacer molecules are typically added via the beta-alanyl group, followed thereafter by the amino acid residue subunits. See Atherton et al., *J. Am Chem. Soc.*, 97:6584–6585 (1975).

The β-alanyl-containing monomer can be replaced with an acryloyl sarcosine monomer during polymerization to form resin beads. The polymerization is followed by reaction of the beads with ethylenediamine to form resin particles that contain primary amines as the covalently linked functionality. See Atherton et al., *Bioorga. Chem.*, 8:351–370 (1979) and Atherton et al., *J.C.S. Perkin I*, 538–546 (1981).

The polyacrylamide-based resin particles are relatively more hydrophilic than are the polystyrene resin particles and are usually used with polar parotic solvents. Exemplary solvents include dimethylformamide, dimethylacetamide, N-methylpyrollidone and the like.

The base-sensitive α-amino protecting group N-9-fluorenylmethyloxycarbonyl can be used in conjunction with the polymerized dimethylacrylimide-based resins. See Atherton et al., *J.C.S. Perkin I*, 538–546 (1981) and Meienhofer et al., *Intl. J. Peptide Protein Res.*, 13:35–42 (1979).

A second group of solid supports is based on silica-containing particles such as porous glass beads and silica gel. For example, Parr and Grohmann, *Angew. Chem. Internal. Ed.*, 11, 314–315 (1972) reported on the use of the reaction product of trichloro-[3-(4-chloromethyl)phenyl] propylsilane and porous glass beads (sold under the trademark PORASIL E by Waters Associates, Framingham, Mass.) as solid support for oligopeptide syntheses. Similarly, a mono ester of 1,4-dihydroxylmethylbenzene and a silica (sold under the trademark BIOPAK by Waters Associates) was reported to be a useful solid support for oligopeptides syntheses by Bayer and Jung, *Tetrahedron Lett.*, 4503–4505 (1970). Each of the above solid supports is seen to utilize a reactive benzyl moiety through which the subunit was bonded to the particle.

The third general type of useful solid support may be termed "composites" in that they are constituted by two major ingredients, a resin and another material that is also substantially inert to the organic synthesis reaction conditions employed.

One exemplary composite described by Scott et al., *J. Chrom. Sci.*, 9:577–591 (1971), utilized glass particles coated with hydrophobic, polymerized, cross-linked styrene containing reactive chloromethyl groups. Another exemplary composite was reported to contain a core of fluorinated ethylene polymer onto which was grafted linear polystyrene. See Kent et al., above, and van Rietschoten, in *Peptides 1974*, Y. Wolman ed., 113–116 (1975).

Similar solid supports are also reported for synthesis of oligo- and polynucleotides. For example, Letsinger et al., *J. Am. Chem. Soc.*, 87:3526 (1965) reported on the use of a so-called "popcorn" cross-linked styrene copolymer; Duckworth et al., *Nucleic Acids Res.*, 9:1691–1706 (1981) reported on the use of succinylated amine-containing polydimethylacryl-amide-based resins; Protapov et al.. *Nucleic Acids Res.*, 6:2041–2056 (1979) reported on the use of a composite solid support based on a polytetrafluoroethylene core containing grafted polystyrene; and Matteucci et al., *J. Am. Chem. Soc.*, 103:3185–3190 (1991) reported the use of macroporous silica gel reacted with (3-aminopropyl)triethoxysilane.

General reviews of useful solid supports (particles) that include a covalently linked reactive functionality may be found in Atherton et al., *Perspectives in Peptide Chemistry*, Karger, 101–117 (1981); Amarnath et al., *Chem. Rev.*, 77:183–217 (1977); and Fridkin, *The Peptides, Volume* 2, Chapter 3, Academic Press, Inc., (1979), pp. 333–363.

A porous container can also be provided that encloses a known amount of particles having a known amount of monomeric repeating units linked thereto by selectively severable covalent bonds. Each of such repeating units, e.g., amino acid residues, that is farthest from (distal to) the particle/repeating unit link contains a functional group capable of reacting during the organic synthesis but that is protected from so reacting by a selectively removable, covalently linked protecting group.

Illustratively, 5'-O-methoxytrityl-protected nucleosides linked to particles by 3'-O-succinyl linkages are commercially available, wherein the succinyl linking groups are also bonded to (a) 20–60 micron silica particles by (3-aminopropyl)diethoxy siloxane groups; (b) supports of polymerized styrene cross-linked with either 1–2 percent divinyl benzene that include polymerized vinyl aminobenzyl moieties (also referred to as amino-polystyrene), and (c) 10 percent cross-linked polydimethyl acrylamide-based resins that include glycylethylene-diamino linkages (also referred to as amino-polydimethyl-acrylamide). The nucleosides of such particles also typically include appropriate protecting groups for the ring substituents such as N-benzyl and N-isobutyl protecting groups, as are well known.

Particle-linked, selectively severable monomeric repeating units that themselves contain protected reactive functional groups are provided in known amounts linked to the particles by the manufacturer. For example, protected, nucleoside-containing particles are available prepared from a resin similar to the before described succinylated amino-polystyrene resin and containing 0.1–0.2 millimoles of nucleoside per gram of particle.

Similarly, resin particles of polymerized styrene cross-linked with divinylbenzene and including a known amount of polymerized vinylbenzyl moiety that contain linked amino acid residues having protected reactive functionalities such as N-t-butoxycarbonyl-protected α-amino (t-Boc-protected) groups are provided by several suppliers. Each particulate material is supplied with a statement as to the amount of linked amino acid residue present in the particles.

This invention also contemplates use of individual containers enclosing particles that contain identical sequences of two or more reacted monomeric repeating units (reaction products) that are linked to functional groups of the particles by one selectively severable covalent bond per sequence. Such particles thus contain a reacted monomer that is linked to the particle; i.e., that is proximal to the particle, and a monomer that is farthest from the particle; i.e., that is distal to the particle. Since both single monomers linked to the particles and monomer-containing reaction product sequences linked to the particles contain distal monomers, both types of particles (e.g., amino acid-linked) are usually referred to herein as monomer-linked particles, and the monomeric repeating units and reaction product sequences are usually referred to as particle-linked monomers.

Support-Coupled Oligopeptide Mixtures

A solid support-coupled complex mixture pool of oligopeptides prepared by a before-described synthesis procedure is also contemplated. Such a mixture consists essentially of pool of solid support particles coupled by a selectively severable covalent bond to linear oligopeptide molecules. Each of the linear oligopeptide molecules contains a chain having the same number of amino acid residues. The coupled oligopeptide mixture has at least one, same, predetermined position of each chain occupied by a different one of a plurality of amino acid residues so that the coupled oligopeptide mixture pool contains an equimolar amount of each of the plurality of amino acid residues at the at least one, same predetermined position.

Because an oligopeptide must contain at least two amino acid residues, the at least one other position of the oligopeptide chain can contain a pooled mixture of residues or can be a single residue. Exemplary coupled dipeptide mixtures can be exemplified by the formulas: OX-B, XO-B and XX-B, using the previous definitions for X, O and B.

In preferred practice, the equimolar amounts of at least six different amino acid residues are present at one, two, three, four or five of the same, predetermined positions of each 6-mer chain. Those same, predetermined positions of each 6-mer chain that are occupied by occupied by equimolar amounts of each residue utilized are more preferably at terminal positions of the oligopeptide chains and include the terminal residue. More preferably still, the terminal position selected is the carboxy-terminal position, and since an oligopeptide is preferably stepwise synthesized from the carboxy-terminus to the amino-terminus, exemplary still more preferred coupled complex equimolar mixtures of oligopeptides can be five, four, three or two residues in length and contain equimolar residue mixtures at all five, four, three or two positions, respectively, from the amino-terminus of the 6-mer. An exemplary coupled dipeptide can also include a predetermined residue at position 1 and a mixture at position 2, and have the formula $O_1X$-B.

Coupled complex mixture pools of oligopeptides such as those exemplified immediately above are particularly useful for sale to others to carry out a stepwise synthesis and assay as described herein.

It is still more preferred that a before-described coupled mixture further include one or more same, single, predetermined (specifically defined) amino acid residues at one or more same, predetermined (specifically defined) positions in each oligopeptide chain. Those one or more same, predetermined amino acid residues are preferably at an amino-terminal position of the chain, including the amino-terminal residue.

Thus, keeping the above preference for the positions having equimolar amounts of each of a plurality of amino acid residues in mind, exemplary most preferred coupled mixtures of 6-mer oligopeptides include those having positions 1–5 predetermined, and position 6 as an equimolar mixture; positions 1–4 predetermined, and positions 5 and 6 as equimolar mixtures; positions 1–3 predetermined, and positions 4–6 as mixtures; positions 1 and 2 predetermined, and positions 3–6 as equimolar mixtures; and position 1 predetermined, and positions 2–5 as equimolar mixtures, with the predetermined residues being the same and at the same relative position in each mixture. These five complex oligopeptide mixture pools illustrate the reaction products obtained from the above only X-containing coupled mixture pools when predetermined, single residues are coupled at the same positions to each pool.

Each of the before-described coupled mixture pools of oligopeptides preferably includes the selectively removable protecting group of the second reactive functional group of the last coupled residue. The presence of that protecting group and any other protecting groups on amino acid residue side chains helps permit sale of the coupled mixtures with little fear of degradation prior to ultimate use.

Oligopeptide Sets

A before-described complex mixture pool of solid support-coupled oligopeptides once cleaved or severed from the solid support is referred to herein as an oligopeptide set, an oligopeptide mixture set, by a similar phrase, or more simply as a "set", as well as being sometimes referred to herein as a synthetic combinatorial library. Being severed from the solid support, an oligopeptide set is unsupported, and because of its method of synthesis, such a set is linear.

An oligopeptide mixture set consists essentially of a mixture of equimolar amounts of oligopeptide chains that contain the same number of amino acid residues in each chain; i.e., have the same chain length, preferably 5–10 residues, and more preferably 5–8 residues. The members of a set have one or more single, predetermined (specifically defined) amino acid residues at the same one or more predetermined (specifically defined) positions of the oligopeptide chain and equimolar amounts of at least six different amino acid residues, at one or more predetermined (specifically defined) other positions of the chain. When more than one predetermined amino acid residue is present at more than one predetermined position of the chain, those residues can be the same of different.

When designed for carrying out binding assays as illustrated hereinafter, a preferred oligopeptide mixture set contains the one or more predetermined residues at one or more predetermined positions that include a chain terminus, most preferably the N-terminus. A set preferably includes the equimolar amount of at least six different amino acid residues at one or more predetermined chain positions, and more preferably those chain positions are adjacent to one another. In particularly preferred practice, those adjacent positions are at a terminus of the oligopeptide chain, and most preferably, that terminus is the C-terminus. Preferably, the same mixture of residues is present at each predetermined position.

More preferably, the N-terminal two residues are single predetermined residues within the set. Still more preferably, the N-terminal three residues are predetermined, and most preferably, the N-terminal four residues are predetermined. Thus, in most preferred practice for this use, one or more predetermined chain positions at the N-terminus are occupied by predetermined residues and one or more chain positions at the C-terminus are occupied by an equimolar mixture of residues.

A most preferred oligopeptide mixture set for such an assay contains equimolar amounts of at least six different amino acid residues at the carboxy-terminal 1, 2, 3, 4 or 5 positions of the oligopeptide chain (i.e., positions 2, 3, 4, 5 and 6 from the amino-terminus of a 6-mer), as specifically defined position(s). At least one other position and preferably more than one other position of the chain of such a most preferred oligopeptide mixture set is occupied by a single, predetermined amino acid residue whose identity is the same at an analogous position within the chain for each set, and those single, predetermined amino acid residues are most preferably at an amino-terminal position of the chain, including the amino-terminus of the chain. It is to be understood that although the identity of each single, predetermined residue at a given position in the chain is the same within each set, each such chain position can be occupied by the same or a different residue as between sets.

Exemplary oligopeptide equimolar mixture-containing sets include a dipeptide having one position predetermined and the other a mixture; a tripeptide having two positions occupied by predetermined residues and the other a mixture, or vice versa; a tetrapeptide having one predetermined position, e.g. position 1, and three mixture positions; a 5-mer whose first position is defined (predetermined) and whose remaining positions are occupied by mixtures; a 5-mer whose first and fourth positions are defined and whose second, third and fourth positions are occupied by mixtures; a 6-mer whose first two positions are predetermined and whose last four are occupied by mixtures; a 7-mer whose first position and positions 4–7 are mixtures and whose second and third positions are predetermined; a 7-mer whose first, third and fourth positions are predetermined and whose remaining positions are mixtures; an 8-mer whose third and fourth positions are predetermined and whose remaining positions are occupied by mixtures of residues; an 8-mer whose first four positions are predetermined and whose last four positions are each mixtures; a 9-mer whose fourth and fifth positions are predetermined, and whose remaining positions are mixtures; a 10-mer whose positions 3–7 are predetermined, and whose remaining positions are occupied by mixtures; a 10-mer whose first position is predetermined, with the remaining positions occupied by mixtures; a 10-mer whose positions 7–9 are predetermined, with the remaining positions occupied by mixtures and the like where each mixture is an equimolar mixture of a plurality of coupled amino acid residues that includes at least three, preferably at least 10, and more preferably about 15 to about 20, different amino acid residues as discussed previously.

As noted earlier, it is preferred to use oligopeptide chain sequences of about 5 to about 8 residues in length, with 6-mer sequences being particularly preferred herein, especially where an antibody-binding epitope is sought to be prepared because six residues is the usual length of a linear epitope.

Oligopeptide mixture sets that contain two chain positions of predetermined amino acid residues and four or more positions of equimolar mixtures along the chain are among those preferred. For 6-mers, those sets have the configurations of predetermined, single amino acid and equimolar mixtures shown below:

| Predetermined Positions | Mixture Positions |
| --- | --- |
| 1,2 | 3–6 |
| 2,3 | 1,4–6 |
| 3,4 | 1,2,5,6 |
| 4,5 | 1–3,6 |
| 5,6 | 1–4 |
| 1,3 | 2,4–6 |
| 1,4 | 2,3,5,6 |
| 1,5 | 2–4,6 |
| 1,6 | 2–5 |
| 2,4 | 1,3,5,6 |
| 2,5 | 1,3,4,6 |
| 2,6 | 1,3–5 |
| 3,5 | 1,2,4,6 |
| 3,6 | 1,2,4,5 |
| 4,6 | 1–3,5 |

Each of those positional configurations defines 400 mixture sets when the twenty natural amino acids are used. It is preferred that the predetermined residues, O, be adjacent to each other in the chain.

Oligopeptide mixture sets containing three predetermined positions along the chain and three or more equimolar mixture positions are also preferred. Six-mer sets for those preferred sets have the configurations of predetermined, single amino acid and mixtures shown below:

| Predetermined Positions | Mixture Positions |
| --- | --- |
| 1–3 | 4–6 |
| 2–4 | 1,5,6 |
| 3–5 | 1,2,6 |
| 4–6 | 1–3 |
| 1,2,4 | 3,5,6 |
| 1,2,5 | 2,3,6 |
| 1,2,6 | 3–5 |
| 1,3,4 | 2,5,6 |
| 1,4,5 | 2,3,6 |
| 1,5,6 | 2–3 |
| 1,3,5 | 2,4,6 |
| 1,3,6 | 2,4,5 |
| 2,3,5 | 1,4,6 |
| 2,3,6 | 1,4,5 |
| 3,5,6 | 1,2,4 |

Each of the above positional configurations defines 8000 oligopeptide mixture sets when the twenty natural amino acid residues occupy a predetermined position in the chain. It is preferred that the three predetermined positions be adjacent in the chain.

Hexapeptide oligopeptide mixture sets of the following type are particularly preferred for antibody or other receptor binding studies because of their relative ease in synthesis. Those mixture sets have amino-terminal positions that are occupied by predetermined residues and carboxy-terminal positions occupied by equimolar mixtures of residues, and include sets having one, two, three, four and five predetermined positions.

Thus, using the twenty natural amino acids as exemplary, a 6-mer mixture set having only the first position occupied by a predetermined residue would have twenty member sets each of which contained 3.2 million member oligopeptides. A set having the first two positions occupied by predetermined residues would include 400 member sets each of which included 160,000 member oligopeptides.

The exemplary 400 mixture sets 6-mer oligopeptides are particularly useful in binding assays as a starting group for determining the sequence of a donor that binds to an acceptor of choice, as is illustrated hereinafter.

After carrying out binding studies using the above 400 sets, one can determine one or more sets that exhibit optimal (best) binding. A further group of twenty sets is then synthesized that includes the optimal binding first two residues, twenty single residues at position 3, and equimolar mixtures at positions 4–6. A further binding study is carried out and optimal binding determined for that set. This procedure is then continued until the sequence of an optimal binding donor oligopeptide is determined.

Also preferred because of their relative ease of synthesis and the solubility provided by the C-terminal mixtures are oligopeptide mixture sets 5–10 residues in length whose C-terminal four positions are occupied by amino acid residue mixtures, and whose amino-terminal positions are occupied by predetermined residues. Each above set can be prepared from a single preparation of solid support-coupled 4-mer oligopeptide mixtures to which one or more predetermined acid residues is coupled following each acceptor binding assay.

For example, starting with a batch of support-coupled 4-mer whose positions are all equimolar mixtures, a set of twenty mixtures can be prepared by separately coupling each of the twenty natural amino acids to a separate portion of the batch. After cleavage, a binding assay is run as with a monoclonal antibody to determine best binding. Another set of twenty is then prepared using the same batch with the best binding residue at position 2 in the sequence and each of the twenty residues at position 1. The binding assay is run again and best binding is determined. This process is continued until a predetermined oligopeptide sequence of desired length is completed.

For other types of assays, again using 6-mers as exemplary, it is preferred to use mixture sets having a single predetermined residue at the same position in the chain, with the other positions in the oligopeptide chain being occupied by equimolar amounts of each of the amino acid derivatives utilized. Exemplary 6-mer sets are therefore six in number and each set has position 1, 2, 3, 4, 5 or 6 defined, with the other positions being occupied by equimolar mixtures. Using one of the twenty natural amino acids for each predetermined position provides twenty mixture sets at each position. Inasmuch as there are six such sets, a total of 120 sets are contemplated.

Optimal acceptor binding studies can be carried out for each of the sets that varies at each position of the oligopeptide chain. Where the above 6-mers are used, with each of the twenty natural amino acids at each predetermined position "O" in the chain, 120 assays are required. The residue, "O", of the twenty present that exhibits optimal (best) binding at each position of the chain in those assays defines the residue at that position of an optimal oligopeptide donor. The sequence of an optimal binding donor is then determined from the optimal binding results obtained for each sequence position along the oligopeptide mixture set chain.

It is preferred that one or both termini of an oligopeptide mixture pool set have amide bonds. To that end, it is preferred that the second reactive functional group of the last added protected amino acid derivative be removed while the complex mixture pool is coupled to the solid support and that the resulting free reactive functional group be reacted to form amide bonds on all of the coupled oligopeptides. A before-described $C_1$–$C_8$ acyl group such as an acetyl group is preferably used to form the amide bond at the N-terminus. An amide bond can also be formed when a carboxyl group is the second reactive functional group, or the first reactive functional group, as discussed previously. Each oligopeptide mixture set is preferably prepared and used an as a N-acetyl C-amide derivative mixture set, and can be represented as Ac-sequence-$NH_2$.

It can also be useful for an oligopeptide mixture set to include a label. A radioactive label such as $^3$H can be used as part of an N-terminal acyl group such as an acetyl group.

Other contemplated labels include chromophores such as the 2,4-dinitrophenyl or 4-nitrophenyl groups and fluorescent molecules such as a dansyl group that can be coupled to an N-terminal amino group using dansyl chloride (5-dimethylamino-1-naphthalenesulfonyl chloride) after cleavage of the terminal blocking group.

A 2,4-dinitrophenyl or 4-nitrophenyl group can be coupled to a deprotected terminal amine of a solid support-bound oligopeptide mixture by means of an appropriate halogen derivative such as a chloro or fluoro group. The resulting nitrophenyl aniline derivatives have a yellow to yellow/orange color that can be readily observed.

It is also contemplated that a photoreactive label be coupled to an oligopeptide mixture set, particularly at the N-terminus. Exemplary photoreactive labels include the 4-azidobenzoyl and 4-azidosalicyl groups that are present as N-terminal amides prepared by reaction of the N-hydroxysuccinimide ester of either group with the free, N-terminal amino group. Each of the esters is available from Sigma Chemical Co., St. Louis, Mo.

It should be apparent from the foregoing discussion that a plurality or set of oligopeptide mixture sets is also contemplated. Each set of the plurality has the same sequence of one or more predetermined amino acid residues at one or more predetermined positions of the oligopeptide chain and the same sequence of equimolar amounts of at least six different amino acid residues at one or more predetermined positions in the oligopeptide chain. The sets of oligopeptide sets differ in that at least one predetermined residue present at a predetermined position within each set is different between the sets.

Exemplary sets of sets are the previously discussed 400 sets (twenty sets of 20 each) whose first two positions are occupied by one of the twenty naturally occurring amino acid residues, and the remaining positions 3–6 are occupied by mixtures. Each member of those 400 sets has two predetermined amino acids ($O_1$ and $O_2$) at one or more predetermined positions (the amino-terminal first two positions) and equimolar amounts of the at least six different residues at one or more predetermined positions (the four carboxy-terminal positions).

Another exemplary 6-mer set of oligopeptide mixture sets begins $O_1O_2O$, where each of the subscripted "$O_{1-2}$"; i.e., "$O_1$" and "$O_2$", is predetermined and constant (the same within the set), O is a predetermined residue that can be each of the twenty natural amino acid residues, and the remaining positions are occupied by mixtures. Similar sets of sets have the first 3 positions occupied by specific predetermined residues, the fourth position occupied by one of the amino acids used in the study, and positions 5 and 6 occupied by mixtures. Another set of sets has the first four positions defined, the fifth occupied by an amino acid residue used, and the sixth position a mixture.

Thus, the above set of sets is comprised of member sets each of which consists essentially of a mixture of equimolar amounts of linear oligopeptide chains containing the same number of residues in each oligopeptide chain; i.e., here each set has a sequence length of six amino acid residues. The members of each set have one to four amino-terminal positions occupied by the same, single, predetermined amino acid residue (the $O_1$, $O_2$, $O_3$ etc. positions) and four to one respective carboxy-terminal positions occupied by equimolar amounts of at least six different amino acid residues utilized (the equimolar mixture positions, X). The single position remaining in the mixture set; the position between those enumerated above, is occupied by one each of the amino acid residues utilized at that position.

The number of sets within the set of sets is determined by the number of different amino acid residues utilized at the above, single remaining position. Thus, where the twenty naturally occurring amino acid residues are used, each set would contain 20 members of mixtures. The number of individual oligopeptides in each mixture of a set is determined by multiplying the numbers of residues used at each equimolar mixture position.

The previously discussed 120 oligopeptide mixture sets of 6-mer sets each containing one predetermined position and five mixture positions are also contemplated, and illustrate six sets of twenty oligopeptide mixture sets. Here, again, each set contains a sequence length of six amino acid residues. One position in each set is occupied by one of a plurality of the predetermined amino acid residues utilized for that position. The remaining five positions of each set are occupied by equal molar amounts of at least six different amino acid residues. Again, the number of members of each set is determined by the number of predetermined residues utilized, and the number of oligopeptides in each member set is determined by multiplying the numbers of residues utilized at each equimolar mixture position.

The previously discussed mixtures having equimolar amounts of at least six different amino acid residues occupying the four carboxy-terminal positions also constitute a set of sets. Here, the sets contain a sequence length of five to ten amino acid residues. The amino-terminal residue in each set is occupied by each one of the predetermined amino acid residues utilized at that position (O). The amino acid residue sequence between the enumerated amino-terminal residue and four carboxy-terminal positions, is the same in each set from a carboxy-terminal direction to an amino-terminal direction ($O_6$, $O_5$, $O_3$ etc.). A set containing a sequence length of five amino acid residues has no amino acid residue sequence between the enumerated positions, so that intervening sequence is sometimes referred to as "when present" to account for the 5-mer set.

Still further sets of oligopeptide mixture sets will be apparent to the skilled worker from the previous discussion and need not be gone into further here.

Compositions and Assays

A composition that comprises a self-solubilizing unsupported oligopeptide mixture set dissolved in an aqueous medium at a concentration of about 1 milligram per liter to about 100 grams/liter is also contemplated. The mixture set consists essentially of a mixture of equimolar amounts of linear oligopeptide chains containing the same number of amino acid residues in each chain. Each member of the set contains one or more single, predetermined amino acid residues at one or more predetermined positions of the oligopeptide chain and equimolar amounts of at least six different amino acid residues at one or more other positions of the chain.

The aqueous medium used can be extremely varied and includes tap water, distilled or deionized water, as well as a buffer solution as is used for antibody binding studies or a cell growth medium as is useful for bacteria, plant or animal cells, all of which are well known to skilled workers. In a particularly preferred embodiment, the aqueous medium is a cell growth medium that also contains cells whose growth in the presence of a dissolved oligopeptide set is to be assayed.

The concentration of an oligopeptide mixture set in the aqueous medium is selected so that the mixtures of the oligopeptide set are present at concentrations of about 1.0

μg/ml to about 100 mg/ml, or when each oligopeptide mixture is made up of 160,000 individual oligopeptides; i.e., an N-acetyl C-amide 6-mer beginning Arg-Trp then each peptide within each mixture is present in a concentration of about 1.0 μg/ml/160,000=6.25 pg/ml, to about 100 mg/ml/ 160,000=625 ng/ml. Presuming an average molecular weight of an N-acetyl C-amide 6-mer to be 785 gm/mole, then at 1.0 μg/ml, the individual hexamers are present at a concentration of 7.96 pmolar and at 100 mg/ml the individual hexamers are present at 796 nmolar. More preferably, concentrations of about 100 μg/ml to about 500 μg/ml are used. It is to be understood that the wide breadth of concentrations specified above is intended to take into account the contemplated range of oligopeptide mixture sets that can have one to nine positions predetermined. Specific, useful concentrations are illustrated hereinafter.

Another aspect of the present invention is the use of a before-described aqueous composition of a set of mixed oligopeptides in a binding assay with an appropriate acceptor. An oligopeptide mixture set of such a composition and its individual members can be looked at as donor (ligand) in donor-acceptor binding complex formation. Exemplary acceptor molecules are antibody combining site-containing molecules such as whole antibodies, F(ab), F(ab')$_2$ and Fv antibody portions, solubilized or non-solubilized cell surface receptor molecules, internal cellular receptors and viral protein receptors, all but the antibody combining site-containing molecules being collectively referred to as "cellular receptors".

In accordance with this aspect of the invention, a before-described aqueous medium containing an oligopeptide mixture set is contacted with acceptor molecules whose binding is to be assayed to form a binding reaction mixture. That mixture is maintained for at time period and under conditions for the acceptor to bind to an oligopeptide of the mixture, and the relative binding amount is determined.

Any well known binding assay format can be used. For example, a solid phase assay using a solid phase-bound antibody binding site and a radiolabeled oligopeptide mixture set is contemplated. Also contemplated is a competitive binding assay in which a protein or polypeptide is bound to a solid phase as an antigen and a monoclonal antibody binding to that antigen is admixed with an oligopeptide mixture set. Inhibition of binding of the monoclonal antibody by the oligopeptide mixture set provides a measure of the binding between the oligopeptides and monoclonal antibody.

For a before-discussed chromophore- or fluorescent-labeled oligopeptide mixture set, contact between the acceptor and oligopeptide mixture set can be carried out with the acceptor linked to a solid support such as sepharose or agarose. The non-binding and poorer binding mixture sets can be separated from the solid support-bound acceptor molecules by washing at increasingly higher salt concentrations until a predetermined concentration is reached that is used to define a better or best binding oligopeptide mixture. The choromophoric or fluorescent label can be used to follow the elution. Using the 2,4-dinitrophenyl chromophore as exemplary, the presence of a yellow to yellow/orange color on the solid support for a given mixture set after washing indicates an optimal binding mixture set.

An exemplary assay using a photoreactive label can be carried out with an enzyme having a known substrate. Here, the enzyme as acceptor and photoreactive labeled-oligopeptide are admixed and the admixture maintained so that binding can occur. The admixture is then irradiated using sufficient quanta of light at an appropriate wavelength, as are well known, to cause the decomposition of the photoreactive group such as an azide group and the insertion of the resulting oligopeptide radical into the enzyme polypeptide backbone. That insertion links the resulting oligopeptide to the enzyme and blocks reaction with the enzyme's substrate. Thus, an assay of enzymic activity after irradiation provides a determination of which oligopeptide mixture set bound optimally, with a diminished activity indicating enhanced binding.

Cellular receptor molecules are also particularly contemplated as useful in this assay system. The cellular receptor whose binding is contemplated for assay need not be isolated, but can be part of an intact, living cell such as bacterial, mammalian or plant cells, or viruses. When such intact, living cells are utilized, relative binding amounts can be determined by the growth or inhibition of growth of the admixed, assayed cells. The aqueous medium here is a growth medium, known to promote growth of the assayed cells.

Example 3 hereinafter illustrates use of two different intact bacterial cells as acceptors in exemplary assays. Example 5 describes assays against a fungus, with assays against another bacterial type being illustrated in Example 6, and a virus in Example 7. In those assays, inhibition of growth of the bacteria or viral plaques was used as a measure of binding of an acceptor to several oligopeptide mixture sets, so most of the illustrated data illustrate inhibition of growth, with non-inhibition data generally not shown for brevity.

The concentration of free acceptor molecules or those present in intact, living cells used for such binding assays is an assay-effective amount such as is normally used for such assays, and is well known in the art. It is to be understood that different concentrations of free acceptor molecules or those present in intact, living cells can vary with each acceptor studied.

A before-described assay can be carried out in vitro as is specifically illustrated hereinafter, as well as being carried out in vivo. For in vivo assays, living plants such as tobacco, alfalfa, corn (maize), zinnias and the like are contemplated hosts, whereas small laboratory mammals such as rats, mice, guinea pigs and rabbits are contemplated hosts for animal assays.

An oligopeptide mixture set-containing composition can be administered and an oligopeptide mixture contacted with the acceptors internally or externally in plants through watering, misting of foliage, or injection. For the animals, a composition can be administered internally, orally or by injection such as intraperitoneally, subcutaneously or intramuscularly or topically as by application to skin for the contact between donor and acceptor to take place.

Binding here can be assessed by relative growth rate (positive or negative) or by the affect of the composition on one or more tissues, as through microscopic examination, by body temperature where pathogen-infected animals are used, and the like as are well known.

In preferred practice, an above binding assay is repeated using an aqueous composition containing another member of a set of oligopeptide mixture sets. Comparison of the relative binding results obtained indicates which sequence(s) of the member sets of sets provide the best (or better) binding. Those binding study results can then be utilized to prepare a further set of oligopeptide mixture sets that include the best (or better) binding sequences. That further set can be similarly assayed to identify further best (or better) binding sequences until one or more sequences that provide a desired binding result is identified.

Based upon results of the above-described assays, several oligopeptides of interest were identified that exhibited antimicrobial activity. Those oligopeptides of particular interest that exhibited antimicrobial activity include those having the 6-mer sequences:

Phe-Arg-Trp-Leu-Leu-Xaa (SEQ ID NO:10)
Phe-Arg-Trp-Trp-His-Xaa (SEQ ID NO:11);
Arg-Arg-Trp-Trp-Met-Xaa (SEQ ID NO:12);
Arg-Arg-Trp-Trp-Cys-Xaa (SEQ ID NO:13); and
Arg-Arg-Trp-Trp-Arg-Xaa (SEQ ID NO:14)
wherein Xaa is another amino acid residue.

In preferred practice, an above oligopeptide is utilized as an N-acetyl C-amide derivative. Particularly preferred Xaa residues for an oligopeptide of SEQ ID NO:10, when used against *E. coli* are arginine, lysine, histidine and valine, whereas for use against *S. aureus,* Xaa is preferably phenylalanine, arginine, tryptophan, cysteine and leucine. Particularly preferred Xaa residues for SEQ ID NO:11 include arginine, lysine, tryptophan, phenylanine, histidine and leucine for use against *E. coli,* and leucine, phenylalanine, arginine, isoleucine, tryptophan and lysine for use against *S. aureus.* Particularly preferred Xaa residues for SEQ ID NO:12 include all of the twenty naturally occurring amino acid residues except aspartic acid, glutamine and glutamic acid for use against *E. coli.* Particularly preferred Xaa residues for SEQ ID NO:13 include arginine, tryptophan, valine, tyrosine, lysine, serine, histidine, threonine and alanine for use against *S. aureus,* arginine for use against *C. albicans,* and alanine, glycine, cysteine, methionine, phenylalanine and lysine against Herpes Simplex Virus Type 1 (HSV-1). Particularly preferred Xaa residues for SEQ ID NO:14 include tyrosine, cysteine, leucine, isoleucine and alanine for use against *S. aureus* and arginine and histidine for use against *C. albicans.*

Heptapeptides (7-mers) including an above peptide have been found to exhibit enhanced activity. Thus, for example, peptides of SEQ ID NO:14 where Xaa is phenylalanine, and having an additional residue present at the amino-terminus or carboxy-terminus have been found to exhibit added activity.

Thus, an added amino-terminal tyrosine, isoleucine, tryptophan, phenylalanine, leucine, cysteine and arginine have been found useful against *S. aureus,* and an added amino-terminal lysine has provided enhanced activity against *C. albicans.* An added carboxy-terminal tryptophan, phenylalanine, leucine, cysteine, isoleucine, tyrosine, valine or arginine residue has been found to enhance activity against *S. aureus,* whereas an added arginine or lysine provided enhanced activity against *C. albicans.* For a peptide of SEQ ID NO:14, where Xaa is valine, an added C-terminal arginine provided enhanced activity against *C. albicans.*

The following examples are intended to illustrate, but not limit, the invention.

EXAMPLE 1

Exemplary Synthesis of a Set of Mixed Oligopeptides having Equimolar Amounts of the Twenty Natural Amino Acid Residues Aliquots of five grams (4.65 mmols) of p-methylbenzhydrylamine hydrochloride resin (MBHA) were placed into twenty porous polypropylene bags. These bags were placed into a common container and washed with 1.0 liter of $CH_2Cl_2$ three times (three minutes each time), then again washed three times (three minutes each time) with 1.0 liter of 5 percent $DIEA/CH_2Cl_2$ (DIEA=diisopropylethylamine).

The bags were then rinsed with $CH_2Cl_2$ and placed into separate reaction vessels each containing 50 ml (0.56M) of the respective t-Boc-amino acid/$CH_2Cl_2$. N-N-Diisopropylcarbodiimide (25 ml; 1.12M) was added to each container, as a coupling agent.

Asparagine and glutamine were coupled as their hydroxybenzotriazole esters in 50/50 (v/v) DMF/$CH_2Cl_2$. After one hour of vigorous shaking, Gisen's picric acid test [Gisen, *Anal. Chem. Acta,* 58:248–249 (1972)] was performed to determine the completeness of the coupling reaction. On confirming completeness of reaction, all of the resin packets were then washed with 1.5 liters of DMF and washed two more times with 1.5 liters of $CH_2Cl_2$.

After rinsing, the resins were removed from their separate packets and admixed together to form a pool in a common bag. The resulting resin mixture was then dried and weighed, divided again into 20 equal portions (aliquots), and placed into 20 further polypropylene bags (enclosed). In a common reaction vessel the following steps were carried out: 1) deprotection was carried out on the enclosed aliquots for thirty minutes with 1.5 liters of 55 percent TFA/$CH_2Cl_2$; and 2) neutralization was carried out with three washes of 1.5 liters each of 5 percent DIEA/$CH_2Cl_2$.

Each bag was placed in a separate solution of activated t-Boc-amino acid derivative and the coupling reaction carried out to completion as before. All coupling reactions were monitored using the above quantitative picric acid assay. Next, the bags were opened and the resulting t-Boc-protected dipeptide resins were mixed together to form a pool, aliquots were made from the pool, the aliquots were enclosed, deprotected and further reactions were carried out.

This process can be repeated any number of times yielding at each step an equimolar representation of the desired number of amino acid residues in the peptide chain. The principal process steps are conveniently referred to as a divide-couple-recombine (DCR) synthesis.

The side chain protecting groups used with α-amino-terminal t-Boc and f-Moc protecting groups are usually different. The side chain protecting groups utilized for one type of synthesis or the other are as shown in the table below. Other usually used side chain protecting groups are also utilized for both types of syntheses.

| | Side Chain Protecting Group | |
|---|---|---|
| Amino Acid Derivative | N-t-Boc Protected | N-f-Moc Protected |
| Arginine | Toluenesulfonyl* | Benzenesulfonyl |
| Cysteine | p-Methoxybenzyl | t-Butyl |
| Glutamic acid | O-Benzyl | t-Butyl ester |
| Histidine | N-im-dinitrophenyl* | Trityl |
| Lysine | N-(o-chlorobenzyl-oxycarbonyl) | t-Boc |
| Serine | O-Benzyl | t-Butyl |
| Threonine | O-Benzyl | t-Butyl |
| Tyrosine | O-(m-bromobenzenyl-oxycarbonyl) | t-Butyl |
| Aspartic acid | O-Benzyl | t-Butyl ester |

*Arginine and histidine are coupled in the presence of N-hydroxylbenztriazole [Hruby et al., Angew. Chem. Int. Ed. Engl., 10:336–339 (1971)]

For oligopeptide mixture sets not having an N-terminal $C_1$–$C_8$ acyl (e.g. acetyl) group, the following procedure was used for side chain deprotection of N-t-Boc-protected oligopeptide chains. The fully protected solid support-coupled oligopeptide mixtures were treated with 55 percent trifluoroacetic acid in methylene chloride prior to the HF treatment to remove the final t-Boc-protecting group. Then the protected solid support-coupled oligopeptide mixtures, in polypropylene mesh packets [Houghten, *Proc. Natl. Acad. Sci., USA*, 82:5131–5135 (1985)] were rinsed with alternating washes of $CH_2Cl_2$ and isopropanol, and dried under reduced pressure for twenty-four hours.

The low HF step [Tam et al., *J. Am. Chem. Soc.*, 195:6442–6455 (1983)] was carried out in a two liter polypropylene reaction vessel, using a solution of 60 percent dimethylsulfide, 25 percent HF, ten percent p-cresol and five percent ethylenedithiol. HF was condensed at −78° C. After condensation, the HF-scavenger solution was carefully transferred to the reaction vessel that contained the resin-containing packets. The low HF solution was made to give 5 mls per 0.1 mmol of oligopeptide. After the reagents were added, the reaction vessel was placed in an ice water bath and shaken for two hours. The low HF solution was removed and the packets containing the deprotected peptide resins were quickly washed with chilled $CH_2Cl_2$. The $CH_2Cl_2$ wash was repeated nine times (one minute each) followed by ten alternating washes of isopropanol and $CH_2Cl_2$. Finally, the resin was washed five times with DMF, then twice more with $CH_2Cl_2$. Deprotected peptide resin packets were dried under reduced pressure. After this process was completed, the unprotected peptides were ready to be cleaved by anhydrous HF as discussed elsewhere.

The N-terminal f-Moc protecting groups of enclosed, protected solid support-coupled oligopeptide mixtures were removed by treatment with twenty percent piperidine in DMF for ten minutes. Then the resulting N-deprotected, side chain-protected peptide resins in polypropylene packets were washed with DMF twice (five minutes each) followed by two rinses with $CH_2Cl_2$ (one minute each) and dried in a vacuum for twenty-four hours. While porous containers are not utilized, each solid support-coupled reaction product must still be maintained separately during reactions.

The side chain deprotection was carried out in a two liter polypropylene reaction vessel, using a solution of 85 percent TFA, 5 percent phenol, 4 percent thioanisole, 4 percent deionized $H_2O$ and 2 percent ethanedithiol. The resins were shaken for 3.5 hours at room temperature. The reaction solution was removed, and the packets containing the completely deprotected solid support-coupled oligopeptide mixtures were quickly washed with chilled ether. The ether wash was repeated nine times (one minute each) followed by ten alternating washes of isopropanol and $CH_2Cl_2$. Finally, the solid support-coupled oligopeptide mixtures were washed five times with DMF, then twice more with $CH_2Cl_2$. Deprotected solid support-coupled oligopeptide mixtures and their enclosing packets were dried under reduced pressure. After this process was completed, the unprotected peptides were ready to be cleaved by anhydrous HF, as discussed above.

Where an N-acyl group such as an acetyl group is to be present on an oligopeptide mixture set, the final t-Boc or f-Moc protecting group is removed as above, an excess of acetic anhydride is added and the reaction is maintained until there are no more free amino groups present as discussed elsewhere herein. The above rinsing and drying steps are then carried out, followed by deprotection and cleavage of the oligopeptide mixture set from the solid support.

As noted earlier, use of a benzhydrylamine resin as a solid support and anhydrous HF/anisole for cleavage of the oligopeptide mixture set provides a C-terminal amido group for the oligopeptide mixture set produced. Use of a benzhydrylalcohol resin solid support and that cleavage procedure provides a C-terminal carboxylic acid. Use of a before-discussed disulfide-containing linking group between the solid support and oligopeptide chains and cleavage with a disulfide bond breaking agent as discussed provides a C-terminal mercaptan linking group amide-bonded to the oligopeptide chains.

EXAMPLE 2

Identification of an Epitope Bound by a Monoclonal Antibody

A synthetic combinatorial peptide library was prepared as described in Example 1 and screened to determine the ability of individual member sets to inhibit antipeptide-monoclonal antibody binding to the polypeptide by competitive ELISA. The oligopeptide library used consisted of 400 individual sets of oligopeptide mixture sets, six residues in length, containing an N-terminal acetyl group (Ac) and a C-terminal amide groups, and in which the two N-terminal amino acid residue positions were specifically defined as individual predetermined amino acid residues, with each of the remaining four positions comprised of a mixture of 19 amino acid residues, cysteine excluded. Using 20 amino acid derivatives, the specifically defined positions $O_1$ and $O_2$ result in 400 different oligopeptide mixture sets, each consisting of approximately 130,600 ($19^4$) equimolar 6-mers.

The 400 oligopeptide sets (synthetic combinatorial library) were prepared as discussed in Example 1 using the DCR synthesis to prepare a single solid support-coupled oligopeptide reaction product mixture pool four amino acid residues in length from the 19 amino acid derivatives coupled. That pool was divided into twenty aliquots and each was reacted with a separate amino acid residue, following usual SMPS procedures to form twenty reaction products having a single residue at the N-terminus and equimolar mixtures of nineteen residues at the other four positions. Each of those twenty solid support-coupled oligopeptide aliquots was then divided into twenty aliquots and each was reacted separately with one of the twenty previously used amino acid derivatives. After reaction, the N-terminal t-Boc groups were removed and the N-terminal residues were acetylated to form the 400 N-acetyl 6-mer solid support-coupled oligopeptide mixtures. Those mixtures were cleaved from the resin with anhydrous HF/anisole to form the 400 N-acetyl C-amide oligopeptide mixture sets utilized in this study.

A group of 400 mixture sets such as those discussed above typically takes about four to six weeks to prepare by a single individual working a usual five-day workweek.

Figure 2:
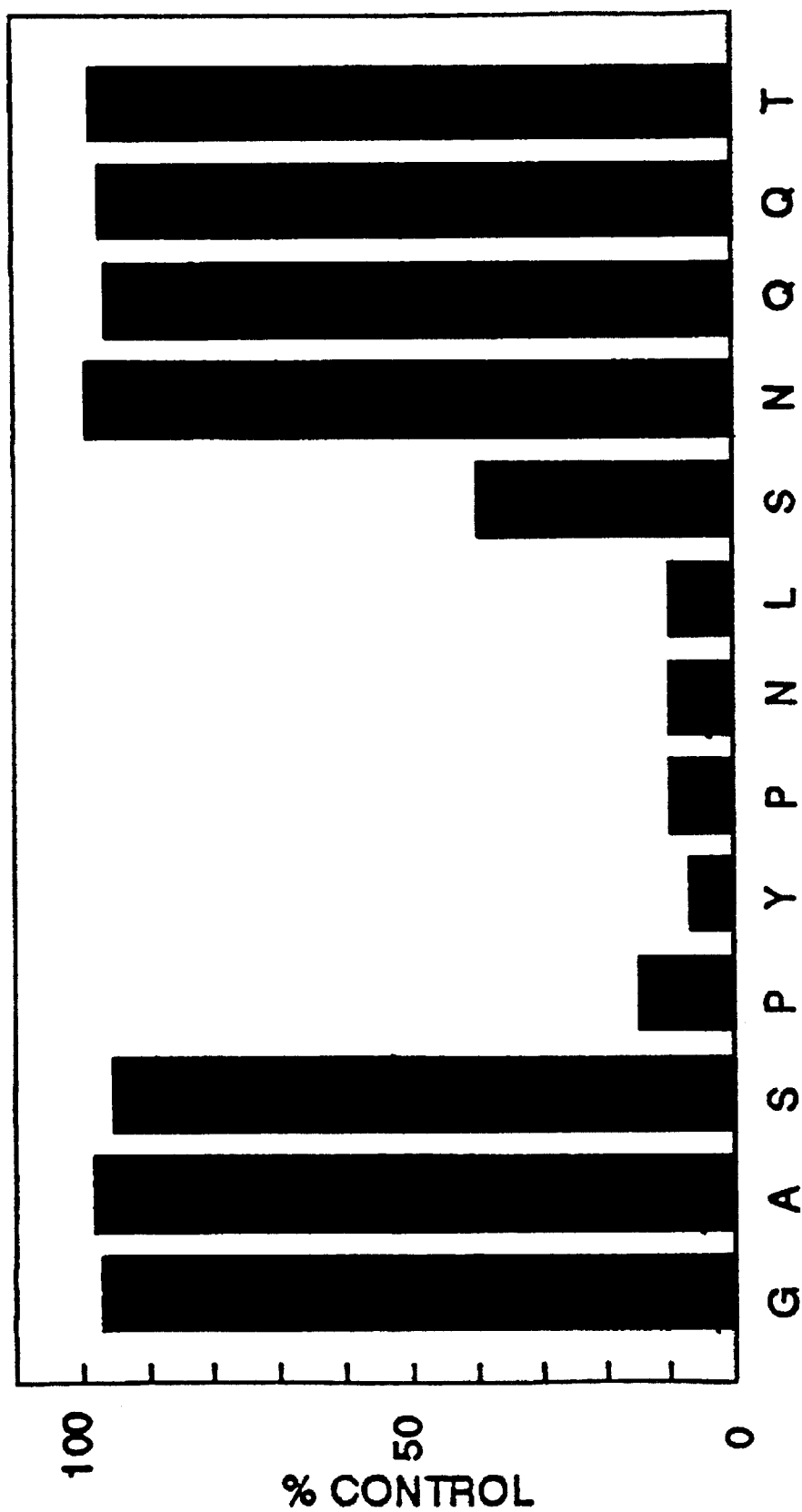
FIG. 2 is a graph showing the relative binding of a series of deletion analogs of an oligopeptide having the sequence Gly-Ala-Ser-Pro-Tyr-Pro-Asn-Leu-Ser-Asn-Gln-Gln-Thr (SEQ ID NO:1) by monoclonal antibody (mAb) 125-10F3. The ordinate shows the percentage of binding of an oligopeptide deletion analog by the monoclonal antibody relative to binding of the intact oligopeptide. The abscissa indicates the residue in the sequence that was deleted for each assay.
Figure 3A:
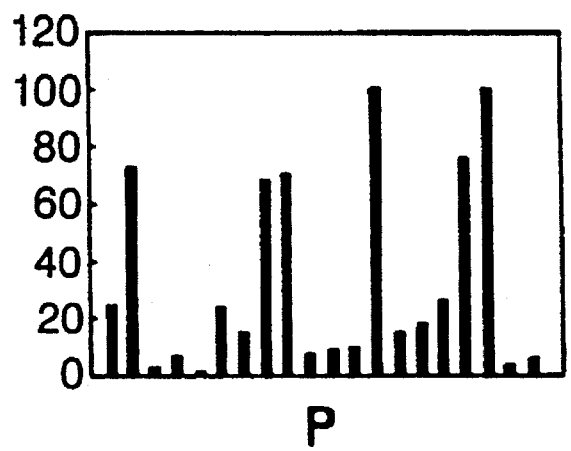
FIG. 3 is a series of six graphs (FIGS. 3A–3F) that illustrate the complete substitution profile of the antigenic determinant of the polypeptide SEQ ID NO:1 when each residue in the 6-mer epitope sequence was replaced by one of 20 of the natural amino acid residues. The ordinate for each graph is the percentage of binding by monoclonal antibody 125-10F3 relative to the 6-mer epitope sequence Pro-Tyr-Pro-Asn-Leu-Ser (SEQ ID NO:2). The twenty bars of the abscissa for each graph are for each of the twenty amino acid residues, listed alphabetically. Individual letters under each graph indicate the residue of the natural epitope that was substituted. graph indicate the residue of the nat are oligopeptides prepared from most or all of the twenty naturally occurring amino acids. It will be understood, however, that the invention can be used with any number of amino acids, including more or less than twenty.
Figure 3B:
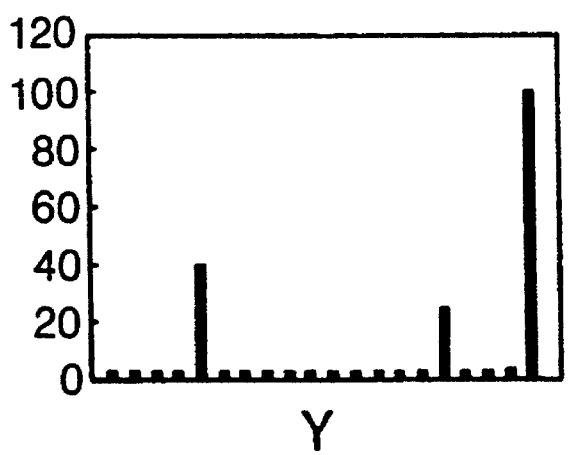
Figure 3C:
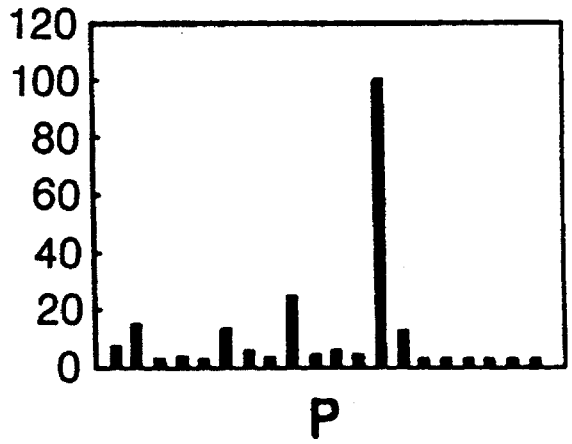
Figure 3D:
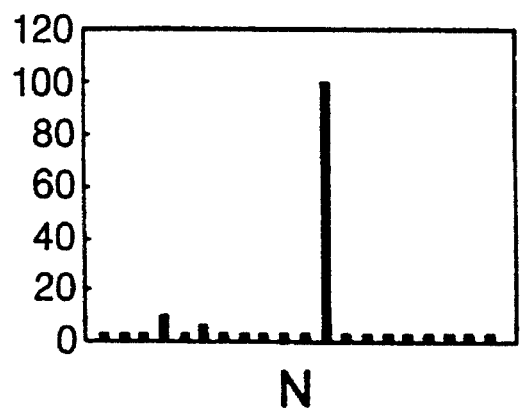
Figure 3E:
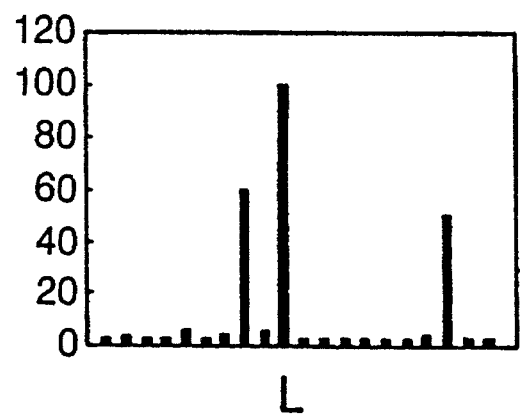
Figure 3F:
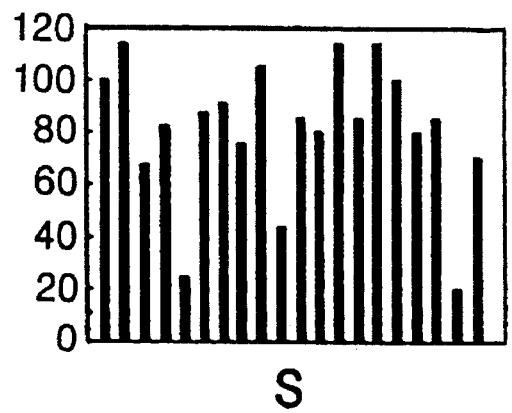
Figure 4A:
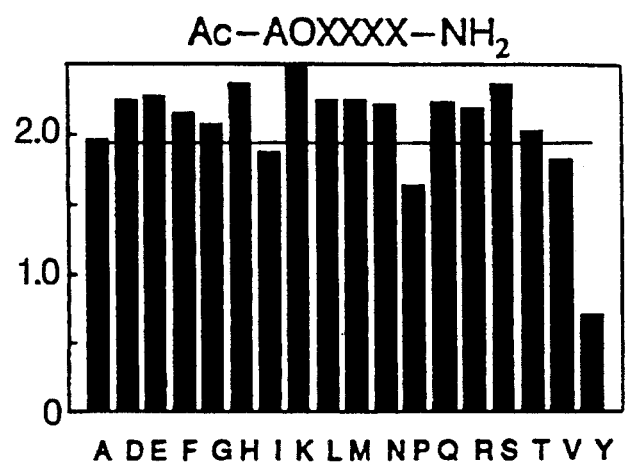
Figure 4B:
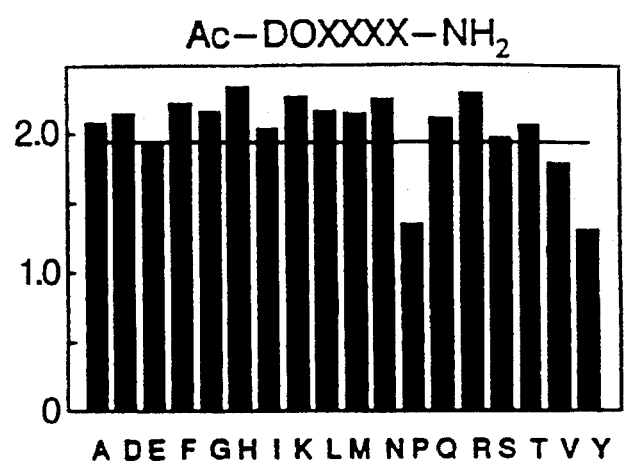
Figure 4C:
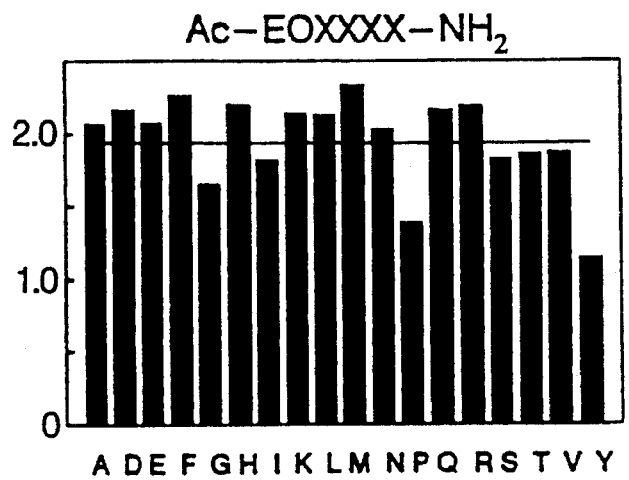
Figure 4D:
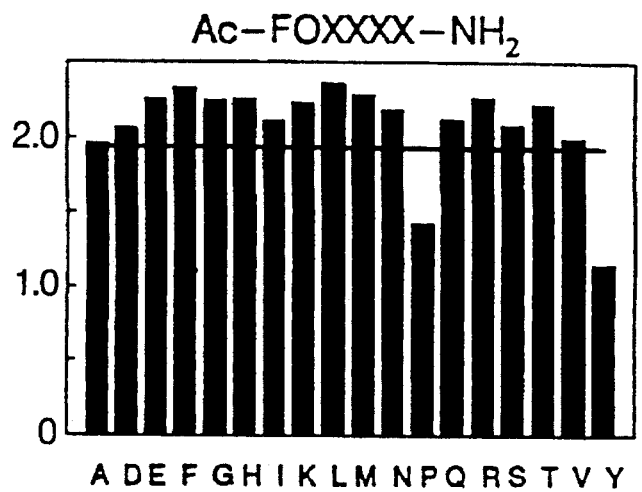
Figure 4E:
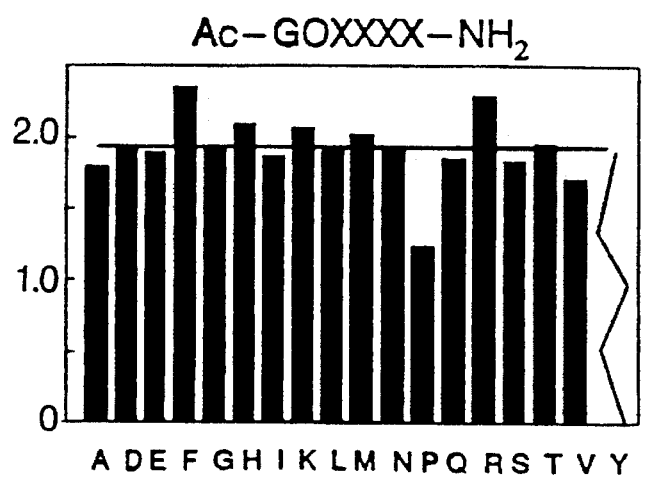
Figure 4F:
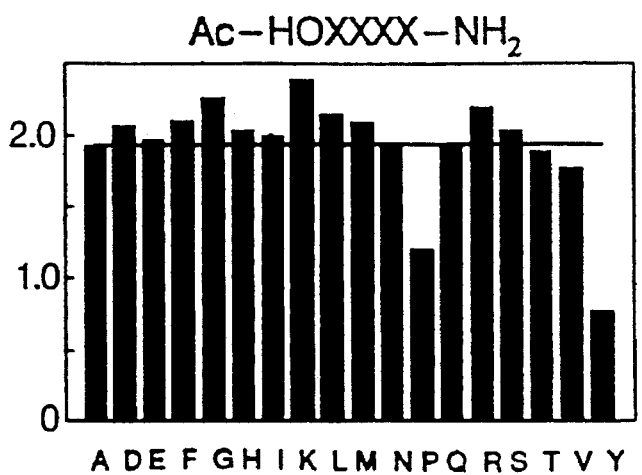
Figure 4G:
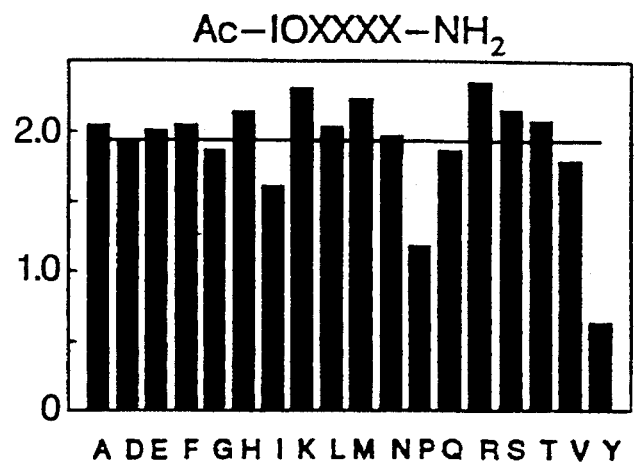
Figure 4H:
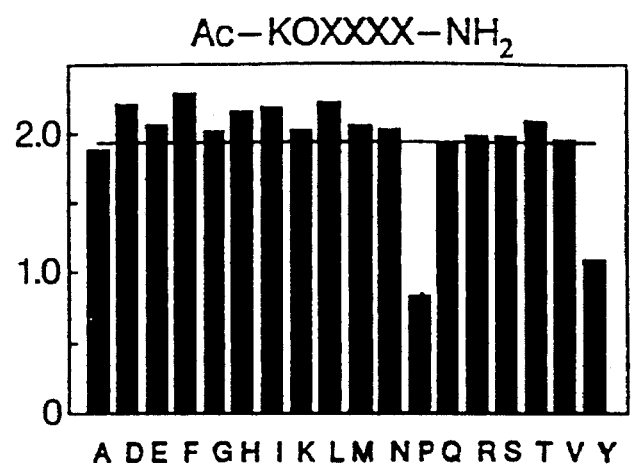
Figure 4I:
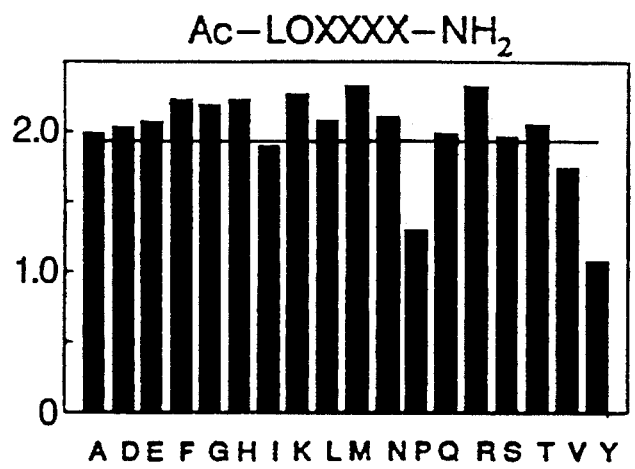
Figure 4J:
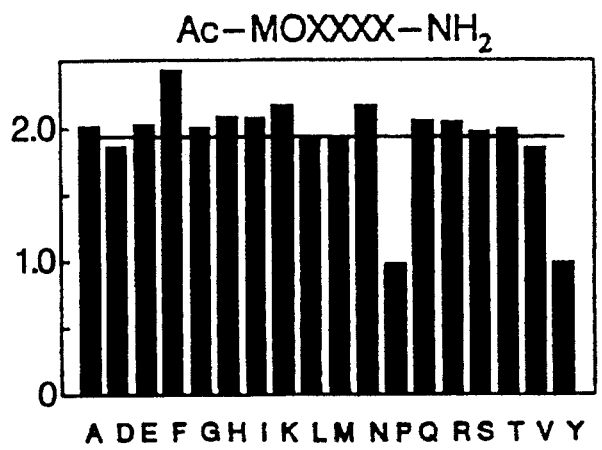
Figure 4K:
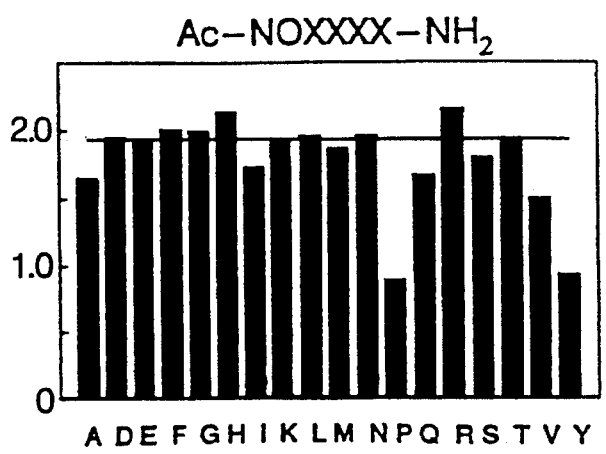
Figure 4L:
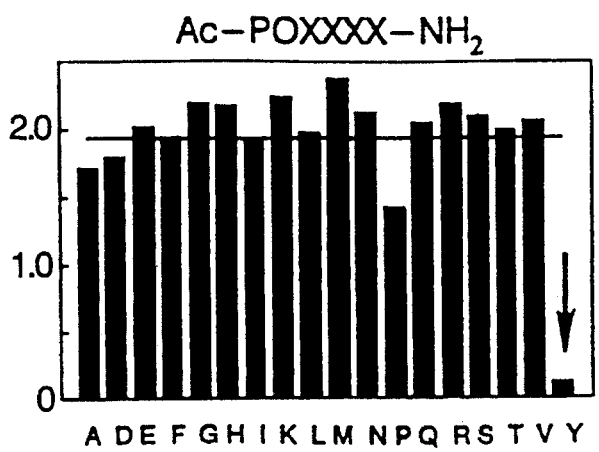
Figure 4M:
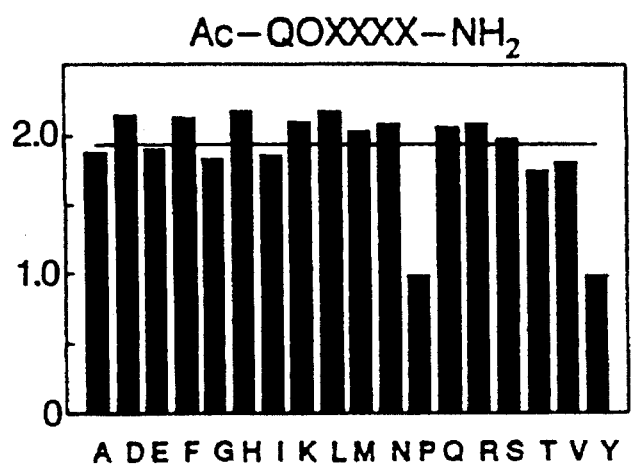
Figure 4N:
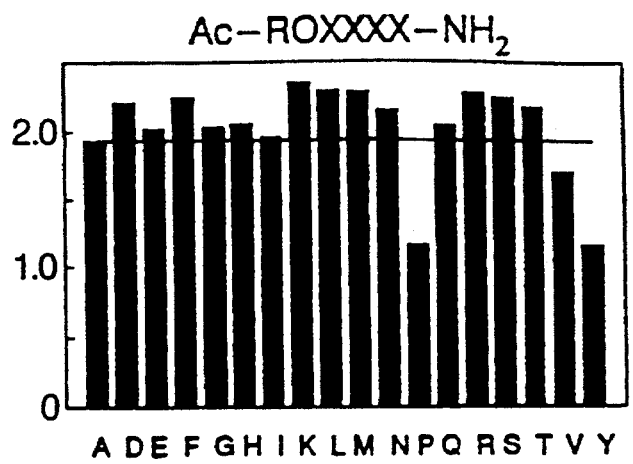
Figure 4O:
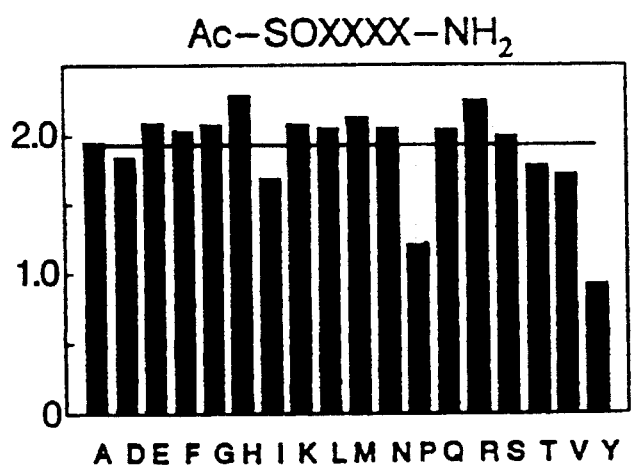
Figure 4P:
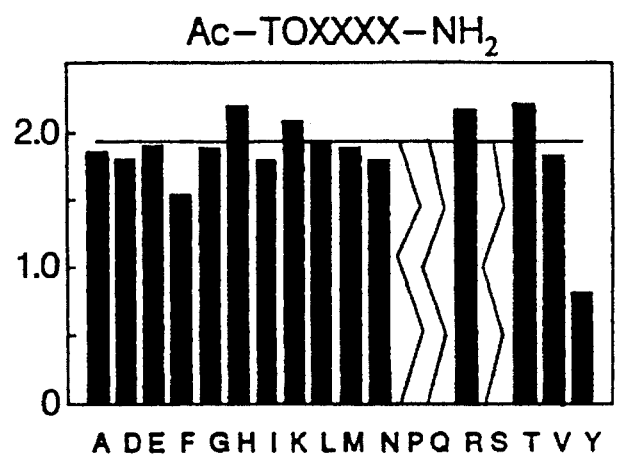
Figure 4Q:
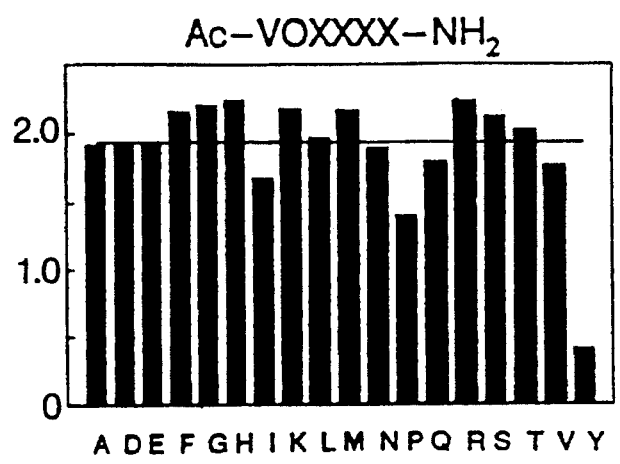
Figure 4R:
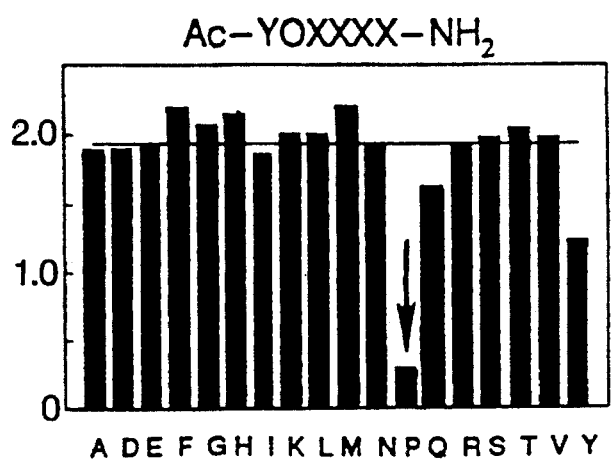

Monoclonal antibody (mAb) 125-10F3 was used in these studies, which binds specifically to a 13-residue polypeptide Gly-Ala-Ser-Pro-Tyr-Pro-Asn-Leu-Ser-Asn-Gln-Gln-Thr (SEQ ID NO:1) [Appel et al., *J. Immunol.*, 144:976–983 (1990)]. The antigenic determinant recognized by the mAb is Pro-Tyr-Pro-Asn-Leu-Ser (SEQ ID NO:2), determined previously using individual omission analogs of the polypeptide as is seen in FIG. 2.

FIG. 3 illustrates the complete substitution profile of the antigenic determinant in which each residue was individually replaced with the twenty other natural amino acids. The central four residues, Tyr-Pro-Asn-Leu (SEQ ID NO:3), are the most specific residues of the polypeptide-mAb interaction. By this it is meant that very few substitution oligopeptide analogs are recognized by the mAb being studied. The outer residues of the antigenic determinant, namely proline and serine, are relatively redundant positions; i.e., many substitution analogs for these positions are recognized by the mAb.

The peptide library was screened utilizing a competitive ELISA system that measured the inhibition in solution of the binding of the mAb to polypeptide SEQ ID NO:1 adsorbed to an assay plate by each individual element of the synthetic combinatorial library. The oligopeptide mixture sets that significantly inhibited the mAb from binding to the polypeptide were those whose amino-terminal residues were N-acetyl Pro-Tyr and Tyr-Pro (Ac-Pro-Tyr and Ac-Tyr-Pro). Screening data for an exemplary eighteen of the 400 sets are shown in FIG. 4, with arrows at the two best binding sequences.

The above first oligopeptide set corresponds to the known first two positions of the antigenic determinant. The above second oligopeptide mixture set can be rationalized to inhibit because the first position of the antigenic determinant in the polypeptide, namely proline, is a redundant position, as discussed before. Thus, the sequence Tyr-Pro corresponds to the second and third positions of the antigenic determinant.

The concentration of the inhibiting oligopeptide sets at which 50 percent of the mAb was inhibited in its binding to the polypeptide (IC-50) was determined. In this manner, one can determine the relative effectiveness of the most effective peptide mixture from the group of inhibiting peptide mixtures.

The oligopeptide set having Ac-Pro-Tyr with an IC-50 of 20 µM was clearly the most effective oligopeptide mixture for inhibiting the mAb binding to the polypeptide, whereas the set having an initial Ac-Tyr-Pro had an IC-50 of 200 µM. Those two best binding oligopeptide sets were used to define the third position.

The oligopeptide sets were synthesized in a similar manner as described before, but the third position from the N-terminus, "O", was defined with each of the 20 natural amino acids resulting in a total of 40 oligopeptide sets (two sets of twenty sets each) being studied. These oligopeptide sets were assayed by the above competitive ELISA.

Three oligopeptide sets had quite effectively low inhibiting concentrations. Thus, for the set beginning Ac-Pro-Tyr, addition of a proline at position 3 dropped the IC-50 value to 1.6 µM, whereas addition of a glycine about halved the prior value. Other residues at position 3 had IC-50 values about equal to or worse than those of the starting peptide. For the set starting Ac-Tyr-Pro, addition of asparagine or tyrosine showed the best results, with IC-50 values of about 4.25 and 6.85 µM, respectively.

Interestingly, peptide sets whose sequences started with Ac-Pro-Tyr and Ac-Tyr-Pro had lower inhibiting concentrations than most of the peptides in which their third positions were defined. This substantiates the thought that the most effective 6-mer peptide (Pro-Tyr-Pro-Asn-Leu-Ser) SEQ ID NO:2 can be "found" by the mAb using the peptide library as a starting point. Those three peptide sets were used to define the fourth position.

Peptide sets were synthesized in which the N-terminal four positions were defined by each of the 20 natural amino acids, resulting in 60 oligopeptide sets; i.e., three sets of twenty sets. Oligopeptide sets were assayed by competitive ELISA as before to yield two peptide mixtures having inhibiting concentrations of interest. The first starting with Ac-Pro-Tyr-Pro and having an asparagine at position 4, and mixtures at positions 5 and 6 had an IC-50 value of 0.2 µM. The second, starting with Ac-Tyr-Pro-Asn, having a leucine at position 4 and mixtures at positions 5 and 6 had an IC-50 value of 0.6 µM.

Another oligopeptide mixture set based on the starting sequence Ac-Pro-Tyr with the third and fourth positions defined as above, the fifth position being individually varied and the sixth a mixture was prepared and screened as before. The results indicated that only one mixture had a lower IC-50 value than did the mixture with four defined positions. A final set of twenty 6-mer oligopeptide mixtures was prepared and screened in the above assay using the sequence information obtained from the assay. The results of that screening showed that the peptide Ac-Pro-Tyr-Pro-Asn-Leu-Ser-NH$_2$ (SEQ ID NO:15), having the sequence of the antigenic determinant discussed before, had an IC-50 value of 0.01 µM.

Variance of the C-terminal position was observed as expected from observed redundancy at the position occupied by the C-terminal serine residue.

Further control studies were also carried out with the oligopeptide mixture sets of this example. In one control study, the oligopeptide mixture set beginning Ac-Pro-Tyr used herein, where positions 3–6 were occupied by equimolar mixture of nineteen residues, all except cysteine, was assayed in the before-discussed binding inhibition assay as was a second oligopeptide mixture set of the initial sequence whose positions 3–6 contained equimolar mixtures were mixtures of eighteen amino acid residues. The eighteen residues utilized for those equimolar mixtures excluded cysteine as before, and also lacked the residue known to be present in polypeptide SEQ ID NO:1 at the same sequence position. Thus, in the mixtures, position 3 lacked cysteine and proline, position 4 lacked cysteine and asparagine, position 5 lacked cysteine and leucine, and position 6 lacked cysteine and serine.

The results of these studies were that the IC-50 value for the set starting Ac-Pro-Tyr with positions 3–6 occupied by a mixture of nineteen residues was 20 µM, whereas the IC-50 value for mixture containing eighteen residues was greater than 1400 µM. This study illustrates that the presence of two residues in the proper sequence in a 6-mer mixture, coupled with the absence of a binding-required residue at the other positions in the mixture is insufficient to cause sufficient binding of the 6-mer to the monoclonal antibody to inhibit binding of the mAb to the polypeptide antigen at a reasonable concentration. These results also illustrate that the presence of all of the residues of the epitope, as were present in mixture containing nineteen residues, permitted ready binding of the oligopeptide mixture to the mAb acceptor and inhibition of binding to the antigenic polypeptide.

The studies with the C-amide-terminated oligopeptide set starting with Ac-Tyr-Pro were also completed. Binding inhibition studies with the various intermediate sets as was done before were also carried through to the identification of an optimal binding (and inhibiting) 6-mer. The results showed that the optimal sequence was Ac-Tyr-Pro-Asn-Leu-Ser-Asn-NH$_2$ (SEQ ID NO:4) whose IC-50 value in this study was 0.15 µM. That value can be compared to that of Ac-Pro-Tyr-Pro-Asn-Leu-Ser-NH$_2$ (SEQ. ID NO:15) that was found to be 0.04 µM in this study. A similar IC-50 value was obtained for the mixture set having the sequence of the latter peptide at positions 1–5, and a mixture at position 6.

The above results show that an oligopeptide mixture that contained the previously determined five most important residues for antibody binding inhibited binding of the antibody better than did a 6-mer that contained six residues present in the antigenic polypeptide (Ac-Tyr-Pro-Asn-Leu-Ser-Asn-NH$_2$; SEQ ID NO:4), of which a four residue sequence was contained in the oligopeptide mixture. The IC-50 value difference was about a factor of four between the mixture and the single peptide of SEQ ID NO:4. These results are seen to provide further validation to the techniques described herein.

Although there was about a factor of four difference in binding inhibition for the above-discussed oligopeptides, the above data also illustrate that further residues in addition to those most important in the epitope can also be present adjacent to a sequence that is important to binding. Thus, so long as residues that inhibit binding such as a plurality of cysteines or several large hydrophobic residues that cause insolubility such as tyrosines and tryphophans are absent, added residues not needed for binding can also be present in an oligopeptide or oligopeptide mixture set.

The data herein also illustrate variability between assays in determining IC-50 values for a given oligopeptide mixture set. For that reason, the starting sets are typically included with new sets in each new assay so that each assay is consistent within itself.

An iterative screening/synthesis procedure such as is described in this example takes about four to eight weeks for a single individual working a usual five-day workweek. The length of time required is dependent upon the number of mixture sets moved ahead for further syntheses, as would be expected.

EXAMPLE 3

Antimicrobial Assays for Cellular Receptors as Acceptors

A. Antimicrobial assays

*Escherichia coli* (ATCC 25922) was used as Gram-negative (−) and *Staphylococcus aureus* (ATCC 29213) as Gram-positive (+) bacteria. Bacteria were grown overnight (about 18 hours) at 37° C. in Mueller-Hinton (MH) broth. This culture was reinoculated and incubated at 37° C. to reach the exponential phase of bacteria growth; i.e., a final bacterial suspension containing about $10^5$ to $5 \times 10^5$ colony-forming units (CFU)/ml. The concentration of cells was established by plating 100 µl of different dilutions of the culture solution (e.g., $10^{-2}$, $10^{-3}$ and $10^{-4}$) onto solid agar plates. Following an overnight (about 18 hours) incubation at 37° C., the CFU thus formed were counted on each agar plate.

96-Well tissue culture plates were utilized, with eight wells per plate containing only medium as control blanks, whereas eight other wells contained medium plus cells as a positive growth control. These controls were used to detect possible medium contamination and to provide a measure of uninhibited growth of the microorganisms.

For initial screening studies, oligopeptide sets were added to the bacterial suspension to reach a final concentration of 1 mg/ml. For MIC (minimum inhibitory concentration; i.e., concentration necessary to inhibit about 100 percent growth of the bacteria) or IC-50 (concentration necessary to inhibit 50 percent growth of bacteria), oligopeptide sets were added to the bacterial suspension at concentrations derived from two-fold dilutions ranging from 1000 µg/ml to 1.95 µg/ml.

The plates were incubated overnight (about 18 hours) at 37° C., and the optical density (OD) determined at 620 nm after different times of incubation.

B. Antimicrobial Activity of Oligopeptide Mixtures
 1. First Screening

400 Different oligopeptide mixture sets were synthesized as N-acetylated and C-amide terminals, and assayed against the two bacteria *E. coli* and *S. aureus*. Each oligopeptide mixture set had a length of six residue peptides (a combination of the 20 natural amino acids), in which only the first two N-terminal residues were predetermined (defined), and the C-terminal four positions were occupied by equimolar mixtures of residues. The peptide mixture sets were used as obtained after synthesis (i.e., in solution in water, at a concentration of about 2 mg/ml, as estimated by radioactivity through the acetyl group).

Several criteria were observed in the selection of sequences with predetermined N-termini that were used to define the third position:

1) oligopeptide sets that inhibit about 100 percent growth of the bacteria after 18–24 hours of incubation, based either or both on IC-50 or MIC values;

2) oligopeptide sets that are specific or not to one of the bacteria assayed;

3) oligopeptide sets that show chemical differences in the defined position (i.e., repetition of a particular residue was avoided);

4) if according to the above criteria, only a few combinations were found useful to define the next position, the oligopeptide mixture sets that inhibited 100 percent growth or more than 50 percent after 9 hours of incubation were also reacted.

It should be understood that other criteria than those discussed above can also be used, such as predicted water or fat solubility of the ultimate oligopeptide.

The studies here were carried out in a manner substantially identical to those discussed in Example 2, except for the screening assays, which were carried out as discussed in this example. Thus, 400 N-acetyl C-amide mixture sets whose first two positions were defined and whose C-terminal four positions were mixtures were assayed against the microbes. One or more of the best sets were then carried forward to define the third position for each against each microbe. The fourth, fifth and sixth positions were then also defined for each microbe.

Initial inhibitory screening results were determined for the 400 oligopeptide sets. The data for inhibition of *S. aureus* were sorted by results after 21 hours, whereas the data for inhibition of *E. coli* were sorted by results after 9 hours.

Thus, according to the above criteria, it was decided to move ahead with nine oligopeptide mixture sets by preparing twenty sets of each in which the N-terminal three positions were defined (predetermined) and the C-terminal three positions were mixtures. Those initial nine sets began with the residues.:

Ac-Arg-Arg and Ac-Ile-Lys, which were active against the three bacteria tested;

Ac-Ile-His, Ac-Phe-Arg, Ac-His-His and Ac-His-Lys which were more active against *E. coli* and *S. aureus;* and Ac-Phe-His, Ac-Val-Pro and Ac-Val-Arg which were more specific to *E. coli.*

2. Second Screening

A total of 180 sets of oligopeptide mixture sets (20×9) were synthesized in which the three N-terminal residues were specifically defined (predetermined). These oligopeptide sets were screened in a manner similar to the initial assay. However, a large number of mixtures were found to be active against the three bacteria, especially for those starting Ac-Arg-Arg and Ac-Phe-Arg. To choose the sets to move ahead for defining the fourth position among these two series, differences in antimicrobial activities were determined by calculating the IC-50 values of these oligopeptides.

It is noted that representation of the IC-50 data as a series of bar graphs of 1/IC-50 permits a somewhat easier evaluation of the data than does use of a tabular format, particularly where IC-50 values are similar.

Thus, the four oligopeptide sets beginning as follows were moved ahead for definition of the fourth position:

Ac-Arg-Arg-Trp and Ac-Phe-Arg-Trp which were active against the three bacteria tested;

Ac-His-His-Asp which was active against *E. coli* and *S. aureus;* and

Ac-Ile-Lys-Trp which was more specific to *E. coli.*

For the sets beginning Ac-Phe-Arg-Trp, tryptophan and leucine were the best residues at position four, and those sets were moved forward for definition of the fifth position. Tryptophan was also found to be the best fourth position residue for the set that began Ac-Arg-Arg-Trp, so that the set was moved forward. Proline was found the best fourth position residue for the set that began Ac-His-His-Asp, so that set was moved ahead.

Thus, 80 oligopeptide sets (four of twenty each) in which the four N-terminal residues were kept constant within a set and the fifth position was varied specifically were thereafter synthesized as described herein.

The fifth and sixth positions of the sets were then similarly identified to prepare completed peptides for *E. coli* and *S. aureus.*

Several peptides were thereby identified that inhibited the growth of each of the studied microbes. The better of those peptides; i.e., those with IC-50 values below about 30 μg/ml or whose IC-50 or MIC values were less than that of a prior set of 6-mer, are listed below along with representative data for each in Tables 1–6, below, in which the 6-mer peptides are denominated by the N-terminal two residues or as a derivative thereof. The sets are grouped as 6-mers whose first five positions are the same.

TABLE 1

Phe-Arg-Containing Six-Mer Peptides That Inhibit Growth of *E. coli*

| Peptide* | IC-50 (μg/ml) | MIC (μg/ml) | SEQ ID NO: |
| --- | --- | --- | --- |
| FRWLLR | 4 | 5–10 | 16 |
| FRWLLK | 5 | 5–10 | 17 |
| FRWLLH | 17 | 20–40 | 18 |
| FRWLLV | 24 | 40–80 | 19 |
| FRWWHR | 13 | 16–32 | 20 |
| FRWWHK | 15 | 16–32 | 21 |
| FRWWHW | 27 | 62–125 | 22 |
| FRWWHF | 30 | 31–62 | 23 |
| FRWWHH | 31 | 34–62 | 24 |
| FRWWHL | 31 | 62–125 | 25 |

*N-acetyl C-amide peptides were used.

TABLE 2

Arg-Arg-Containing Six-Mer Peptides That Inhibit Growth of *E. coli*

| Peptide* | IC-50 (μg/ml) | MIC (μg/ml) | SEQ ID NO: |
| --- | --- | --- | --- |
| RRWWMR | 9 | 10–16 | 26 |
| RRWWMG | 9 | 10–16 | 27 |
| RRWWMI | 12 | 16–32 | 28 |

TABLE 2-continued

Arg-Arg-Containing Six-Mer Peptides That Inhibit Growth of *E. coli*

| Peptide* | IC-50 (μg/ml) | MIC (μg/ml) | SEQ ID NO: |
| --- | --- | --- | --- |
| RRWWMC | 12 | 31–62 | 29 |
| RRWWMK | 14 | 16–32 | 30 |
| RRWWML | 15 | 16–32 | 31 |
| RRWWMY | 15 | 16–32 | 32 |
| RRWWMV | 15 | 16–32 | 33 |
| RRWWMW | 15 | 16–32 | 34 |
| RRWWMS | 17 | 20–32 | 35 |
| RRWWMT | 18 | 20–32 | 36 |
| RRWWMM | 18 | 20–32 | 37 |
| RRWWMA | 18 | 20–32 | 38 |
| RRWWMF | 18 | 20–32 | 39 |
| RRWWMH | 24 | 31–62 | 40 |
| RRWWMN | 25 | 31–62 | 41 |
| RRWWMP | 26 | 31–62 | 42 |

*N-acetyl C-amide peptides were used.

TABLE 3

Phe-Arg-Containing Six-Mer Peptides That Inhibit Growth of *S. aureus*

| Peptide* | IC-50 (μg/ml) | MIC (μg/ml) | SEQ ID NO: |
| --- | --- | --- | --- |
| FRWLLF | 11 | 9–18 | 43 |
| FRWLLR | 13 | 24–48 | 16 |
| FRWLLW | 14 | 12–24 | 44 |
| FRWLLC | 15 | 13–26 | 45 |
| FRWLLL | 18 | 16–31 | 46 |
| FRWWHL | 9.3 | 16–32 | 25 |
| FRWWHF | 16 | 31–62 | 23 |
| FRWWHR | 18 | 16–32 | 20 |
| FRWWHI | 21 | 31–62 | 47 |
| FRWWHW | 23 | 31–62 | 22 |
| FRWWHK | 30 | 31–62 | 21 |

*N-acetyl C-amide peptides were used.

TABLE 4

Arg-Arg-Containing Six-Mer Peptides That Inhibit Growth of *S. aureus*

| Peptide* | IC-50 (μg/ml) | MIC (μg/ml) | SEQ ID NO: |
| --- | --- | --- | --- |
| RRWWCR | 3.4 | 3.2–6.5 | 48 |
| RRWWCW | 4.1 | 4.5–9.0 | 49 |
| RRWWCV | 4.9 | 3.8–7.7 | 50 |
| RRWWCY | 5.4 | 4.7–9.5 | 51 |
| RRWWCK | 5.5 | 4.8–9.6 | 52 |
| RRWWCS | 5.9 | 7–14 | 53 |
| RRWWCH | 6.2 | 5.5–11 | 54 |
| RRWWCT | 7.9 | 4.9–10 | 55 |
| RRWWCA | 8.4 | 9–18 | 56 |
| RRWWRF | 5.5 | 6–9 | 57 |
| RRWWRC | 8.2 | 10–19 | 58 |
| RRWWRL | 12 | 13–26 | 59 |
| RRWWRI | 12 | 12–23 | 60 |
| RRWWRA | 14 | 18–36 | 61 |

*N-acetyl C-amide peptides were used.

Using the peptide Ac-Arg-Arg-Trp-Trp-Arg-PheNH$_2$ (SEQ ID NO:62) as exemplary, two sets of heptameric peptides were prepared in which a residue was added to the amino-terminus or the carboxy-terminus. Each of those sets contained twenty members.

The above 6-mer peptide had an IC-50 value of 8.7 μg/ml and a MIC of 8–16 μg/ml in these studies. As will be seen from the exemplary data in Table 5 and 6, below, the IC-50 and MIC values could be lessened by about one-half using a 7-mer.

TABLE 5

N-Terminal Residue-Added Seven-Mer Peptides That Inhibit the Growth of *S. aureus*

| Peptide* | IC-50 (µg/ml) | MIC (µg/ml) | SEQ ID NO: |
|---|---|---|---|
| YRRWWRF | 4.5 | 4–8 | 63 |
| IRRWWRF | 4.7 | 4–8 | 64 |
| WRRWWRF | 5.4 | 4–8 | 65 |
| FRRWWRF | 5.9 | 8–16 | 66 |
| LRRWWRF | 6.1 | 8–16 | 67 |
| CRRWWRF | 6.3 | 8–16 | 68 |
| RRRWWRF | 8 | 8–16 | 69 |

*N-acetyl C-amide peptides were used.

TABLE 6

C-Terminal Residue-Added Seven-Mer Peptides That Inhibit Growth of *S.aureus*

| Peptide* | IC-50 (µg/ml) | MIC (µg/ml) | SEQ ID NO: |
|---|---|---|---|
| RRWWRFW | 2.5 | 4–8 | 70 |
| RRWWRFF | 4.7 | 4–8 | 71 |
| RRWWRFL | 5.9 | 8–16 | 72 |
| RRWWRFC | 6.2 | 8–16 | 73 |
| RRWWRFI | 6.9 | 8–16 | 74 |
| RRWWRFY | 7.6 | 8–16 | 75 |
| RRWWRFV | 7.9 | 8–16 | 76 |
| RRWWRFR | 7.9 | 8–16 | 77 |

*N-acetyl C-amide peptides were used.

The data showed decreasing IC-50 and MIC values against *S. aureus* from the starting oligopeptide mixture set that started Ac-Arg-Arg through the most active 6-mer of this group of oligopeptides, Ac-Arg-Arg-Trp-Trp-Cys-Arg-NH$_2$ (SEQ ID NO:5). More specifically, IC-50 values were 517.1 for two identified positions 214.5 for three identified positions, 17.5 for four predetermined positions, 13.4 for five predetermined positions, and 2.7 µg/ml for the peptide of SEQ ID NO:5. MIC values in the same order were >500, 500, 31.25, 15.63 and 3.906 µg/ml.

Table 7, below, shows MIC values from a separate study for seven commercially available antibiotics and the oligopeptide of SEQ ID NO:5. As can be seen, the MIC value for the oligopeptide is about eight times greater than the most active antibacterials of the group and about one-fourth the value for the least active compound, penicillin G. In addition, the molecular weights of all of the antibiotics are within a factor of four of each other, with the oligopeptide again being between the heaviest and lightest compounds shown.

TABLE 7

Activity of Antibiotics Against *S. aureus*

| Antibiotic | MIC (µg/ml) |
|---|---|
| Erythromycin MW = 733* | 0.5 |
| Tetracycline MW = 465 | 0.5 |
| Gentamicin C MW = 909 | 0.5 |
| Neomycin MW = 909 | 1 |

TABLE 7-continued

Activity of Antibiotics Against *S. aureus*

| Antibiotic | MIC (µg/ml) |
|---|---|
| Ac-RRWWCR-NH$_2$ MW = 1003 (SEQ ID NO:5) | 3.9 |
| Ampicillin MW = 349 | 4 |
| Bacitracin A MW = 1394 | 16 |
| Penicillin G MW = 334 | 32 |

*MW = molecular weight in atomic mass units.

Finally, to evaluate the toxicity of these oligopeptide sets against another relevant type of cells, a hemolytic assay of the most active oligopeptide sets with three defined positions was carried out using human red blood cells. Assays were carried out in 96-well culture tissue plates. Four wells per plate contained 125 µl of a non-peptide positive control of the surfactant Triton X-100 [(poly)oxyethanol (9) octyl phenyl ether; 1 percent in deionized water], and four wells per plate contained 115 µl of a control blank of phosphate-buffered saline (PBS). The hemolytic peptide melittin was used as comparative control. The controls served to detect possible contamination and to calculate the percent hemolysis of each peptide.

Human red blood cells (RBC's) were washed with PBS and centrifuged to separate them from the serum. The cells are then resuspended in PBS to a final suspension of 0.5 percent RBC. This suspension (125 µl) was added to the peptide mixture and control solutions. The plates were incubated at 37° C. for one hour and centrifuged at 2800 rpm for five minutes. The release of hemoglobin resulting from the cell lysis was determined by measuring the OD at 414 nm of 100 µl of the supernatant.

At the highest concentration of oligopeptide mixture sets used for the antimicrobial assay (i.e., a two-fold dilution of the about 2 mg/ml stock solution), only a few showed a slight hemolysis effect. More specifically, the oligopeptide mixture set having three equimolar mixture positions that began Ac-Phe-Arg-Phe exhibited about 15 percent lysis and the related oligopeptide mixture set that began Ac-Phe-Arg-Trp exhibited about 7 percent lysis at 1.5 mg/ml. All of the other oligopeptide mixture sets assayed exhibited 4 percent lysis or less at 1.5 mg/ml.

Once all of the positions of a 6- or 7-mer were defined, some of the individual peptides exhibited greater hemolysis. Exemplary data for HD-50 values of some of those microbiologically inhibitory peptides is provided below in Table 8.

TABLE 8

Hemolysis by Some Microbiologically Inhibitory Peptides

| Peptide* | HD-50 (µg/ml) | SEQ ID NO: |
|---|---|---|
| FRWLLF | 34 | 43 |
| FRWLLR | 171 | 16 |
| FRWLLK | 356 | 17 |
| RRWWCW | 11 | 49 |
| RRWWCY | 50 | 51 |
| RRWWCH | 128 | 54 |
| RRWWCK | 249 | 52 |
| RRWWRFW | 59 | 70 |

TABLE 8-continued

Hemolysis by Some Microbiologically Inhibitory Peptides

| Peptide* | HD-50 (μg/ml) | SEQ ID NO: |
|---|---|---|
| RRWWRFF | 106 | 71 |
| IRRWWRF | 142 | 64 |
| WRRWWRF | 158 | 65 |
| YRRWWRF | 219 | 63 |

*N-acetyl C-amide peptides were used.

Work has also begun using mixture sets containing all D-amino acid residues. Screening of the 400 sets of N-acetyl C-amide mixtures whose first two positions were defined showed that twleve sets inhibited *E. coli* growth by more than 80 percent after incubation for 22 hours at 37° C. The two sets having the lowest IC-50 values began Ac-D-His-D-Cys and Ac-D-Arg-D-Trp. The set beginning Ac-D-His-D-Cys was selected for moving forward as it was more specivic for Gram negative bacteria.

Similar work is underway using N-acetyl C-amide all D mixture sets against *S. aureus*. Here, the four sets having four mixture positions exhibiting the lowest IC-50 values began Ac-D-Leu-D-Arg, Ac-D-Arg-D-Arg, Ac-D-Trp-D-Arg and Ac-D-Arg-D-Tyr.

EXAMPLE 4

Identification of an Epitope Bound by a Monoclonal Antibody

This study was carried out in a manner similar to that discussed in Example 2. The initially screened oligopeptide mixture set was similar to that used in Example 1 except that cysteine and tryptophan were omitted from the equimolar mixtures of the undefined C-terminal four positions (X's) so that each of the prepared 400 6-mer oligopeptide sets contained a mixture of about 105,000 ($18^4$) oligopeptides.

Monoclonal antibody (mAb) 222-35C8 was used which binds specifically to the 14-residue control polypeptide Leu-His-Asn-Asn-Glu-Ala-Gly-Arg-Thr-Thr-Val-Phe-Ser-Cys (SEQ ID NO:6) [Appel et al., *J. Immunol.*, 144:976–983 (1990)]. The antigenic determinant recognized by the mAb is Gly-Arg-Thr-Thr-Val-Phe-Ser (SEQ ID NO:7), determined previously using individual omission analogs of the polypeptide, as was discussed in Example 2. The sets of 400 oligopeptide mixture sets were assayed by competitive ELISA to measure the inhibition by each set of oligopeptide mixtures in solution of the binding of the mAb to the polypeptide adsorbed on to an assay plate.

The oligopeptide sets having two N-terminal positions defined and four C-terminal positions as equimolar mixtures that significantly inhibited the mAb from binding to the polypeptide were found to begin Ac-Gly-Arg, Ac-Arg-Gly, Ac-Gln-Glu, Ac-Glu-Ile and Ac-Gln-Val.

The most effective oligopeptide mixture set that began Ac-Gly-Arg could be expected to work since the sequence Gly-Arg is the same as the first two positions of the antigenic determinant. The assay result from the effective inhibition by the second peptide that began Ac-Arg-Gly, can be rationalized if one considers that the first position in the polypeptide, namely glycine, is being substituted by the acetyl group in the mixed oligopeptides, and that the arginine corresponds to the arginine in the second position of the antigenic determinant. The other oligopeptide mixture sets are also of interest since they have no correlation with the original sequence.

Further sets of oligopeptide mixtures were then synthesized based on the above results, in which the third position was defined for sets beginning Ac-Gly-Arg, Ac-Arg-Gly and Ac-Gln-Glu.

For the set beginning Ac-Gly-Arg, in which the third position was individually substituted with each of the 20 amino acids, ten sets that significantly inhibited mAb binding were found. It was expected that many amino acid residues substituted at the third position would effectively inhibit because the threonine at the ninth position in the control polypeptide can be replaced by most other amino acids and still retain antibody recognition; i.e., that position is redundant.

Indeed, tyrosine, tryptophan, phenylalanine and histidine at position 3 exhibited superior binding inhibition results as compared to threonine at that position. All five mixture sets were therefore carried forward for definition of the fourth and fifth positions.

For sets beginning Ac-Arg-Gly, when the third position is defined, the peptide sets that best inhibited binding of the mAb to the plate-bound polypeptide began Ac-Arg-Gly-Ile, Ac-Arg-Gly-Thr and Ac-Arg-Gly-Tyr, with the best starting Ac-Arg-Gly-Thr. It is thought that the threonine of that sequence corresponds to the threonine at the tenth position of the control polypeptide-mAb interaction, unlike the threonine at the ninth position.

For sets beginning Ac-Gln-Glu, when the third position is defined, the oligopeptide mixture sets that inhibited mAb binding began Ac-Gln-Glu-Cys, Ac-Gln-Glu-Phe, Ac-Gln-Glu-Thr and Ac-Gln-Glu-Tyr, with the set beginning Ac-Gln-Glu-Phe exhibiting the best inhibition of binding. Again, these oligopeptide mixture sets are of interest because they bear no apparent relation to the immunizing peptide.

Continuing the definition for the five sets beginning Ac-Gly-Arg, threonine was found best at position 4 and valine best at position 5, as are present in the native sequence. For these N-acylated C-amide mixtures having five defined positions and one mixed position, the order of inhibitory binding activity for sets with the above third position residues was: tyrosine>tryptophan>phenylalanine>histidine>threonine. The sixth position residue(s) for each set is (are) currently being defined.

For the set beginning Ac-Arg-Gly-Thr, valine at position 4 was most effective, and phenylalanine was thereafter found best for position 5. The sixth position is currently being defined.

For the set beginning Ac-Gln-Glu-Phe, histidine at position 4 and serine at position 5 provided effective inhibitors. The sixth position for this set is also being determined.

EXAMPLE 5

Antifungal Activity Against Candida Albicans

Antifungal studies were carried out *Candida albicans* ATCC 10231 as the target microbe. The yeast culture was spread onto YM agar plates and incubated at 30° C. for 48 hours. Three colonies of this culture (about 1 mm in diameter each) were then inoculated in 5 ml of 1 X PBS solution. The suspension was vortexed and diluted 10-fold in YM broth, for an approximate final concentration of $10^5$ to $5\times10^5$ CFU (colony forming units)/ml.

Actual concentrations of yeast cultures were determined by plating 100 μl of different solutions of the culture solution ($10^{-3}$, $10^{-4}$ and $10^{-5}$) onto solid YM agar plates. After 48 hours of incubation at 30° C., CFU formed were counted from each plate.

The assays were carried out in 96-well tissue culture plates. Eight wells containing only medium of YM broth served as negative controls, whereas eight wells containing medium and yeast culture served as positive controls. These controls were used to detect possible medium contamination and to provide a measure of uninhibited growth of the yeast. Two antifungal drugs Amphotericin 8 and Nystatin were included in each assay for comparative purposes.

For screening studies, oligopeptide mixtures were added to the yeast suspension in duplicates to reach a final concentration of 1.5 mg/ml. For MIC (minimum inhibitory concentration, the concentration necessary to inhibit 100 growth of the yeast) or IC-50 (concentration necessary to inhibit 50 growth of the yeast) peptides were added to the yeast suspension at concentrations derived from two-fold dilutions ranging from 1500 μg/ml to 3.13 μg/ml. The plates were incubated over a period of 48 hours at 30° C., and the optical density (OD) at 24 and 48 hours was determined at 620 nm.

The two different sets of 400 peptide mixtures, one composed of L-amino acids and the other of D-amino acids, were assayed against *C. albicans* at a concentration of about 1.5 mg/ml, as estimated by the radioactivity contained in the N-acetyl group. These peptides contained formylated tryptophan and methionine sulfoxide rather than the deprotected residues.

For the L-amino acid library, 20 mixtures of the first 400 mixtures of N-acetyl C-amide, 6-mer oligopeptide mixtures with four C-terminal positions occupied by equimolar mixtures inhibited more than 80 percent growth of the yeast after 48 hours. The lowest IC-50 values were found for mixtures that began Ac-Thr-Arg, Ac-Gln-Tyr and Ac-Arg-Met. Those three sets were moved forward for definition of the remaining positions of the 6-mer.

Following the procedures discussed in the previous examples, but using the assay above, several 6- and 7-mer peptides active against *S. aureus* were identified that exhibited MIC values in the 30–70 μg/ml range and/or an IC-50 value of about 35 μg/ml or less when assayed against *C. albicans*. Those peptides are listed below in Table 9.

TABLE 9

| Six- and Seven-Mer L-Amino Acid Peptides That Inhibit Growth of *C. albicans* | | | |
|---|---|---|---|
| Peptide* | IC-50 (μg/ml) | MIC (μg/ml) | SEQ ID NO: |
| RRWWCR | 31.46 | 70–140 | 48 |
| RRWWRR | 27.6 | 30–42 | 78 |
| RRWWRH | 30.1 | 40–80 | 79 |
| RRWWCVR | 50 | 50–62 | 80 |
| RRWWRFR | 45 | 50–62 | 77 |
| RRWWRFK | 46 | 50–62 | 81 |
| KRRWWRF | 40 | 45–62 | 82 |
| Controls | | | |
| Amphotericin B | 0.5 | 2–4 | |
| Nystatin | 1.0 | 2–4 | |

*N-acetyl C-amide peptides were used.

Work using a series of sets using N-acetyl C-amide all D-amino acid residues has begun using the previously discussed general method and assay discussed above. Here, the first screening utilized 400 sets of mixtures whose first two positions were defined and whose C-terminal four positions were occupied by equimolar mixtures. Twenty-seven sets that inhibited 100 percent growth after incubation for 48 hours were determined. Of those sets, the four sets exhibiting the lowest IC-50 values were carried forward to define the third position. Those four sets began: Ac-D-Leu-D-Arg, Ac-D-Arg-D-Arg, Ac-D-Trp-D-Arg, and Ac-D-Tyr-D-Arg.

EXAMPLE 6

Antimicrobial Activity Against *Streptococcus Sanguis*

*Streptococcus sanguis* ATCC 10556 [Gram-positive (+) bacteria present in tooth crevices] was grown overnight at 37° C. in Brain Heart Infusion (BHI) broth. This culture was reinoculated and incubated at 37° C. to reach the exponential phase of bacterial growth; i.e., a final bacterial suspension containing $10^5$ to $5 \times 10^5$ colony-forming units (CFU)/ml. The concentration of cells was established by plating 100 μl of different dilutions of the culture solution (e.g., $10^{-2}$, $10^{-3}$ and $10^{-4}$) onto solid agar plates. Following an overnight (about 18 hour) incubation at 37° C., the CFU thus formed were counted on each agar plate.

In 96-well tissue culture plates, as control blanks, eight wells per plate contained only medium, while as a positive growth control, eight other wells contained medium plus cells. These controls were used to detect possible medium contamination and to provide a measure of uninhibited growth of the microorganisms. For screening studies, peptide mixtures were added to the bacterial suspension to reach a final concentration of about 1.5 mg/ml. The plates were incubated overnight (about 18 hours) at 37° C., and the optical density (OD) determined at 620 nm after 20 to 24 hours incubation.

The same 400 mixture sets L-amino acids used in Example 5 were screened against *S. sanguis*. Fourteen sequences inhibited more than 80 percent of the growth of the bacteria after 24 hours of incubation at 37° C. The mixtures beginning Ac-Phe-Arg, Ac-Lys-Phe, Ac-Lys-Trp, Ac-Leu-Lys and Ac-Arg-Trp inhibited 100 percent of the growth of the bacteria. Definition of the remaining 6-mer positions is underway.

EXAMPLE 7

Antiviral Activity Against Herpes Simplex Virus Type 1 (HSV-1)

D- and L-amino acid libraries of peptide mixtures each containing 400 individual six-residue peptide mixture sets, with the first two positions defined and the last four as equimolar mixtures were used to begin studies on inhibiting growth of an exemplary virus. Both libraries were assayed against Herpes Simplex Virus Type 1 (HSV-1).

The screenings utilized a plaque assay in which 24-well plates containing Vero (monkey kidney) cell monolayers were overlaid with 400 μg/ml of each peptide or mixture in M-199V (medium and newborn calf serum). The plates were incubated for two hours at 37° C. Each well then received 0.1 ml of HSV-1 suspension at a multiplicity of infection (MOI) of 50, and the plate was again incubated for two hours [a control well of Vero cells with no peptide and an MOI of 50 showed approximately 50 plaques, which represent 50 virus particles or plaque forming units (PFU's)].

Each well was thereafter aspirated and immediately overlaid with 400 μg of peptide or mixture in DMEM-O (Dulbeco's modified Eagle's medium and pooled human gamma globulin) and incubated for 48 hours. Cell monolayers were observed for toxicity at 24 hours and 46 hours as compared to cell controls. At 48 hours, the plate wells were aspirated, rinsed, fixed and stained. Plaque formation, if present, was tallied and recorded.

The PFU's per well of six controls were averaged and represent 100 percent plaque formation at approximately 50 PFU's per well. The average PFU's per screened peptide or mixture (duplicate wells) quantitatively represented percent viral inhibition of plaque formation or infection. For example, a count of 10 PFU's of a screened peptide compared to the control of 50 PFU's would represent 20 percent plaque formation and 80 percent plaque inhibition.

Of 400 starting mixture sets, two N-acetyl C-amide L-peptide mixtures resulted in 100 percent inhibition with no cell toxicity. Three other L-peptide mixtures resulted in 100 percent inhibition with cell toxicity. Nineteen mixtures ranged from 79–99 percent inhibition with no cell toxicity and three with cell toxicity. The remaining peptide mixtures resulted in little or no viral inhibition. Overall, the L-amino acid library was significantly less active as compared to the D-amino acid library, discussed hereinafter.

The five peptide mixture sets that resulted in 100 percent inhibition and an additional nine mixtures chosen by high percent inhibition, relative cell toxicity, and other criteria (i.e., small vs. large plaque formation) were titrated at 50, 100, 200, 300 μg/ml in dual wells as per protocol. The six most active mixture sets with two identified portions found by titration began, from high activity to low: Ac-Trp-Trp, Ac-Cys-Cys, Ac-Trp-Cys, Ac-Trp-Leu, Ac-Trp-Lys, and Ac-Arg-Trp. Mixture sets beginning Ac-Trp-Trp and Ac-Cys-Cys showed 65 percent and 40 percent inhibition, respectively. The peptide mixture beginning Ac-Arg-Trp exhibited 100 percent inhibition at 300 μg/ml and 81 percent inhibition at 200 μg/ml. Further studies are underway to identify each position of the 6-mer sequences.

Two twenty L-peptide mixtures having five N-terminal defined positions and twenty predetermined residues at position 6 that exhibited both selective antibacterial and antifungal properties (discussed previously herein) have also been screened in this assay. Exemplary results of those assays are shown in Table 10, below, for those individual 6-mer sequences that exhibited 100 percent inhibition at one or five μg/ml.

TABLE 10

Herpes Simplex Virus Plaque Inhibition by Individual Six-Mer L-Peptides

| Peptide for 100 Percent Inhibition* | Toxic Concentration | SEQ ID NO: |
|---|---|---|
| At 1 μg/ml | | |
| RRWWCA | 25 μg/ml | 56 |
| RRWWCG | 10 μg/ml | 83 |
| RRWWRR | 25 μg/ml | 78 |
| RRWWRW | 25 μg/ml | 84 |
| RRWWCC | 10 μg/ml | 85 |
| RRWWCM | 10 μg/ml | 86 |
| At 5 μg/ml | | |
| RRWWCF | 10 μg/ml | 87 |
| RRWWCK | 10 μg/ml | 52 |

*N-acetyl C-amide peptides were used.

Twenty-six N-acetyl C-amide all D-peptide mixtures having positions 1 and 2 defined and positions 3–6 occupied by mixtures resulted in 100 percent inhibition with no cell toxicity. Fourteen mixtures resulted in 100 percent inhibition with cell toxicity. The remaining peptides ranged from 0–99 percent inhibition with and without cell toxicity. All 40 peptides with 100 percent inhibition were titrated at 50, 100, 200 and 400 μg/ml in dual wells as per protocol.

The peptide mixtures beginning Ac-D-Leu-D-Arg, Ac-D-Lys-D-Trp, Ac-D-Lys-D-Cys and Ac-D-Cys-D-Arg all resulted in 100 percent viral inhibition at 100, 200 and 400 μg/ml. At 50 μg/ml, these mixtures resulted in 67 percent, 46 percent, 60 percent and 56 percent inhibition, respectively. These four mixtures all showed cell toxicity at 400 μg/ml. Mixtures beginning Ac-D-Leu-D-Arg and Ac-D-Cys-D-Arg showed moderate toxicity at 200 μg/ml. At all remaining concentrations, no toxicity was evident. These four most active peptide mixtures are being carried forward for definition of the remaining positions.

EXAMPLE 8

Inhibition of binding by Monoclonal Antibody 19B10

Monoclonal antibody mAb 19B10 had previously been raised against a synthetic polypeptide representing residues 78–110 of the hemagglutinin protein of influenza virus. [Houghten et al., *Vaccines* 1986, pages 21–25 (1987); Appel et al., *J. Immunol.,* 144:976–983 (1990).] Detailed mapping of the peptide-mAb interaction, as well as the relative positional importance of each residue of the antigenic determinant had also been determined as was done in Example 2.

The antigenic determinant recognized by mAb 19B10 has the sequence Asp-Val-Pro-Asp-Tyr-Ala (SEQ ID NO:88). Oligopeptide mixture sets were assayed to determine their ability to inhibit the interaction of mAb 19B10 with the 13-residue peptide Ac-Tyr-Pro-Tyr-Asp-Val-Pro-Asp-Tyr-Ala-Ser-Leu-Arg-Ser-$NH_2$ (SEQ ID NO:89) adsorbed to a microtiter plate in competitive ELISA assays.

Oligopeptide sets were screened in the general manner discussed previously, except that rather than using 400 mixture sets whose first two positions were defined and whose last four were equimolar mixtures for the first screen, 324 such N-acetyl C-amide sets were used based on mixtures of eighteen amino acids. Tryptophan and cysteine were not included with these mixture.

Each of those 324 mixture sets contained about 104,976 hexapeptides ($18^4$). The whole library of 324 sets contained about 34,012,224 6-mer peptides.

The mixture set beginning Ac-Asp-Val showed the greatest activity (lowest IC-50 value) and was used to go forward in defining the remaining sets.

A twenty-member mixture set was used to determine the third position. Tryptophan was again omitted from the mixture positions, but was included in the twenty different sets, each set containing a mixture of 6,859 different peptides ($19^3$).

The same process was repeated until each of the six positions of the N-acetyl C-amide 6-mer was determined. That 6-mer had the sequence Ac-Asp-Val-Pro-Asp-Tyr-Ala-NH$_2$ (SEQ ID NO:90), the sequence of the 6-mer antigenic determinant.

IC-50 Values decreased as follows, as the positions were defined: positions 1 and 2=250 μM; position 3=41 μM; position 5=0.38 μM; and position 6=0.03 μM.

A similar study with the same mAb started with 400 N-acetyl C-amide mixture sets whose first two positions were defined by the twenty naturally occurring amino acid residues and whose mixture positions were occupied by mixtures of nineteen amino acids, tryptophan excluded. Each of those 400 sets therefore contained 130,321 individual hexamers ($19^4$). The library created by those 400 mixture sets therefore contained 52,128,400 6-mer peptides (400×130,321). This library therefore contained almost 20 million more peptides than did the first discussed library.

This 400 member library of mixture sets was screened as discussed above. The same mixtures determined using the smaller library were found to cause significant inhibition, as did three other mixtures that bore no resemblance to the epitope. Those three sequences began Ac-Ala-Thr, Ac-Tyr-Thr and Ac-His-Asp. Further work is underway to determine the remaining best binding positions of those three mixture sets.

EXAMPLE 9

Inhibition of Binding Monoclonal Antibody mAb #2

Binding inhibition by mixture sets of a monoclonal antibody raised against the major surface antigen of hepatitis B virus (HBsAg) using a monoclonal antibody denominated mAb #2. (A gift from Dr. David Milich, The Scripps Research Institute, La Jolla, Calif.) That monoclonal binds to the 6-mer antigenic determinant Ser-Thr-Thr-Ser-Thr-Gly (SEQ ID NO:91).

Four hundred N-acetyl C-amide mixture sets whose first two defined positions were selected from each of the twenty natural amino acid residues and whose four reamining mixture positions contained equimolar mixtures of nineteen amino acid residues (tryptophan excluded) were again used here. A competitive ELISA assay was again used as the screen with the protein antigen HBsAg being adsorbed to the microtiter plates.

The two best binding sets began Ac-Leu-Thr and Ac-Gln-Thr, sequences different from the native antigenic determinant. The third position best binding residue for both sets was threonine, whereas the fourth position best binding residue for both sets was serine.

Thus, a sequence containing three of four residues in both sets were identical to the sequence of the native epitope. Work is underway to define the fifth and sixth positions for each mixture set.

It will be evident that there are a large number of embodiments of the invention which, while not specifically described above, are clearly within the scope and spirit of the invention. Consequently the description above is to be considered merely exemplary, and the invention is to be defined and limited solely by the appended claims.

---

We claim:

1. An oligopeptide having up to 10 amino acid residues comprising a sequence selected from the group consisting of Phe-Arg-Trp-Leu-Leu-Xaa (SEQ ID NO:10); Phe-Arg-Trp-Trp-His-Xaa (SEQ ID NO:11); Arg-Arg-Trp-Trp-Met-Xaa (SEQ ID NO:12); Arg-Arg-Trp-Trp-Cys-Xaa (SEQ ID NO:13); and Arg-Arg-Trp-Trp-Arg-Xaa (SEQ ID NO:14), wherein Xaa is another amino acid residue.

2. The oligopeptide according to claim 1 further including an N-terminal $C_1$-$C_8$ acyl group and a C-terminal amido group.

3. The oligopeptide according to claim 2 wherein Xaa is any of the twenty natural amino acids other than aspartic acid, glutamic acid and glycine.

4. The oligopeptide according to claim 1 that includes a sequence having a SEQ ID NO selected from the group consisting of 5, 16–25, 26–42, 43–47, 48–61, 63–69, 70–77, 78–82, 83–87, and 62.

5. The oligopeptide according to claim 4 that includes a N-terminal acetyl group and a C-terminal amide group.

* * * * *

SEQUENCE LISTING ( 1 ) GENERAL INFORMATION:

( i i i ) NUMBER OF SEQUENCES: 91

( 2 ) INFORMATION FOR SEQ ID NO:1:

( i ) SEQUENCE CHARACTERISTICS:
        ( A ) LENGTH: 13 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:1:

Gly  Ala  Ser  Pro  Tyr  Pro  Asn  Leu  Ser  Asn  Gln  Gln  Thr
    1                      5                                10

( 2 ) INFORMATION FOR SEQ ID NO:2:

( i ) SEQUENCE CHARACTERISTICS:
        ( A ) LENGTH: 6 amino acids
        ( B ) TYPE: amino acid -continued (C) STRANDEDNESS: single
                (D) TOPOLOGY: linear (ii) MOLECULE TYPE: peptide (xi) SEQUENCE DESCRIPTION: SEQ ID NO:2:

Pro  Tyr  Pro  Asn  Leu  Ser
        1                        5

(2) INFORMATION FOR SEQ ID NO:3:

(i) SEQUENCE CHARACTERISTICS:
                (A) LENGTH: 4 amino acids
                (B) TYPE: amino acid
                (C) STRANDEDNESS: single
                (D) TOPOLOGY: linear (ii) MOLECULE TYPE: peptide (xi) SEQUENCE DESCRIPTION: SEQ ID NO:3:

Tyr  Pro  Asn  Leu
        1

(2) INFORMATION FOR SEQ ID NO:4:

(i) SEQUENCE CHARACTERISTICS:
                (A) LENGTH: 6 amino acids
                (B) TYPE: amino acid
                (C) STRANDEDNESS: single
                (D) TOPOLOGY: linear (ii) MOLECULE TYPE: peptide (ix) FEATURE:
                (A) NAME/KEY: Modified-site
                (B) LOCATION: 1
                (D) OTHER INFORMATION: /label=Xaa
                        / note="Xaa is N-acetyl tyrosine."

(ix) FEATURE:
                (A) NAME/KEY: Modified-site
                (B) LOCATION: 6
                (D) OTHER INFORMATION: /label=Xaa
                        / note="Xaa is asparagine amide."

(xi) SEQUENCE DESCRIPTION: SEQ ID NO:4:

Xaa  Pro  Asn  Leu  Ser  Xaa
        1                        5

(2) INFORMATION FOR SEQ ID NO:5:

(i) SEQUENCE CHARACTERISTICS:
                (A) LENGTH: 6 amino acids
                (B) TYPE: amino acid
                (C) STRANDEDNESS: single
                (D) TOPOLOGY: linear (ii) MOLECULE TYPE: peptide (ix) FEATURE:
                (A) NAME/KEY: Modified-site
                (B) LOCATION: 1
                (D) OTHER INFORMATION: /label=Xaa
                        / note="Xaa is N-acetyl arginine."

(ix) FEATURE:
                (A) NAME/KEY: Modified-site
                (B) LOCATION: 6
                (D) OTHER INFORMATION: /label=Xaa
                        / note="Xaa is arginine amide."

(xi) SEQUENCE DESCRIPTION: SEQ ID NO:5:

Xaa  Arg  Trp  Trp  Cys  Xaa

```
                1                           5
```

(2) INFORMATION FOR SEQ ID NO:6:

(i) SEQUENCE CHARACTERISTICS:
        (A) LENGTH: 14 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:6:

```
Leu His Asn Asn Glu Ala Gly Arg Thr Thr Val Phe Ser Cys
1               5                   10
```

(2) INFORMATION FOR SEQ ID NO:7:

(i) SEQUENCE CHARACTERISTICS:
        (A) LENGTH: 7 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:7:

```
Gly Arg Thr Thr Val Phe Ser
1               5
```

(2) INFORMATION FOR SEQ ID NO:8:

(i) SEQUENCE CHARACTERISTICS:
        (A) LENGTH: 5 amino acids
        (B) TYPE: amino acid
        (D) TOPOLOGY: linear (ii) MOLECULE TYPE: peptide (xi) SEQUENCE DESCRIPTION: SEQ ID NO:8:

```
Arg Arg Trp Trp Cys
1               5
```

(2) INFORMATION FOR SEQ ID NO:9:

(i) SEQUENCE CHARACTERISTICS:
        (A) LENGTH: 6 amino acids
        (B) TYPE: amino acid
        (D) TOPOLOGY: linear (ii) MOLECULE TYPE: peptide (ix) FEATURE:
        (A) NAME/KEY: Modified-site
        (B) LOCATION: 1
        (D) OTHER INFORMATION: /label=Xaa
            / note="Xaa is N-acetyl arginine."

(ix) FEATURE:
        (A) NAME/KEY: Modified-site
        (B) LOCATION: 6
        (D) OTHER INFORMATION: /label=Xaa
            / note="Xaa is any of the twenty natural amino
            acids other than aspartic acid, glutamic acid or
            glycine, which are modified by N-acetylation."

(xi) SEQUENCE DESCRIPTION: SEQ ID NO:9:

```
Xaa Arg Trp Trp Cys Xaa
1               5
```

(2) INFORMATION FOR SEQ ID NO:10:

( i ) SEQUENCE CHARACTERISTICS:
      ( A ) LENGTH: 6 amino acids
      ( B ) TYPE: amino acid
      ( D ) TOPOLOGY: linear ( i i ) MOLECULE TYPE: peptide ( i x ) FEATURE:
      ( A ) NAME/KEY: Modified-site
      ( B ) LOCATION: 6
      ( D ) OTHER INFORMATION: /label=Xaa
            / note="Xaa is another amino acid residue."

( x i ) SEQUENCE DESCRIPTION: SEQ ID NO:10:

Phe Arg Trp Leu Leu Xaa
1               5

( 2 ) INFORMATION FOR SEQ ID NO:11:

( i ) SEQUENCE CHARACTERISTICS:
      ( A ) LENGTH: 6 amino acids
      ( B ) TYPE: amino acid
      ( D ) TOPOLOGY: linear ( i i ) MOLECULE TYPE: peptide ( i x ) FEATURE:
      ( A ) NAME/KEY: Modified-site
      ( B ) LOCATION: 6
      ( D ) OTHER INFORMATION: /label=Xaa
            / note="Xaa is another amino acid residue."

( x i ) SEQUENCE DESCRIPTION: SEQ ID NO:11:

Phe Arg Trp Trp His Xaa
1               5

( 2 ) INFORMATION FOR SEQ ID NO:12:

( i ) SEQUENCE CHARACTERISTICS:
      ( A ) LENGTH: 6 amino acids
      ( B ) TYPE: amino acid
      ( D ) TOPOLOGY: linear ( i i ) MOLECULE TYPE: peptide ( i x ) FEATURE:
      ( A ) NAME/KEY: Modified-site
      ( B ) LOCATION: 6
      ( D ) OTHER INFORMATION: /label=Xaa
            / note="Xaa is another amino acid residue."

( x i ) SEQUENCE DESCRIPTION: SEQ ID NO:12:

Arg Arg Trp Trp Met Xaa
1               5

( 2 ) INFORMATION FOR SEQ ID NO:13:

( i ) SEQUENCE CHARACTERISTICS:
      ( A ) LENGTH: 6 amino acids
      ( B ) TYPE: amino acid
      ( D ) TOPOLOGY: linear ( i i ) MOLECULE TYPE: peptide ( i x ) FEATURE:
      ( A ) NAME/KEY: Modified-site
      ( B ) LOCATION: 6
      ( D ) OTHER INFORMATION: /label=Xaa
            / note="Xaa is another amino acid residue."

( x i ) SEQUENCE DESCRIPTION: SEQ ID NO:13:

Arg Arg Trp Trp Cys Xaa ( 2 ) INFORMATION FOR SEQ ID NO:14:

( i ) SEQUENCE CHARACTERISTICS:
        ( A ) LENGTH: 6 amino acids
        ( B ) TYPE: amino acid
        ( D ) TOPOLOGY: linear ( i i ) MOLECULE TYPE: peptide ( i x ) FEATURE:
        ( A ) NAME/KEY: Modified-site
        ( B ) LOCATION: 6
        ( D ) OTHER INFORMATION: /label=Xaa
            / note="Xaa is another amino acid residue."

( x i ) SEQUENCE DESCRIPTION: SEQ ID NO:14:

Arg Arg Trp Trp Arg Xaa
1               5

( 2 ) INFORMATION FOR SEQ ID NO:15:

( i ) SEQUENCE CHARACTERISTICS:
        ( A ) LENGTH: 6 amino acids
        ( B ) TYPE: amino acid
        ( D ) TOPOLOGY: linear ( i i ) MOLECULE TYPE: peptide ( i x ) FEATURE:
        ( A ) NAME/KEY: Modified-site
        ( B ) LOCATION: 1
        ( D ) OTHER INFORMATION: /label=Xaa
            / note="Xaa is N-acetyl proline."

( i x ) FEATURE:
        ( A ) NAME/KEY: Modified-site
        ( B ) LOCATION: 6
        ( D ) OTHER INFORMATION: /label=Xaa
            / note="Xaa is serine amide."

( x i ) SEQUENCE DESCRIPTION: SEQ ID NO:15:

Xaa Tyr Pro Asn Leu Xaa
1               5

( 2 ) INFORMATION FOR SEQ ID NO:16:

( i ) SEQUENCE CHARACTERISTICS:
        ( A ) LENGTH: 6 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:16:

Phe Arg Trp Leu Leu Arg
1               5

( 2 ) INFORMATION FOR SEQ ID NO:17:

( i ) SEQUENCE CHARACTERISTICS:
        ( A ) LENGTH: 6 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:17:

Phe Arg Trp Leu Leu Lys
1               5

( 2 ) INFORMATION FOR SEQ ID NO:18:

( i ) SEQUENCE CHARACTERISTICS:
        ( A ) LENGTH: 6 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:18:

```
Phe  Arg  Trp  Leu  Leu  His
1                   5
```

( 2 ) INFORMATION FOR SEQ ID NO:19:

( i ) SEQUENCE CHARACTERISTICS:
        ( A ) LENGTH: 6 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:19:

```
Phe  Arg  Trp  Leu  Leu  Val
1                   5
```

( 2 ) INFORMATION FOR SEQ ID NO:20:

( i ) SEQUENCE CHARACTERISTICS:
        ( A ) LENGTH: 6 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:20:

```
Phe  Arg  Trp  Trp  His  Arg
1                   5
```

( 2 ) INFORMATION FOR SEQ ID NO:21:

( i ) SEQUENCE CHARACTERISTICS:
        ( A ) LENGTH: 6 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:21:

```
Phe  Arg  Trp  Trp  His  Lys
1                   5
```

( 2 ) INFORMATION FOR SEQ ID NO:22:

( i ) SEQUENCE CHARACTERISTICS:
        ( A ) LENGTH: 6 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:22:

```
Phe  Arg  Trp  Trp  His  Trp
1                   5
```

( 2 ) INFORMATION FOR SEQ ID NO:23:

( i ) SEQUENCE CHARACTERISTICS:
        ( A ) LENGTH: 6 amino acids (B) TYPE: amino acid
(D) TOPOLOGY: linear (ii) MOLECULE TYPE: peptide (xi) SEQUENCE DESCRIPTION: SEQ ID NO:23:

Phe Arg Trp Trp His Phe
1               5

(2) INFORMATION FOR SEQ ID NO:24:

(i) SEQUENCE CHARACTERISTICS:
  (A) LENGTH: 6 amino acids
  (B) TYPE: amino acid
  (D) TOPOLOGY: linear (ii) MOLECULE TYPE: peptide (xi) SEQUENCE DESCRIPTION: SEQ ID NO:24:

Phe Arg Trp Trp His His
1               5

(2) INFORMATION FOR SEQ ID NO:25:

(i) SEQUENCE CHARACTERISTICS:
  (A) LENGTH: 6 amino acids
  (B) TYPE: amino acid
  (D) TOPOLOGY: linear (ii) MOLECULE TYPE: peptide (xi) SEQUENCE DESCRIPTION: SEQ ID NO:25:

Phe Arg Trp Trp His Leu
1               5

(2) INFORMATION FOR SEQ ID NO:26:

(i) SEQUENCE CHARACTERISTICS:
  (A) LENGTH: 6 amino acids
  (B) TYPE: amino acid
  (D) TOPOLOGY: linear (ii) MOLECULE TYPE: peptide (xi) SEQUENCE DESCRIPTION: SEQ ID NO:26:

Arg Arg Trp Trp Met Arg
1               5

(2) INFORMATION FOR SEQ ID NO:27:

(i) SEQUENCE CHARACTERISTICS:
  (A) LENGTH: 6 amino acids
  (B) TYPE: amino acid
  (D) TOPOLOGY: linear (ii) MOLECULE TYPE: peptide (xi) SEQUENCE DESCRIPTION: SEQ ID NO:27:

Arg Arg Trp Trp Met Gly
1               5

(2) INFORMATION FOR SEQ ID NO:28:

(i) SEQUENCE CHARACTERISTICS:
  (A) LENGTH: 6 amino acids
  (B) TYPE: amino acid
  (D) TOPOLOGY: linear (ii) MOLECULE TYPE: peptide ( x i ) SEQUENCE DESCRIPTION: SEQ ID NO:28:

Arg Arg Trp Trp Met Ile
1               5

(2) INFORMATION FOR SEQ ID NO:29:

(i) SEQUENCE CHARACTERISTICS:
    (A) LENGTH: 6 amino acids
    (B) TYPE: amino acid
    (D) TOPOLOGY: linear (i i) MOLECULE TYPE: peptide (x i) SEQUENCE DESCRIPTION: SEQ ID NO:29:

Arg Arg Trp Trp Met Cys
1               5

(2) INFORMATION FOR SEQ ID NO:30:

(i) SEQUENCE CHARACTERISTICS:
    (A) LENGTH: 6 amino acids
    (B) TYPE: amino acid
    (D) TOPOLOGY: linear (i i) MOLECULE TYPE: peptide (x i) SEQUENCE DESCRIPTION: SEQ ID NO:30:

Arg Arg Trp Trp Met Lys
1               5

(2) INFORMATION FOR SEQ ID NO:31:

(i) SEQUENCE CHARACTERISTICS:
    (A) LENGTH: 6 amino acids
    (B) TYPE: amino acid
    (D) TOPOLOGY: linear (i i) MOLECULE TYPE: peptide (x i) SEQUENCE DESCRIPTION: SEQ ID NO:31:

Arg Arg Trp Trp Met Leu
1               5

(2) INFORMATION FOR SEQ ID NO:32:

(i) SEQUENCE CHARACTERISTICS:
    (A) LENGTH: 6 amino acids
    (B) TYPE: amino acid
    (D) TOPOLOGY: linear (i i) MOLECULE TYPE: peptide (x i) SEQUENCE DESCRIPTION: SEQ ID NO:32:

Arg Arg Trp Trp Met Tyr
1               5

(2) INFORMATION FOR SEQ ID NO:33:

(i) SEQUENCE CHARACTERISTICS:
    (A) LENGTH: 6 amino acids
    (B) TYPE: amino acid
    (D) TOPOLOGY: linear (i i) MOLECULE TYPE: peptide (x i) SEQUENCE DESCRIPTION: SEQ ID NO:33:

Arg Arg Trp Trp Met Val
1               5

( 2 ) INFORMATION FOR SEQ ID NO:34:

( i ) SEQUENCE CHARACTERISTICS:
        ( A ) LENGTH: 6 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:34:

Arg Arg Trp Trp Met Trp
    1                    5

( 2 ) INFORMATION FOR SEQ ID NO:35:

( i ) SEQUENCE CHARACTERISTICS:
        ( A ) LENGTH: 6 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:35:

Arg Arg Trp Trp Met Ser
    1                    5

( 2 ) INFORMATION FOR SEQ ID NO:36:

( i ) SEQUENCE CHARACTERISTICS:
        ( A ) LENGTH: 6 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:36:

Arg Arg Trp Trp Met Thr
    1                    5

( 2 ) INFORMATION FOR SEQ ID NO:37:

( i ) SEQUENCE CHARACTERISTICS:
        ( A ) LENGTH: 6 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:37:

Arg Arg Trp Trp Met Met
    1                    5

( 2 ) INFORMATION FOR SEQ ID NO:38:

( i ) SEQUENCE CHARACTERISTICS:
        ( A ) LENGTH: 6 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:38:

Arg Arg Trp Trp Met Ala
    1                    5

( 2 ) INFORMATION FOR SEQ ID NO:39:

( i ) SEQUENCE CHARACTERISTICS:
        ( A ) LENGTH: 6 amino acids ( B ) TYPE: amino acid
        ( D ) TOPOLOGY: linear ( i i ) MOLECULE TYPE: peptide ( x i ) SEQUENCE DESCRIPTION: SEQ ID NO:39:

Arg  Arg  Trp  Trp  Met  Phe
    1                   5

( 2 ) INFORMATION FOR SEQ ID NO:40:

( i ) SEQUENCE CHARACTERISTICS:
        ( A ) LENGTH: 6 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:40:

Arg  Arg  Trp  Trp  Met  His
    1                   5

( 2 ) INFORMATION FOR SEQ ID NO:41:

( i ) SEQUENCE CHARACTERISTICS:
        ( A ) LENGTH: 6 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:41:

Arg  Arg  Trp  Trp  Met  Asn
    1                   5

( 2 ) INFORMATION FOR SEQ ID NO:42:

( i ) SEQUENCE CHARACTERISTICS:
        ( A ) LENGTH: 6 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:42:

Arg  Arg  Trp  Trp  Met  Pro
    1                   5

( 2 ) INFORMATION FOR SEQ ID NO:43:

( i ) SEQUENCE CHARACTERISTICS:
        ( A ) LENGTH: 6 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:43:

Phe  Arg  Trp  Leu  Leu  Phe
    1                   5

( 2 ) INFORMATION FOR SEQ ID NO:44:

( i ) SEQUENCE CHARACTERISTICS:
        ( A ) LENGTH: 6 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:44:

Phe Arg Trp Leu Leu Trp
1               5

( 2 ) INFORMATION FOR SEQ ID NO:45:

( i ) SEQUENCE CHARACTERISTICS:
    ( A ) LENGTH: 6 amino acids
    ( B ) TYPE: amino acid
    ( D ) TOPOLOGY: linear ( i i ) MOLECULE TYPE: peptide ( x i ) SEQUENCE DESCRIPTION: SEQ ID NO:45:

Phe Arg Trp Leu Leu Cys
1               5

( 2 ) INFORMATION FOR SEQ ID NO:46:

( i ) SEQUENCE CHARACTERISTICS:
    ( A ) LENGTH: 6 amino acids
    ( B ) TYPE: amino acid
    ( D ) TOPOLOGY: linear ( i i ) MOLECULE TYPE: peptide ( x i ) SEQUENCE DESCRIPTION: SEQ ID NO:46:

Phe Arg Trp Leu Leu Leu
1               5

( 2 ) INFORMATION FOR SEQ ID NO:47:

( i ) SEQUENCE CHARACTERISTICS:
    ( A ) LENGTH: 6 amino acids
    ( B ) TYPE: amino acid
    ( D ) TOPOLOGY: linear ( i i ) MOLECULE TYPE: peptide ( x i ) SEQUENCE DESCRIPTION: SEQ ID NO:47:

Phe Arg Trp Trp His Ile
1               5

( 2 ) INFORMATION FOR SEQ ID NO:48:

( i ) SEQUENCE CHARACTERISTICS:
    ( A ) LENGTH: 6 amino acids
    ( B ) TYPE: amino acid
    ( D ) TOPOLOGY: linear ( i i ) MOLECULE TYPE: peptide ( x i ) SEQUENCE DESCRIPTION: SEQ ID NO:48:

Arg Arg Trp Trp Cys Arg
1               5

( 2 ) INFORMATION FOR SEQ ID NO:49:

( i ) SEQUENCE CHARACTERISTICS:
    ( A ) LENGTH: 6 amino acids
    ( B ) TYPE: amino acid
    ( D ) TOPOLOGY: linear ( i i ) MOLECULE TYPE: peptide ( x i ) SEQUENCE DESCRIPTION: SEQ ID NO:49:

Arg Arg Trp Trp Cys Trp
1               5

( 2 ) INFORMATION FOR SEQ ID NO:50:

( i ) SEQUENCE CHARACTERISTICS:
        ( A ) LENGTH: 6 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:50:

Arg Arg Trp Trp Cys Val
1               5

( 2 ) INFORMATION FOR SEQ ID NO:51:

( i ) SEQUENCE CHARACTERISTICS:
        ( A ) LENGTH: 6 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:51:

Arg Arg Trp Trp Cys Tyr
1               5

( 2 ) INFORMATION FOR SEQ ID NO:52:

( i ) SEQUENCE CHARACTERISTICS:
        ( A ) LENGTH: 6 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:52:

Arg Arg Trp Trp Cys Lys
1               5

( 2 ) INFORMATION FOR SEQ ID NO:53:

( i ) SEQUENCE CHARACTERISTICS:
        ( A ) LENGTH: 6 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:53:

Arg Arg Trp Trp Cys Ser
1               5

( 2 ) INFORMATION FOR SEQ ID NO:54:

( i ) SEQUENCE CHARACTERISTICS:
        ( A ) LENGTH: 6 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:54:

Arg Arg Trp Trp Cys His
1               5

( 2 ) INFORMATION FOR SEQ ID NO:55:

( i ) SEQUENCE CHARACTERISTICS:
        ( A ) LENGTH: 6 amino acids ( B ) TYPE: amino acid
( D ) TOPOLOGY: linear ( i i ) MOLECULE TYPE: peptide ( x i ) SEQUENCE DESCRIPTION: SEQ ID NO:55:

Arg Arg Trp Trp Cys Thr
1               5

( 2 ) INFORMATION FOR SEQ ID NO:56:

( i ) SEQUENCE CHARACTERISTICS:
    ( A ) LENGTH: 6 amino acids
    ( B ) TYPE: amino acid
    ( D ) TOPOLOGY: linear ( i i ) MOLECULE TYPE: peptide ( x i ) SEQUENCE DESCRIPTION: SEQ ID NO:56:

Arg Arg Trp Trp Cys Ala
1               5

( 2 ) INFORMATION FOR SEQ ID NO:57:

( i ) SEQUENCE CHARACTERISTICS:
    ( A ) LENGTH: 6 amino acids
    ( B ) TYPE: amino acid
    ( D ) TOPOLOGY: linear ( i i ) MOLECULE TYPE: peptide ( x i ) SEQUENCE DESCRIPTION: SEQ ID NO:57:

Arg Arg Trp Trp Arg Phe
1               5

( 2 ) INFORMATION FOR SEQ ID NO:58:

( i ) SEQUENCE CHARACTERISTICS:
    ( A ) LENGTH: 6 amino acids
    ( B ) TYPE: amino acid
    ( D ) TOPOLOGY: linear ( i i ) MOLECULE TYPE: peptide ( x i ) SEQUENCE DESCRIPTION: SEQ ID NO:58:

Arg Arg Trp Trp Arg Cys
1               5

( 2 ) INFORMATION FOR SEQ ID NO:59:

( i ) SEQUENCE CHARACTERISTICS:
    ( A ) LENGTH: 6 amino acids
    ( B ) TYPE: amino acid
    ( D ) TOPOLOGY: linear ( i i ) MOLECULE TYPE: DNA (genomic)

( x i ) SEQUENCE DESCRIPTION: SEQ ID NO:59:

Arg Arg Trp Trp Arg Leu
1               5

( 2 ) INFORMATION FOR SEQ ID NO:60:

( i ) SEQUENCE CHARACTERISTICS:
    ( A ) LENGTH: 6 amino acids
    ( B ) TYPE: amino acid
    ( D ) TOPOLOGY: linear ( i i ) MOLECULE TYPE: peptide ( x i ) SEQUENCE DESCRIPTION: SEQ ID NO:60:

Arg Arg Trp Trp Arg Ile
1               5

( 2 ) INFORMATION FOR SEQ ID NO:61:

( i ) SEQUENCE CHARACTERISTICS:
        ( A ) LENGTH: 6 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:61:

Arg Arg Trp Trp Arg Ala
1               5

( 2 ) INFORMATION FOR SEQ ID NO:62:

( i ) SEQUENCE CHARACTERISTICS:
        ( A ) LENGTH: 6 amino acids
        ( B ) TYPE: amino acid
        ( D ) TOPOLOGY: linear ( i i ) MOLECULE TYPE: peptide ( i x ) FEATURE:
        ( A ) NAME/KEY: Modified-site
        ( B ) LOCATION: 1
        ( D ) OTHER INFORMATION: /label=Xaa
            / note="Xaa is N-acetyl arginine."

( i x ) FEATURE:
        ( A ) NAME/KEY: Modified-site
        ( B ) LOCATION: 6
        ( D ) OTHER INFORMATION: /label=Xaa
            / note="Xaa is phenylalanine amide."

( x i ) SEQUENCE DESCRIPTION: SEQ ID NO:62:

Xaa Arg Trp Trp Arg Xaa
1               5

( 2 ) INFORMATION FOR SEQ ID NO:63:

( i ) SEQUENCE CHARACTERISTICS:
        ( A ) LENGTH: 7 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:63:

Tyr Arg Arg Trp Trp Arg Phe
1               5

( 2 ) INFORMATION FOR SEQ ID NO:64:

( i ) SEQUENCE CHARACTERISTICS:
        ( A ) LENGTH: 7 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:64:

Ile Arg Arg Trp Trp Arg Phe
1               5

( 2 ) INFORMATION FOR SEQ ID NO:65:

( i ) SEQUENCE CHARACTERISTICS:
( A ) LENGTH: 7 amino acids
( B ) TYPE: amino acid
( D ) TOPOLOGY: linear ( i i ) MOLECULE TYPE: peptide ( x i ) SEQUENCE DESCRIPTION: SEQ ID NO:65:

Trp Arg Arg Trp Trp Arg Phe
1               5

( 2 ) INFORMATION FOR SEQ ID NO:66:

( i ) SEQUENCE CHARACTERISTICS:
( A ) LENGTH: 7 amino acids
( B ) TYPE: amino acid
( D ) TOPOLOGY: linear ( i i ) MOLECULE TYPE: peptide ( x i ) SEQUENCE DESCRIPTION: SEQ ID NO:66:

Phe Arg Arg Trp Trp Arg Phe
1               5

( 2 ) INFORMATION FOR SEQ ID NO:67:

( i ) SEQUENCE CHARACTERISTICS:
( A ) LENGTH: 7 amino acids
( B ) TYPE: amino acid
( D ) TOPOLOGY: linear ( i i ) MOLECULE TYPE: peptide ( x i ) SEQUENCE DESCRIPTION: SEQ ID NO:67:

Leu Arg Arg Trp Trp Arg Phe
1               5

( 2 ) INFORMATION FOR SEQ ID NO:68:

( i ) SEQUENCE CHARACTERISTICS:
( A ) LENGTH: 7 amino acids
( B ) TYPE: amino acid
( D ) TOPOLOGY: linear ( i i ) MOLECULE TYPE: peptide ( x i ) SEQUENCE DESCRIPTION: SEQ ID NO:68:

Cys Arg Arg Trp Trp Arg Phe
1               5

( 2 ) INFORMATION FOR SEQ ID NO:69:

( i ) SEQUENCE CHARACTERISTICS:
( A ) LENGTH: 7 amino acids
( B ) TYPE: amino acid
( D ) TOPOLOGY: linear ( i i ) MOLECULE TYPE: peptide ( x i ) SEQUENCE DESCRIPTION: SEQ ID NO:69:

Arg Arg Arg Trp Trp Arg Phe
1               5

( 2 ) INFORMATION FOR SEQ ID NO:70:

( i ) SEQUENCE CHARACTERISTICS:
( A ) LENGTH: 7 amino acids
( B ) TYPE: amino acid
( D ) TOPOLOGY: linear ( i i ) MOLECULE TYPE: peptide ( x i ) SEQUENCE DESCRIPTION: SEQ ID NO:70:

```
Arg Arg Trp Trp Arg Phe Trp
1               5
```

( 2 ) INFORMATION FOR SEQ ID NO:71:

( i ) SEQUENCE CHARACTERISTICS:
        ( A ) LENGTH: 7 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:71:

```
Arg Arg Trp Trp Arg Phe Phe
1               5
```

( 2 ) INFORMATION FOR SEQ ID NO:72:

( i ) SEQUENCE CHARACTERISTICS:
        ( A ) LENGTH: 7 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:72:

```
Arg Arg Trp Trp Arg Phe Leu
1               5
```

( 2 ) INFORMATION FOR SEQ ID NO:73:

( i ) SEQUENCE CHARACTERISTICS:
        ( A ) LENGTH: 7 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:73:

```
Arg Arg Trp Trp Arg Phe Cys
1               5
```

( 2 ) INFORMATION FOR SEQ ID NO:74:

( i ) SEQUENCE CHARACTERISTICS:
        ( A ) LENGTH: 7 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:74:

```
Arg Arg Trp Trp Arg Phe Ile
1               5
```

( 2 ) INFORMATION FOR SEQ ID NO:75:

( i ) SEQUENCE CHARACTERISTICS:
        ( A ) LENGTH: 7 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:75:

```
Arg Arg Trp Trp Arg Phe Tyr
```

( 2 ) INFORMATION FOR SEQ ID NO:76:

( i ) SEQUENCE CHARACTERISTICS:
        ( A ) LENGTH: 7 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:76:

```
Arg  Arg  Trp  Trp  Arg  Phe  Val
 1                    5
```

( 2 ) INFORMATION FOR SEQ ID NO:77:

( i ) SEQUENCE CHARACTERISTICS:
        ( A ) LENGTH: 7 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:77:

```
Arg  Arg  Trp  Trp  Arg  Phe  Arg
 1                    5
```

( 2 ) INFORMATION FOR SEQ ID NO:78:

( i ) SEQUENCE CHARACTERISTICS:
        ( A ) LENGTH: 6 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:78:

```
Arg  Arg  Trp  Trp  Arg  Arg
 1                    5
```

( 2 ) INFORMATION FOR SEQ ID NO:79:

( i ) SEQUENCE CHARACTERISTICS:
        ( A ) LENGTH: 6 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:79:

```
Arg  Arg  Trp  Trp  Arg  His
 1                    5
```

( 2 ) INFORMATION FOR SEQ ID NO:80:

( i ) SEQUENCE CHARACTERISTICS:
        ( A ) LENGTH: 7 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:80:

```
Arg  Arg  Trp  Trp  Cys  Val  Arg
 1                    5
```

( 2 ) INFORMATION FOR SEQ ID NO:81:

( i ) SEQUENCE CHARACTERISTICS:
    ( A ) LENGTH: 7 amino acids
    ( B ) TYPE: amino acid
    ( D ) TOPOLOGY: linear ( i i ) MOLECULE TYPE: peptide ( x i ) SEQUENCE DESCRIPTION: SEQ ID NO:81:

Arg Arg Trp Trp Arg Phe Lys
1               5

( 2 ) INFORMATION FOR SEQ ID NO:82:

( i ) SEQUENCE CHARACTERISTICS:
        ( A ) LENGTH: 7 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:82:

Lys Arg Arg Trp Trp Arg Phe
1               5

( 2 ) INFORMATION FOR SEQ ID NO:83:

( i ) SEQUENCE CHARACTERISTICS:
        ( A ) LENGTH: 6 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:83:

Arg Arg Trp Trp Cys Gly
1               5

( 2 ) INFORMATION FOR SEQ ID NO:84:

( i ) SEQUENCE CHARACTERISTICS:
        ( A ) LENGTH: 6 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:84:

Arg Arg Trp Trp Arg Trp
1               5

( 2 ) INFORMATION FOR SEQ ID NO:85:

( i ) SEQUENCE CHARACTERISTICS:
        ( A ) LENGTH: 6 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:85:

Arg Arg Trp Trp Cys Cys
1               5

( 2 ) INFORMATION FOR SEQ ID NO:86:

( i ) SEQUENCE CHARACTERISTICS:
        ( A ) LENGTH: 6 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:86:

Arg Arg Trp Trp Cys Met
1               5

( 2 ) INFORMATION FOR SEQ ID NO:87:

( i ) SEQUENCE CHARACTERISTICS:
        ( A ) LENGTH: 6 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:87:

Arg Arg Trp Trp Cys Phe
1               5

( 2 ) INFORMATION FOR SEQ ID NO:88:

( i ) SEQUENCE CHARACTERISTICS:
        ( A ) LENGTH: 6 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:88:

Asp Val Pro Asp Tyr Ala
1               5

( 2 ) INFORMATION FOR SEQ ID NO:89:

( i ) SEQUENCE CHARACTERISTICS:
        ( A ) LENGTH: 13 amino acids
        ( B ) TYPE: amino acid
        ( D ) TOPOLOGY: linear ( i i ) MOLECULE TYPE: peptide ( i x ) FEATURE:
        ( A ) NAME/KEY: Modified-site
        ( B ) LOCATION: 1
        ( D ) OTHER INFORMATION: /label=Xaa
            / note="Xaa is N-acetyl tyrosine."

( i x ) FEATURE:
        ( A ) NAME/KEY: Modified-site
        ( B ) LOCATION: 13
        ( D ) OTHER INFORMATION: /label=Xaa
            / note="Xaa is serine amide."

( x i ) SEQUENCE DESCRIPTION: SEQ ID NO:89:

Xaa Pro Tyr Asp Val Pro Asp Tyr Ala Ser Leu Arg Xaa
1               5                   10

( 2 ) INFORMATION FOR SEQ ID NO:90:

( i ) SEQUENCE CHARACTERISTICS:
        ( A ) LENGTH: 6 amino acids
        ( B ) TYPE: amino acid
        ( D ) TOPOLOGY: linear ( i i ) MOLECULE TYPE: peptide ( i x ) FEATURE:
        ( A ) NAME/KEY: Modified-site
        ( B ) LOCATION: 1
        ( D ) OTHER INFORMATION: /label=Xaa
            / note="Xaa is N-acetyl aspartic acid."

(ix) FEATURE:
  (A) NAME/KEY: Modified-site
  (B) LOCATION: 6
  (D) OTHER INFORMATION: /label=Xaa
        / note="Xaa is alanine amide."

(xi) SEQUENCE DESCRIPTION: SEQ ID NO:90:

Xaa Val Pro Asp Tyr Xaa
1                   5

(2) INFORMATION FOR SEQ ID NO:91:

(i) SEQUENCE CHARACTERISTICS:
        (A) LENGTH: 6 amino acids
        (B) TYPE: amino acid
        (D) TOPOLOGY: linear (ii) MOLECULE TYPE: peptide (xi) SEQUENCE DESCRIPTION: SEQ ID NO:91:

Ser Thr Thr Ser Thr Gly
1                   5